US011890322B2

(12) United States Patent
Braun et al.

(10) Patent No.: US 11,890,322 B2
(45) Date of Patent: *Feb. 6, 2024

(54) METHODS FOR PROMOTING WOUND HEALING AND HAIR GROWTH COMPRISING GDNF ADMINISTRATION

(71) Applicant: The Jackson Laboratory, Bar Harbor, ME (US)

(72) Inventors: Robert E. Braun, Bar Harbor, ME (US); Manju Sharma, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/373,877

(22) Filed: Jul. 13, 2021

(65) Prior Publication Data
US 2022/0062381 A1 Mar. 3, 2022

Related U.S. Application Data

(60) Continuation of application No. 16/452,459, filed on Jun. 25, 2019, now abandoned, which is a division of application No. 14/775,386, filed as application No. PCT/US2014/027419 on Mar. 14, 2014, now Pat. No. 10,376,562.

(60) Provisional application No. 61/787,870, filed on Mar. 15, 2013.

(51) Int. Cl.
*A61K 38/18* (2006.01)
*C07K 14/475* (2006.01)
*A61K 8/64* (2006.01)
*A61Q 7/00* (2006.01)

(52) U.S. Cl.
CPC .............. *A61K 38/185* (2013.01); *A61K 8/64* (2013.01); *A61Q 7/00* (2013.01); *C07K 14/4756* (2013.01)

(58) Field of Classification Search
None
See application file for complete search history.

(56) References Cited

U.S. PATENT DOCUMENTS

| | | |
|---|---|---|
| 4,407,957 A | 10/1983 | Lim |
| 4,870,017 A | 9/1989 | Ben-Bassat et al. |
| 4,911,928 A | 3/1990 | Wallach |
| 5,641,749 A | 6/1997 | Yan et al. |
| 5,705,485 A | 1/1998 | Cini et al. |
| 5,733,875 A | 3/1998 | Martin |
| 5,741,778 A | 4/1998 | Martin et al. |
| 5,798,113 A | 8/1998 | Dionne et al. |
| 5,800,828 A | 9/1998 | Dionne et al. |
| 5,834,014 A | 11/1998 | Weiner et al. |
| 5,837,681 A | 11/1998 | Magal |
| 5,929,041 A | 7/1999 | Magal |
| 6,093,802 A | 7/2000 | Lin et al. |
| 6,184,200 B1 | 2/2001 | Hu |
| 6,221,376 B1 | 4/2001 | Lin et al. |
| 6,245,330 B1 | 6/2001 | Horellou et al. |
| 6,362,319 B1 | 3/2002 | Lin et al. |
| 7,226,758 B1 | 6/2007 | Lin et al. |
| 7,390,781 B2 | 6/2008 | Hu |
| 7,479,279 B2 | 1/2009 | Paulista et al. |
| 7,611,865 B2 | 11/2009 | Hu |
| 8,138,148 B2 | 3/2012 | Bock et al. |
| 8,383,114 B2 | 2/2013 | Sloey et al. |
| 10,376,562 B2 | 8/2019 | Braun et al. |
| 2003/0166537 A1 | 9/2003 | Hanke |
| 2004/0097456 A1 | 5/2004 | Paulista et al. |
| 2004/0127419 A1 | 7/2004 | Hu |
| 2006/0134155 A1* | 6/2006 | Dryer ............... A61Q 19/08 424/401 |
| 2006/0258576 A1 | 11/2006 | Immonen |
| 2010/0056440 A1 | 3/2010 | Rossomando et al. |
| 2010/0172865 A1 | 7/2010 | Shantha et al. |
| 2010/0311653 A1 | 12/2010 | Nevalaita et al. |
| 2011/0281802 A1 | 11/2011 | Armbruster et al. |
| 2011/0306546 A1 | 12/2011 | Armani et al. |
| 2013/0017285 A1 | 1/2013 | Bhatia |
| 2016/0022773 A1 | 1/2016 | Braun et al. |
| 2019/0307846 A1 | 10/2019 | Braun et al. |
| 2020/0147174 A1 | 5/2020 | Braun et al. |

FOREIGN PATENT DOCUMENTS

| | | |
|---|---|---|
| EP | 0610254 A1 | 8/1994 |
| EP | 0920448 A1 | 6/1999 |
| EP | 1372698 A2 | 1/2004 |
| JP | 2012246249 B2 | 12/2012 |

(Continued)

OTHER PUBLICATIONS

Birch et al., Clinical and Experimental Dermatology, 2002; 27, 383-388 (Year: 2002).*
Conley et al., Plant Biotechnology Journal (2011) 9, pp. 434-444 (Year: 2011).*
Botchkareva et al., New Roles for Glial Cell Line-Derived Neurotrophic Factor and Neurturin: Involvement in Hair Cycle Control. Am J Pathol. Mar. 2000;156(3):1041-53. doi: 10.1016/S0002-9440(10)64972-3.
International Search Report and Written Opinion, PCT/US2014/027419, dated Jul. 16, 2014, 10 pages.
International Preliminary Report on Patentability, PCT/US2014/027419, dated Sep. 15, 2015, 7 pages.
Aarabi, S. et al., "Hypertrophic scar formation following burns and trauma: new approaches to treatment," PLoS Med.., vol. 4(9):e234:7 pages (2007).

(Continued)

*Primary Examiner* — Christina M Borgeest
(74) *Attorney, Agent, or Firm* — Wolf, Greenfield & Sacks, P.C.

(57) ABSTRACT

The present invention generally relates to uses of glial cell line-derived growth factor (GDNF) in cutaneous wound healing and hair growth. Methods of effecting hair growth and/or wound healing which feature administration of GDNF, or a biologically active fragment thereof, to subjects, e.g., human subject, are disclosed herein. The invention relates also to formulations and kits for achieving the indicated pharmaceutical advantages.

18 Claims, 11 Drawing Sheets

Specification includes a Sequence Listing.

(56) References Cited

FOREIGN PATENT DOCUMENTS

| WO | WO 93/06116 A1 | 4/1993 |
|---|---|---|
| WO | WO 97/19694 A1 | 6/1997 |
| WO | WO 99/07843 A1 | 2/1999 |
| WO | WO 00/01815 A2 | 1/2000 |
| WO | WO 01/30375 A2 | 5/2001 |
| WO | WO 02/076494 A2 | 10/2002 |
| WO | WO 2005/023861 A2 | 3/2005 |
| WO | WO 2007/103182 A2 | 9/2007 |
| WO | WO 2014/152511 A1 | 9/2014 |

OTHER PUBLICATIONS

Adly, M.A., et al., "Analysis of the expression pattern of glial cell line-derived neurotrophic factor, neurturin, their cognate receptors GFRalpha-1 and GFRalpha-2, and a common signal transduction element c-Ret in the human scalp skin," J CutanPathol., vol. 33:799-808(2006).
Adly, M.A., et al., "Expression patterns of the glial cell line-derived neurotrophic factor, neurturin, their cognate receptors GFRalpha-1, GFRalpha-2, and a common signal transduction element c-Ret in the human skin hair follicles," J Am AcadDermatol., vol. 58:238-250 (2008).
Albers, K.M., et al., "Glial cell-line-derived neurotrophic factor expression in skin alters the mechanical sensitivity of cutaneous nociceptors," J Neurosci., vol. 26: 2981-2990 (2006).
Albers, K.M., et al., "The skin as a neurotrophic organ," Neuroscientist, vol. 13: 371-382 (2007).
Altschul et al., "Basic Local Alignment Search Tool," J. Mol. Biol. 215:403-410, (1990).
Altschul et al., "Gapped BLAST and PSI-BLAST: a new generation of protein database search programs," Nucleic Acids Research, vol. 25(17):3389-3402 (1997).
Altschuler, R.A., "Stress pathways in the rat cochlea and potential for protection from acquired deafness," Audiol Neurootol., vol. 7: 152-156. (2002).
Altschuler, R.A., et al. (1999). Rescue and regrowth of sensory nerves following deafferentation by neurotrophic factors. Ann N Y Acad Sci 884, 305-311.
Anand, P., "Neurotrophic factors and their receptors in human sensory neuropathies," Prog Brain Res., vol. 146: 477-492 (2004).
Anand, U., et al., "TRPA1 receptor localisation in the human peripheral nervous system and functional studies in cultured human and rat sensory neurons," Neurosci Lett., vol. 438: 221-227 (2008).
Aoki, Y., et al., "Expression and co-expression of VR1, CGRP, and IB4-binding glycoprotein in dorsal root ganglion neurons in rats: differences between the disc afferents and the cutaneous afferents," Spine (Phila Pa 1976), vol. 30: 1496-1500(2005).
Ayllon, J., et al., "Long-term response and postsurgical complete remissions after treatment with sunitinib malate, an oral multitargeted receptor tyrosine kinase inhibitor, in patients with metastatic renal cell carcinoma," Cancer Invest., vol. 29:282-285 (2011).
Baba, T., et al. "Electrical stimulation of the cerebral cortex exerts antiapoptotic, angiogenic, and anti-inflammatory effects in ischemic stroke rats through phosphoinositide 3-kinase/Akt signaling pathway," Stroke, vol. 40: e598-605 (2009).
Barrientos S, et al., "Growth factors and cytokines in wound healing," Wound Repair Regen, vol. 16:585-601 (2008).
Batchelor, P.E., et al., "Activated macrophages and microglia induce dopaminergic sprouting in the injured striatum and express brain-derived neurotrophic factor and glial cell line-derived neurotrophic factor," J Neurosci., vol. 19: 1708-1716.(1999).
Batchelor, P.E., et al., "Inhibition of brain-derived neurotrophic factor and glial cell line-derived neurotrophic factor expression reduces dopaminergic sprouting in the injured striatum," Eur J Neurosci., vol. 12: 3462-3468 (2000).
Batchelor, P.E., et al., "Macrophages and Microglia Produce Local Trophic Gradients That Stimulate Axonal Sprouting Toward but Not beyond the Wound Edge," Mol Cell Neurosci., vol. 21: 436-453 (2002).
Batchelor, P.E., et al., "Stimulation of axonal sprouting by trophic factors immobilized within the wound core," Brain Res., vol. 1209: 49-56 (2008).
Baudet, C., et al. "Positive and negative interactions of GDNF, NTN and ART in developing sensory neuron subpopulations, and their collaboration with neurotrophins," Development, vol. 127: 4335-4344 (2000).
Becker, D.L., et al., "Connexins in wound healing; perspectives in diabetic patients," Biochim. Biophys Acta, vol. 1818:2068-2075 (2011).
Bennett NT, et al., "Growth factors and wound healing: Part II. Role in normal and chronic wound healing," Am J Surg, . vol. 166:74-81 (1993).
Botchkareva et al., New roles for glial cell line-derived neurotrophic factor and neurturin: Involvement in hair cycle control. American Journal of Pathology. 2000;156(3):1041-1053.
Bourane, S., et al., "Low-threshold mechanoreceptor subtypes selectively express MafA and are specified by Ret signaling." Neuron, vol. 64: 857-870 (2009).
Bowenkamp, K.E., et al., "Intracerebroventricular glial cell line-derived neurotrophic factor improves motor function and supports nigrostriatal dopamine neurons in bilaterally 6-hydroxydopamine lesioned rats," Exp Neurol., vol. 145: 104-117.(1997).
Bradbury, E.J., et al., "The expression of P2X3 purinoreceptors in sensory neurons: effects of axotomy and glial-derived neurotrophic factor," Mol Cell Neurosci., vol. 12: 256-268 (1998).
Braiman-Wilksman, L. et al., "Novel Insights into Wound Healing Sequence of Events," Toxicol. Pathol., vol. 25: 767-779(2007).
Brem, H. et al. "Healing of elderly patients with diabetic foot ulcers, venous stasis ulcers, and pressure ulcers," Surg Technol Int., vol. 11, 161-167 (2003).
Bukowiecki et al., Wound-Healing Studies in Cornea and Skin: Parallels, Differences and Opportunities. Int J Mol Sci. Jun. 12, 2017;18(6):1257. doi: 10.3390/ijms18061257.
Burt, Evolutionary grouping of the transforming growth factor-beta superfamily. Biochem Biophys Res Commun. Apr. 30, 1992;184(2):590-5.
Carlsten et al., Society for Neuroscience Abstract Viewer and Itinerary Planner. $32^{nd}$ Annual Meeting of the Society for Neuroscience. Nov. 2002. Abstract No. 757.5.
Carlsten, J.A., et al., "Glial cell line-derived neurotrophic factor-responsive and neurotrophin-3-responsive neurons require the cytoskeletal linker protein dystonin for postnatal survival," J Comp Neurol., vol. 432: 155-168 (2001).
Cavanagh, P.R., et al. "The non-healing diabetic foot wound: fact or fiction?," Ostomy Wound Manage, vol. 44(3A supp), 6S-12S (1998).
Chang, H et al., "Genetic analysis of the mammalian transforming growth factor-beta superfamily," Endocri Rev, vol. 23(6):787-823 (2002).
Charron, M. et al., "A 3-kilobase region derived from the rat cathepsin L gene directs in vivo expression of a reporter gene in sertoli cells in a manner comparable to that of the endogenous gene," Biol Reprod, vol. 81(3):1641-1648 (2003).
Chen, S.H., et al., "Premarin stimulates estrogen receptor-alpha to protect against traumatic brain injury in male rats," Crit Care Med., vol. 37: 3097-3106 (2009).
Chi, J.H., "Scar-busting chondroitinase with peripheral nerve grafting promotes axonal regeneration in chronic spinal cord injury," Neurosurgery, vol. 66: N12 (2010).
Christianson, J.A., et al., "Restorative effects of neurotrophin treatment on diabetes-induced cutaneous axon loss in mice," Exp Neurol., vol. 179, 188-199 (2003).
Cobianchi, S., et al., "Differential effects of activity dependent treatments on axonal regeneration and neuropathic pain after peripheral nerve injury," Exp Neurol., vol. 240:157-167 (2013).
Deng, L.X., et al., "GDNF modifies reactive astrogliosis allowing robust axonal regeneration through Schwann cell-seeded guidance channels after spinal cord injury," Exp Neurol., vol. 229:238-250. (2011).
Deonarine, K., et al., "Gene expression profiling of cutaneous wound healing," J. Transl. Med., vol. 5 (2007).
Dhurat, R. et al., "Hair evaluation methods: merits and demerits," Int J Trichology 1(2): 108-119 (2009).

(56) References Cited

OTHER PUBLICATIONS

Diegelmann, R.F., et al., "Wound healing: an overview of acute, fibrotic and delayed healing," Front Biosci, vol. 9:283-289 (2004).

Donahue, T.R., et al., "CXCR2 and RET single nucleotide polymorphisms in pancreatic cancer," World J Surg., vol. 33, 710-715 (2009).

Ebadi, M., et al., "Neurotrophins and their receptors in nerve injury and repair," Neurochem Int., vol. 30: 347-374 (1997).

Eigenbrot et al., "X-ray structure of glial cell-derived neurotrophic factor at 1.9 A resolution and implications for receptor binding," Nat Struct Biol., vol. 4 (6):435-438 (1997).

Eketjall et al. "Distinct structural elements in GDNF mediate binding to GFRalpha1 and activation of the GFRalpha1-c-Ret receptor complex," EMBO, vol. 18(21): 5901-5910 (1999).

Elcin YM et al., "Controlled release of endothelial cell growth factor from chitosan-albumin microspheres for localized angiogenesis: in vitro and in vivo studies," Artif. Cell Blood Substit. Immobil Biotechnol., vol. 24 (3): 257-271 (1996).

Elitt, C.M., et al. "Artemin overexpression in skin enhances expression of TRPV1 and TRPA1 in cutaneous sensory neurons and leads to behavioral sensitivity to heat and cold," J Neurosci., vol. 26: 8578-8587 (2006).

Elitt, C.M., et al., "Overexpression of artemin in the tongue increases expression of TRPV1 and TRPA1 in trigeminal afferents and causes oral sensitivity to capsaicin and mustard oil," Brain Res., vol. 1230: 80-90 (2008).

Falanga V, et al., "The "trap" hypothesis of venous ulceration," Lancet, vol. 341:1006-1008 (1993).

Fernandez-San Millan et al., "Expression of recombinant proteins lacking methionine as N-terminal amino acid in plastids: human serum albumin as a case study," J Biotechnol., vol. 127(4):593-604 (2007).

Freedberg M, et al., "Keratins and the keratinocyte activation cycle," J Invest Dermatol., vol. 116(5):633-640 (2001).

Freedman, G., et al. "Practical treatment of pain in patients with chronic wounds: pathogenesis-guided management," Am J Surg., vol. 188(1A Suppl):31-35 (2004).

Friedrich, R.E., et al., "Vascular wall cells contribute to tumourigenesis in cutaneous neurofibromas of patients with neurofibromatosis type 1. A comparative histological, ultrastructural and immunohistochemical study," Anticancer Res., vol. 32:2139-2158 (2012).

Fritzsch, B. et al. "Making and breaking the innervation of the ear: neurotrophic support during ear development and its clinical implications," Cell Tissue Res., vol. 295:369-382 (1999).

Fundin, B.T., et al., "A rapid and dynamic regulation of GDNF-family ligands and receptors correlate with the developmental dependency of cutaneous sensory innervation," Development, vol. 126: 2597-2610 (1999).

GenBank Submission; NIH/NCBI, Accession No. L19063.1. Lin et al., Jun. 8, 1993. 1 page.

Ghassemi, F., et al., "Beta1 adducin gene expression in DRG is developmentally regulated and is upregulated by glial-derived neurotrophic factor and nerve growth factor," Brain Res Mol Brain Res., vol. 90 :118-124 (2011).

Gilliver, S.C., et al., "MIF: a key player in cutaneous biology and wound healing," Exp. Dermatol.,vol. 20(1): 1-6 (2011).

Golden, J.P., et al., "Expression of neurturin, GDNF, and GDNF family-receptor mRNA in the developing and mature mouse," Exp Neurol., vol. 158: 504-528 (1999).

Grose R, et al., "Wound-healing studies in transgenic and knockout mice," Mol Biotechnol., vol. 28(2):147-166 (2004).

Gudi, V., et al., "Spatial and temporal profiles of growth factor expression during CNS demyelination reveal the dynamics of repair priming," PLoS One, vol. 6: e22623 (2011).

Gurtner GC, et al., "Wound repair and regeneration," Nature, vol. 453(7193):314-321 (2008).

Hackam, D.J., et al., "Cellular, biochemical, and clinical aspects of wound healing," Surg Infect., vol. 3 (Suppl 1), S23-S35 (2002).

Hakuba, N., et al., Adenovirus-mediated overexpression of a gene prevents hearing loss and progressive inner hair cell loss after transient cochlear ischemia in gerbils. Gene Ther 10, 426-433 (2003).

Hantash BM, et al.,"Adult and fetal wound healing," Front Biosci., vol. 13:51-61 (2008).

Harding, K.G., et al., "Wound chronicity and fibroblast senescence—implications for treatment," Int Wound J., vol. 2 (4):364-368 (2005).

Hellmich et al., "Embryonic expression of glial cell-line derived neurotrophic factor (GDNF) suggests multiple developmental roles in neural differentiation and epithelial-mesenchymal interactions.," Mech Dev., vol. 54(1): 95-105 (1996).

Hess, D.C., et al., "Stem cells and neurological diseases," Cell Prolif., vol. 41 (Suppl 1): 94-114 (2008).

Hiltunen, P.H., et al., "Sympathetic cholinergic target innervation requires GDNF family receptor GFR alpha 2," Mol Cell Neurosci., vol. 26: 450-457 (2004).

Hsieh, J.H., et al., "Patterns of target tissue reinnervation and trophic factor expression after nerve grafting," Plast Reconstr Surg. (2013).

Hsieh, Y.L., et al., "Effects of 4-methylcatechol on skin reinnervation: promotion of cutaneous nerve regeneration after crush injury," J Neuropathol Exp Neurol., vol. 68:1269-1281 (2009).

Huang et al., Abstracts presented at the 12th International Congress on Amino Acids, Peptides and Proteins. Amino Acids. Jul. 2011;41(1):S20.

Imamura, T., et al., "The microenvironment of freeze-injured mouse urinary bladders enables successful tissue engineering," Tissue Eng., Part A 15: 3367-3375 (2009).

Ishida, A., et al., "Approach to ex vivo gene therapy in the treatment of Parkinson's disease," Brain Dev., vol. 22 (Suppl 1):S143-147 (2000).

Jankowski, M.P., et al., "Enhanced artemin/GFRalpha3 levels regulate mechanically insensitive, heat-sensitive C-fiber recruitment after axotomy and regeneration," J Neurosci., vol. 30: 16272-16283 (2010).

Jeon, S.M., et al., "Monocyte chemoattractant protein-1 immunoreactivity in sensory ganglia and hindpaw after adjuvant injection," Neuroreport, vol. 19: 183-186. (2008).

Johanson, C., et al., "Traumatic brain injury and recovery mechanisms: peptide modulation of periventricular neurogenic regions by the choroid plexus-CSF nexus," J Neural Transm., vol. 118: 115-133 (2011).

Jones, K.R., et al., "Evidence-based management of chronic wounds," Adv. Skin Wound Care vol. 20(11):591-600 (2007).

Kanzaki, S., et al., "From gene identification to gene therapy," Audiol Neurootol., vol. 7: 161-164 (2002).

Kanzaki, S., et al., "Glial cell line-derived neurotrophic factor and chronic electrical stimulation prevent VIII cranial nerve degeneration following denervation," J Comp Neurol., vol. 454: 350-360 (2002).

Kao, C.H., et al., "Body cooling ameliorating spinal cord injury may be neurogenesis-, anti-inflammation- and angiogenesis-associated in rats," J Trauma, vol. 70: 885-893 (2011).

Karlin, S. et al., "Methods for assessing the statistical significance of molecular sequence features by using general scoring schemes," Proc. Natl. Acad. Sci. USA, vol. 87:2264-2268, (1990).

Karlin, S., "Applications and statistics for multiple high-scoring segments in molecular sequences," Proc. Natl. Acad. Sci., USA, vol. 90:5873-5877 (1993).

Kato, M et al., "RET tyrosine kinase enhances hair growth in association with promotion of melanogenesis," Oncogene, vol. 20: 7536-7541 (2001).

Kawamoto, K., et al., "Gene-based therapy for inner ear disease," Noise Health, vol. 3: 37-47 (2001).

Kawamoto, K., et al., "Hearing and hair cells are protected by adenoviral gene therapy with TGF-beta1 and GDNF," Mol Ther., vol. 7: 484-492 (2003).

Keithley, E.M., et al., "GDNF protects the cochlea against noise damage," Neuroreport, vol. 9, 2183-2187 (1998).

Kesser, B.W., et al. "Gene transfer in human vestibular epithelia and the prospects for inner ear gene therapy," Laryngoscope, vol. 118:821-831 (2008).

(56) References Cited

OTHER PUBLICATIONS

Kiasalari, Z., et al., "Identification of perineal sensory neurons activated by innocuous heat," J Comp Neurol., vol. 518:137-162 (2010).
Kiwanuka, E. et al., "Harnessing Growth Factors to Influence Wound Healing," Growth Factors and Wound Healing, Clin. Plastic Surgery, vol. 39:239-248 (2012).
Koltzenburg, M., et al., "The changing sensitivity in the life of the nociceptor," Pain Suppl., vol. 6: S93-S102 (1999).
Komeda, M., et al., "The influence of interleukin-1 receptor antagonist transgene on spiral ganglion neurons," Hear Res., vol. 131:1-10 (1999).
Kuang, R., et al., "Glial cell line-derived neurotrophic factor. Potential for otoprotection," Ann N Y Acad Sci., vol. 884:270-291 (1999).
Kumar, S. "Classification and management of acute wounds," Surgery, vol. 26:43-47 (2008).
Lawson, J., et al., "Changes in skin levels of two neutotrophins (glial cell line derived neurotrohic factor and neurotrophin-3) cause alterations in cutaneous neuron responses to mechanical stimuli;" Acta Physiologica Sinica, vol. 60: 584-596(2008).
Lee, Y.J., et al., "Upregulation of bradykinin B2 receptor expression by neurotrophic factors and nerve injury in mouse sensory neurons," Mol Cell Neurosci., vol. 19: 186-200. (2002).
Leibovich, S.J., et al., "The role of the macrophage in wound repair. A study with hydrocortisone and antimacrophage serum," Am. J. Pathol., vol. 78(1):71-100 (1975).
Levin, M. E., "Preventing amputation in the patient with diabetes," Diabetes Care., vol. 18(10): 1383-1394 (1995).
Lin et al. "GDNF: a glial cell line-derived neurotrophic factor for midbrain dopaminergic neurons," Science, vol. 260 (5111): 1130-1132 (1993).
Lin et al., "Purification and initial characterization of rat B49 glial cell line-derived neurotrophic factor," Neurochem, vol. 63 (2): 758-768 (1994).
Lin, Y.C., et al., "Keratin gel filler for peripheral nerve repair in a rodent sciatic nerve injury model;" Plast Reconstr Surg., vol. 129: 67-78 (2012).
Lindfors, P.H., et al., "Deficient nonpeptidergic epidermis innervation and reduced inflammatory pain in glial cell line-derived neurotrophic factor family receptor alpha2 knock-out mice," J Neurosci., vol. 26:1953-1960 (2006).
Lisse et al., GDNF promotes hair formation and cutaneous wound healing by targeting bulge stem cells. NPJ Regen Med. Jun. 12, 2020;5:13.
Liu, Y., et al. "Protection against aminoglycoside-induced ototoxicity by regulated AAV vector-mediated GDNF gene transfer into the cochlea," Mol Ther., vol. 16: 474-480 (2008).
Lovvom, HN 3rd, et al., "Relative distribution and crosslinking of collagen distinguish fetal from adult sheep wound repair," Pediatr Surg., vol. 34(1):218-223 (1999).
Lu. B., et al., "A novel immunoprecipitation strategy identifies a unique functional mimic of the glial cell line-derived neurotrophic factor family ligands in the pathogen Trypanosoma cruzi," Infect Immun., vol. 76: 3530-3538 (2008).
Lupo M., "Cosmeceutical Peptides," Dermatol Surg., vol. 31 :832-836 (2005).
Lupo M., et al., "Cosmeceutical peptides," Dermatol Ther., vol. 20(7 Pt 2)::343-349 (2007).
Machine translation of the specification of published Korean application KR100889460; filed Nov. 19, 2007. 13 pages total.
Malgrange, B., et al., "Expression of growth factors and their receptors in the postnatal rat cochlea," Neurochem Res., vol. 23:1133-1138 (1998).
Malgrange, B., et al., "Identification of factors that maintain mammalian outer hair cells in adult organ of Corti explants," Hear Res., vol. 170: 48-58 (2002).
Malin, S., et al., "TRPV1 and TRPA1 function and modulation are target tissue dependent" J Neurosci., vol. 31: 10516-10528 (2011).
Malin, S.A., et al., "Glial cell line-derived neurotrophic factor family members sensitize nociceptors in vitro and produce thermal hyperalgesia in vivo," J Neurosci., vol. 26: 8588-8599 (2006).
Marchler-Baeur, M. et al., "CDD: conserved domains and protein three-dimensional structure," Nucleic Acids Res., vol. 41:D348-352, 2013.
Martin P, et al., "Inflammatory cells during wound repair: the good, the bad and the ugly," Trends Cell Biol., vol. 15 (11):599-607 (2005).
Martin, D.M., et al., "Gene-based diagnostic and treatment methods for tinnitus," Int Tinnitus, vol. 9:3-10 (2003).
Mast BA, et al., "Interactions of cytokines, growth factors, and proteases in acute and chronic wounds," Wound Repair Regen., vol. 4(4):411-420 (1996).
McLeod, M., et al., "Erythropoietin and GDNF enhance ventral mesencephalic fiber outgrowth and capillary proliferation following neural transplantation in a rodent model of Parkinson's disease," Eur J Neurosci., vol. 24:361-370 (2006).
Molliver, D.C., et al., "Overexpression of NGF or GDNF alters transcriptional plasticity evoked by inflammation," Pain, vol. 113: 277-284 (2005).
Morimoto, T., et al., "Striatal stimulation nurtures endogenous neurogenesis and angiogenesis in chronic-phase schemic stroke rats," Cell Transplant, vol. 20: 1049-1064 (2011).
Mosser, D.M., et al., "Exploring the full spectrum of macrophage activation," Nature Rev. Immunol., vol. 8:958-969 (2008).
Mousley, M., "Diabetes and its effect on wound healing and patient care," Nurs Times, vol. 99(42): 70-74 (2003).
Murota, H., et al., "Artemin causes hypersensitivity to warm sensation, mimicking warmth-provoked pruritus in atopic dermatitis," J Allergy Clin Immunol., vol. 130: 671-682/e674 (2012).
Mustoe T., "Understanding chronic wounds: a unifying hypothesis on their pathogenesis and implications for therapy," Am J Surg., vol. 187(5A):65S-70S (2004).
Muzzarelli, "Chitins and chitosans for the repair of wounded skin, nerve, cartilage and bone," RAA, Carbohydrate Polymers: vol. 76: 167-182 (2009).
Myers, E. et al., "Optimal alignments in linear space," Cabios, vol. 4(1): 11-17(1988).
Nakagawa et al., "Enzymatic Cleavage of Amino Terminal Methionine from Recombinant Human Interleukin 2 and Growth Hormone by Aminopeptidase M," Nature Biotech, vol. 5:824-827 (1987).
Nakajima, T., et al., "Differences in innervation and innervated neurons between hip and inguinal skin," Clin Orthop Relat Res., vol. 466: 2527-2532 (2008).
Nakamura, A., et al., "Recent advances in neuropharmacology of cutaneous nociceptors," Jpn J Pharmacol., vol. 79: 427-431 (1999).
Narita, N., et al., "Functional Ret G691S polymorphism in cutaneous malignant melanoma," Oncogene, vol. 28: 3058-3068 (2009).
Nwomeh BC, et al., "Physiology of the chronic wound," Clin Plast Surg., vol. 25(3):341-356 (1998).
Obata, K., et al., "TRPA1 induced in sensory neurons contributes to cold hyperalgesia after inflammation and nerve injury," J Clin Invest., vol. 115: 2393-2401 (2005).
Ogiso T, et al., "Effect of positively and negatively charged liposomes on skin permeation of drugs," (2001). J Drug Targeting, vol. 9(1):49-59 (2001).
Okun, E., et al., "Upregulation of carp GDNF mRNA by the immunomodulator AS101," Dev Comp Immunol., vol. 30:441-446 (2006).
Papaetis, G.S., et al., "Sunitinib: a multitargeted receptor tyrosine kinase inhibitor in the era of molecular cancer therapies," BioDrugs, vol. 23:377-389 (2009).
Patel M, et al., "GDNF-chitosan blended nerve guides: a functional study," J tissue Eng. & Regenerative Med., vol. 1 (5):360-367 (2007).
Paus, R. et al., "The biology of hair follicles," NEJM, vol. 341(7):491-497 (1999).
Perala, N., et al., "Sema4C-Plexin B2 signalling modulates ureteric branching in developing kidney," Differentiation, vol. 81: 81-91 (2011).

(56) References Cited

OTHER PUBLICATIONS

Piltonen, M.et al., "Vascular endothelial growth factor C acts as a neurotrophic factor for dopamine neurons in vitro and in vivo," Neuroscience, vol. 192: 550-563 (2011).
Pitera, J.E., et al., "Fras1, a basement membrane-associated protein mutated in Fraser syndrome, mediates both the initiation of the mammalian kidney and the integrity of renal glomeruli," Hum Mol Genet., vol. 17: 3953-3964 (2008).
Qi H., et al., "Expression of glial cell-derived neurotrophic factor and its receptor in the stem- cell-containing human limbal epithelium," Br J Ophthalmol., vol. 92: 1269-1274 (2008).
Qun, L.X., et al., "Neurotrophic factors in the auditory periphery," Ann N Y Acad Sci., vol. 884: 292-304 (1999).
Ramot Y. et al. "Spermidine promotes human hair growth and is a novel modulator of human epithelial stem cell functions," PLoS One, vol. 6(7): e22564 (2011).
Rice, J., et al., "Transgenic rescue of aganglionosis and piebaldism in lethal spotted mice," Dev Dyn., vol. 217:120-132. (2000).
Robson MC, et al., "Wound healing trajectories as predictors of effectiveness of therapeutic agents," Arch Surg., vol. 135(7):773-777 (2000).
Rodero, M.P., et al., "Skin wound healing modulation by macrophages," Int. J. Clin. Exp. Pathol., vol. 3(7):643-653 (2010).
Roggenkamp, D., et al., "Atopic keratinocytes induce increased neurite outgrowth in a coculture model of porcine dorsal root ganglia neurons and human skin cells," J Invest Dermatol., vol. 132: 1892-1900 (2012).
Sadick et al., "Analysis of heregulin-induced ErbB2 phosphorylation with a high-throughput Kinase receptor activation enzyme-linked immunosorbant assay," Anal. Biochem., vol. 235(2): 207-214 (1996).
Sakai, A., et al., "Profiling the cytokines in gingival crevicular fluid using a cytokine antibody array," J Periodontol., vol. 77: 856-864 (2006).
Sanjay et al., "Identification of Newborn Cells by BrdU Labeling and Immunocytochemistry in Vivo," Methods in Mol Biol., vol. 438: 335-343 (2008).
Sariola, H., et al., "Cell lineages in the embryonic kidney: their inductive interactions and signalling molecules," Biochem Cell Biol., vol. 76: 1009-1016 (1998).
Sariola, H., et al., "The neurotrophic factors in non-neuronal tissues," Cell Mol Life Sci., vol. 58:1061-1066 (2001).
Sasaki, K., et al., "Analysis of serum angiogenic factors in a young multiple myeloma patient with high-output cardiac failure," Int J Hematol., vol. 86: 72-76 (2007).
Scheper, V., et al., Effects of delayed treatment with combined GDNF and continuous electrical stimulation on spiral ganglion cell survival in deafened guinea pigs.J Neurosci Res 87, 1389-1399 (2009).
Schmidt-Ullrich and Paus, "Molecular principles of hair follicle induction and morphogenesis," BioEssays, vol. 27(3): 247-261 (2005).
Schultz et al., EGF and TGF-alpha in wound healing and repair. J Cell Biochem. Apr. 1991;45(4):346-52.
Shang, J., et al., "Strong neurogenesis, angiogenesis, synaptogenesis, and antifibrosis of hepatocyte growth factor in rats brain after transient middle cerebral artery occlusion," J Neurosci Res., vol. 89: 86-95 (2011).
Shi, H., et al., "Glial cell line-derived neurotrophic growth factor increases motility and survival of cultured mesenchymal stem cells and ameliorates acute kidney injury," Am J Physiol Renal Physiol., vol. 294: F229-235 (2008).
Shibata, S.B., et al., "Administration of amitriptyline attenuates noise-induced hearing loss via glial cell line-derived neurotrophic factor (GDNF) induction," Brain Res., vol. 1144:74-81 (2007).
Shimamura, M., et al., "Experimental and clinical application of plasmid DNA in the field of central nervous diseases," Curr Gene Ther., vol. 11: 491-500 (2011).
Shoji, F., et al., "Differential protective effects of neurotrophins in the attenuation of noise-induced hair cell loss," Hear Res., vol. 146:134-142 (2000).

Shoji, F., et al., "Glial cell line-derived neurotrophic factor has a dose dependent influence on noise-induced hearing loss in the guinea pig cochlea," Hear Res., vol. 142: 41-55 (2000).
Sindrilaru, A., et al., "An unrestrained proinflammatory M1 macrophage population induced by iron impairs wound healing in humans and mice,". Clin. Invest., vol. 121(3):985-997 (2011).
Singer, A.J., et al., "Cutaneous wound healing," N. Engl. J. Med., vol. 341(10):738-746 (1999).
Steele, C. et al., "Corneal wound Healing: a review," Optometry Today, Sep. 24, 1999, pp. 28-32.
Stenn and Paus "Controls of Hair Follicle Cycling". Physiological Reviews, vol. 81 (1): 449-494 (2001).
Stover, T., et al., "Glial cell line-derived neurotrophic factor (GDNF) and its receptor complex are expressed in the auditory nerve of the mature rat cochlea," Hear Res., vol. 155, 143-151 (2001).
Stucky, C.L., et al., "The low-affinity neurotrophin receptor p75 regulates the function but not the selective survival of specific subpopulations of sensory neurons," J Neurosci., vol. 17, 4398-4405 (1997).
Suzuki, M., et al., "Effect of transgenic GDNF expression on gentamicin-induced cochlear and vestibular toxicity," Gene Ther., vol. 7:1046-1054 (2000).
Takasu, K., et al., "Overexpression of GDNF in the uninjured DRG exerts analgesic effects on neuropathic pain following segmental spinal nerve ligation in mice," J Pain, vol. 12: 1130-1139 (2011).
Takeda, M. et al., "Glial cell line-derived neurotrophic factor acutely modulates the excitability of rat small-diameter trigeminal ganglion neurons innervating facial skin," Brain Behav Immun., vol. 24: 72-82 (2010).
Takeda, M., et al., "Glial cell line-derived neurotrophic factor modulates the excitability of nociceptive trigeminal ganglion neurons via a paracrine mechanism following inflammation," Brain Behav Immun., vol. 28: 100-107 (2013).
Tang, M.J., et al., "The RET-glial cell-derived neurotrophic factor (GDNF) pathway stimulates migration and chemoattraction of epithelial cells," J Cell Biol., vol. 142:1337-1345. (1998).
Tang, X. et al., "In vivo study on tissue engineered skeletal muscle with hypoglossal nerve implantation," Zhongguo Xiu Fu Chong Jian Wai Ke Za Zhi., vol. 26: 359-364 (2012) (Abstract only).
Tarnuzzer RW, et al., "Biochemical analysis of acute and chronic wound environments," Wound Repair Regen., vol. 4 (3):321-325 (1996).
Taylor, A.M., et al., "GDNF levels in the lower lip skin in a rat model of trigeminal neuropathic pain: implications for nonpeptidergic fiber reinnervation and parasympathetic sprouting," Pain, vol. 152: 1502-1510. (2011).
[No Author Listed], The printout of the website from the Mayo Clinic, downloaded Nov. 28, 2017 from mayoclinic.org/diseases-conditions/hair-loss/basics/treatment/con-20-027666?p=1; 7 pages total. (Year: 2017).
Tian, Y.Y., et al., "Favorable effects of VEGF gene transfer on a rat model of Parkinson disease using adeno-associated viral vectors," Neurosci Lett., vol. 421: 239-244 (2007).
Tokime, K., et al., "Enhanced production and secretion of glial cell line-derived neurotrophic factor and nerve growth factor from the skin in atopic dermatitis mouse model," Arch Dermatol Res., vol. 300: 343-352 (2008).
Tom, V.J., et al., "Combining peripheral nerve grafts and chondroitinase promotes functional axonal regeneration in the chronically injured spinal cord," J Neurosci ., vol. 29:14881-14890 (2009).
Trupp, M., et al., "Peripheral expression and biological activities of GDNF, a new neurotrophic factor for avian and mammalian peripheral neurons," J Cell Biol., vol. 130: 137-148 (1995).
Unezaki, S., et al., "Effects of neurotrophic factors on nerve regeneration monitored by in vivo imaging in thy1-YFP transgenic mice," J Neurosci Methods, vol. 178: 308-315 (2009).
Unezaki, S., et al. "Involvement of Tyr1472 phosphorylation of NMDA receptor NR2B subunit in postherpetic neuralgia in model mice," Mol Pain, vol. 8: 59 (2012).
Valacchi, G. et al., "Emergin Topics in Cutaneous Wound Repair," Ann. N.Y. Acad., Sci., 1259: 136-144 (2012).

(56) References Cited

OTHER PUBLICATIONS

Valdes-Sanchez, T., et al., BDNF is essentially required for the early postnatal survival of nociceptors, Dev Biol., vol. 339: 465-476. (2010).

Vauclair, S. et al., "Notch1 is essential for postnatal hair follicle development and homeostasis," Developmental Biology, vol. 284:184-193 (2005).

Vellani, V., et al., "Protease activated receptors 1 and 4 sensitize TRPV1 in nociceptive neurons," Mol Pain, vol. 6: 61 (2010).

Vellani, V., et al., "Sensitization of transient receptor potential vanilloid 1 by the prokineticin receptor agonist Bv8," J Neurosci., vol. 26: 5109-5116 (2006).

Wang, D., et al., "Preclinical anti-angiogenesis and anti-tumor activity of SIM010603, an oral, multi-targets receptor tyrosine kinases inhibitor," Cancer Chemother Pharmacol., vol. 69: 173-183 (2012).

Wang, S., et al. "Effects of the neurotrophic factor artemin on sensory afferent development and sensitivity," Sheng Li Xue Bao, vol. 60: 565-570 (2008).

Wang, T., et al., "Neurturin Overexpression in Skin Enhances Expression of TRPM8 in Cutaneous Sensory Neurons and Leads to Behavioral Sensitivity to Cool and Menthol," J Neurosci., vol. 33: 2060-2070 (2013).

Wang, T., et al., "Phenotypic switching of nonpeptidergic cutaneous sensory neurons following peripheral nerve injury," PLoS One, vol. 6: e28908 (2011).

Wei, D., et al., "Survival, synaptogenesis, and regeneration of adult mouse spiral ganglion neurons in vitro," Dev Neurobiol., vol. 67:108-122 (2007).

Wei, L., et al., "Transplantation of hypoxia preconditioned bone marrow mesenchymal stem cells enhances angiogenesis and neurogenesis after cerebral ischemia in rats," Neurobiol Dis., vol. 46: 635-645 (2012).

Weinkauf, B., et al.,"Local gene expression changes after UV-irradiation of human skin," PLoS One, vol. 7: e39411 (2012).

Werner S, et al., "Keratinocyte-fibroblast interactions in wound healing," J. Invest Dermatol., vol. 127(5):998-1008 (2007).

Werner S, et al., "Regulation of wound healing by growth factors and cytokines," Physiol Rev., vol. 83:835-870 (2003).

Wertheimer, E. "Diabetic skin complications: a need for reorganizing the categories of diabetes-associated complications," Isr Med Assoc J., vol. 6(5):287-289 (2004).

Whitney, J.D., "Overview: acute and chronic wounds," Nurs. Clin. North Am., vol. 40(2):191-205 (2005).

Wood, M.D., et al., "GDNF released from microspheres enhances nerve regeneration after delayed repair," Muscle Nerve, vol. 46: 122-124 (2012).

Xu, P., et al., "Activin induces tactile allodynia and increases calcitonin gene-related peptide after peripheral inflammation," J Neurosci., vol. 25: 9227-9235 (2005).

Yagi, M., et al., "Hair cell protection from aminoglycoside ototoxicity by adenovirus-mediated overexpression of glial cell line-derived neurotrophic factor," Hum Gene Ther., vol. 10:813-823 (1999).

Yagi, M., et al., "Spiral ganglion neurons are protected from degeneration by GDNF gene therapy," J Assoc Res Otolaryngol, vol. 1: 315-325 (2000).

Yamaguchi, Y., et al. "Cutaneous wound healing: an update," J Dermatol., vol. 28(10): 521-534: (2001).

Yamamoto, N., et al. "Expression and effects of glial cell line-derived neurotrophic factor on periodontal ligament cells," J Clin Periodontol., vol. 39: 556-564 (2012).

Yamasoba, T., et al., "Absence of hair cell protection by exogenous FGF-1 and FGF-2 delivered to guinea pig cochlea in vivo," Noise Health, vol. 3: 65-78 (2001).

Yamasoba, T., et al., "Attenuation of cochlear damage from noise trauma by an iron chelator, a free radical scavenger and glial cell line-derived neurotrophic factor in vivo," Brain Res., vol. 815: 317-325 (1999).

Yang, C. et al., "Distribution of GDNF family receptor alpha3 and RET in rat and human non-neural tissues," J Mol Histol., vol. 37(1-2):69-77. (2006).

Yang, W., et al., Synergetic protective effects of glial cell line-derived neurotrophic factor combined with neurotrophin-3 in F-actin on hair cell after noise trauma, Zhonghua Er Bi Yan Hou Ke Za Zhi, vol. 36: 342-345 (2001).

Ylikoski, J., et al., "Guinea pig auditory neurons are protected by glial cell line-derived growth factor from degeneration after noise trauma," Hear Res., vol. 124:17-26 (1998).

Yoon et al., "Induction of hair growth by insulin-like growth factor-1 in 1,763 MHz radiofrequency-irradiated hair follicle cells," PLoS One, vol. 6(12): e28474 (2011).

Yoshida, T., et al., "Hematopoietic stem cells prevent hair cell death after transient cochlear ischemia through paracrine effects," Neuroscience, vol. 145: 923-930 (2007).

Yoshida, T., et al., "Immunohistochemical localization of glial cell line-derived neurotrophic factor and its receptor Ret in the rat sweat gland," Kurume Med J. vol. 51: 193-202 (2004).

You, L., et al., "Glial cell-derived neurotrophic factor (GDNF)-induced migration and signal transduction in corneal epithelial cells," Invest Ophthalmol Vis Sci., vol. 42: 2496-2504 (2001).

Zhou, Z., et al. (2006). Dynamic changes in nerve growth factor and substance P in the murine hair cycle induced by depilation. J Dermatol 33, 833-841 (2006).

Zwick M., et al., "Glial cell line-derived neurotrophic factor is a survival factor for isolectin B4-positive, but not vanilloid receptor 1-positive, neurons in the mouse," J Neurosci., vol. 22: 4057-4065 (2002).

\* cited by examiner

SEQUENCE LISTING

```
<160> NUMBER OF SEQ ID NOS: 27

<210> SEQ ID NO 1
<211> LENGTH: 3810
<212> TYPE: DNA
<213> ORGANISM: Homo sapiens
<220> FEATURE:
<221> NAME/KEY: misc_feature
<223> OTHER INFORMATION: Homo sapiens glial cell derived neurotrophic
      factor (GDNF)

<400> SEQUENCE: 1
ccgcctccag cgcgcccttg ctgccccgcg cgaccccagg attgcgaact cttgcccctg      60
acctgttggg cggggctccg cgctccagcc atcagcccgg atgggtctcc tggctgggac     120
ttggggcacc tggagttaat gtccaaccta gggtctgcgg agacccgatc cgaggtgccg     180
ccgccggacg ggactttaag atgaagttat gggatgtcgt ggctgtctgc ctggtgctgc     240
tccacaccgc gtccgccttc ccgctgcccg ccggtaagag gcctcccgag gcgcccgccg     300
aagaccgctc cctcggccgc cgccgcgcgc ccttcgcgct gagcagtgac tcaaatatgc     360
cagaggatta tcctgatcag ttcgatgatg tcatggattt tattcaagcc accattaaaa     420
gactgaaaag gtcaccagat aaacaaatgg cagtgcttcc tagaagagag cggaatcggc     480
```

-continued

| | |
|---|---|
| aggctgcagc tgccaaccca gagaattcca gaggaaaagg tcggagaggc cagaggggca | 540 |
| aaaaccgggg ttgtgtctta actgcaatac atttaaatgt cactgacttg ggtctgggct | 600 |
| atgaaaccaa ggaggaactg attttaggt actgcagcgg ctcttgcgat gcagctgaga | 660 |
| caacgtacga caaatattg aaaaacttat ccagaaatag aaggctggtg agtgacaaag | 720 |
| tagggcaggc atgttgcaga cccatcgcct ttgatgatga cctgtcgttt ttagatgata | 780 |
| acctggttta ccatattcta agaaagcatt ccgctaaaag gtgtggatgt atctgactcc | 840 |
| ggctccagag actgctgtgt attgcattcc tgctacagtg caaagaaagg gaccaaggtt | 900 |
| cccaggaaat gtttgcccag aatggaagat gaggaccaag gaggcggagg aggaggaaga | 960 |
| agaagaggag gaggaggagg aggaggagga ggaggaggaa ggcagccatc atgggagcct | 1020 |
| ggtagaggga gatccagcta cagacaactg gacaggagag agagaaaaca gccctctgga | 1080 |
| ttctccagga tggcagccga tgtcactaga agctcagggc tgatgttcct ggttggctat | 1140 |
| tgccaccatt tcagctgata cagtccacca tcactgatta ccggcgcggt tgcggtggat | 1200 |
| gcacttgaac caaccagtg tatctcctgt gatttgtttt catgtgtccg aagacaccag | 1260 |
| ggaaacagag atcctggtgt tgttccttgt tattacgttt tactgctgaa agtaagaggt | 1320 |
| ttatttttct gtcactcagt ggagacatac cctggaaagg agaggggaaa aaaaagcaa | 1380 |
| agatacaaga gataatcacc tttgcattg aaagttgagg cccgaggttt actacaacca | 1440 |
| gcattttgc caacgttggg tgattgattt ccatcacggt gtgtggggtg gaagaagtt | 1500 |
| ggctaggaac caaaaaggct gtgctcatga ttaaacacaa acctgaaggt atttcctta | 1560 |
| tgtccttgga aacaggaaac gagttgtggt tttcgccagc attcttgtag gagagaatcg | 1620 |
| gggaaggccc cgaactgccc ccgggcaggg agagcccctc aggcctgttg gtttacagag | 1680 |
| agacagatgt tacataacca gctccgttga tgcgtggtca ccagtgacca gagaagctac | 1740 |
| tcgatgcaat gcatctgttt cagatacaga aatatagaga agatatttat tgaaatttaa | 1800 |
| gttattgtta tttattaccg ttcactaatg aatttctctt ttttcccta tttattaaag | 1860 |
| tttcttttca aggtgccaa agtatatgtg ctcgcaaaat gcaagaaag gtgacaaaag | 1920 |
| gaaatttgaa ttgggaacaa gggtccatgc ttttcaaagt attaaaaagt tttttgccag | 1980 |
| gcaaaaatca cttactttac ctttttaaga aaatttgtca ttaatttcc ccagatttca | 2040 |
| gcatttttcc caattttat ttgtggagca tctcaggcaa gcccccttc ctggagcagc | 2100 |
| gtgcagagac cactggcact tgactttatt tcttccttgc tccattgctg aacagaaatg | 2160 |
| tcgtgggctc cacttcctgt tgtctttaag ctcttagtcc cctccacgta tacctatctg | 2220 |
| tactatgcat aaccatatgt agaaaaggtt cagttccttt tagtaggtag tcctggatttt | 2280 |
| aatgctgacc taaagtaat gtcgacaatg ctgtcaggta gctgccgttc taccgactcc | 2340 |
| ctccatccct gcccacccac tgccctcccg agaatatgct ggctgcccag tgcagcccgg | 2400 |
| gagacacagg ggccttccag aggtagggtc taccaggtcc tgtacaaccc ctgggctgtc | 2460 |
| accgggggtc aacagctgct gctcctatat acccaaacac ctgacagctc cctggggagc | 2520 |
| agatggctga aagggtgct gaggaagcca tattgggacc agccacagcc acacacatgg | 2580 |
| agcctcatac ttaggagcgt gctgccttta aatgaaggtg gtcggggcca gtgcagcggc | 2640 |
| tcacacccat aatcccaaca cttttggaaag ccaaggtggg aggatctctt gaacccagga | 2700 |
| gtttgagacc agcttgggca acataggag accctgtctc tacagaaact ttaaaaatta | 2760 |
| ggcaggcatg atggtgcaca cctgtggtcc cagctactca agaggctgaa ggaggatcac | 2820 |
| ttgagtccag aaggtcgagg ctgcagtgag ctgtgatcat gccactgcac tccagcctaa | 2880 |

-continued

| | |
|---|---|
| gtgacagtgc ggtaccctgt ctcaaaaaaa aaaaaaaaa aaaaagagg ttggagcagg | 2940 |
| aggaagcata ggggcgggaa cagccacctc ctccatgccc tagattgtga atttatcggg | 3000 |
| cagccaacac atgtatgaca cactaggccc tgtattacag cttgttacgc atttcataaa | 3060 |
| agggattttc attaaggaga taatctatta ctacctacct tagtggctac tagtataaaa | 3120 |
| ctatgacaga tttagcaatt aaatgaaata ctggcctcca tcaaataatc atagtaacaa | 3180 |
| gaagcagcag ttaccagaca tctgatcccc ttcccccaaa atacccaaat tcttcatggt | 3240 |
| tctgcccttc tctgtccttt ctgctcccct tgctcgcctg ggaaatggag gaaaggcctt | 3300 |
| ccctctcaca ctgtcttggg atcttgctga gaattcagac tgctcgaaac agtgacaaac | 3360 |
| cccagccatc cagtcattcg tggagcacaa tttggatgtg ccccagggg catctgtccc | 3420 |
| attcagagaa ccttggcagt gcgatggcca ctgttcccag gcttcaacct cagtgacccc | 3480 |
| ccccaacaac tccccatgga gagtccctgc ccaaaaaagc tgtaggatcc aagggggtgtc | 3540 |
| aatagctcgt tcccggcatc acctacacac acaagcagg ttttaatgga agcaagttgc | 3600 |
| tccaccaaat ccacaaaagg gtaaagtttg tgattttct ttatcattgc gatcaccatc | 3660 |
| tgataccgta aggagtgcac ttgtttggaa gttctgactt ctctgatctg tcttggtcgt | 3720 |
| ttgtgttata aaccaaagt tctctacaga cttatttttt gtacaatatc attttgtaac | 3780 |
| tttttacaaa taaaaactca tttctattgc | 3810 |

<210> SEQ ID NO 2
<211> LENGTH: 3655
<212> TYPE: DNA
<213> ORGANISM: Homo sapiens
<220> FEATURE:
<221> NAME/KEY: misc_feature
<223> OTHER INFORMATION: Homo sapiens glial cell derived neurotrophic
      factor (GDNF)

<400> SEQUENCE: 2

| | |
|---|---|
| catacaggcc aaaagtctcc aagtccctgc taacttcttg ctctcgcaac agaataccta | 60 |
| tttaggtggg aagaatgagg tgtgggcggc aggctgggtg ccgccgccgg acgggacttt | 120 |
| aagatgaagt tatgggatgt cgtggctgtc tgcctggtgc tgctccacac cgcgtccgcc | 180 |
| ttcccgctgc ccgccgcaaa tatgccagag gattatcctg atcagttcga tgatgtcatg | 240 |
| gattttattc aagccaccat taaaagactg aaaaggtcac cagataaaca aatggcagtg | 300 |
| cttcctagaa gagagcggaa tcggcaggct gcagctgcca acccagagaa ttccagagga | 360 |
| aaaggtcgga gaggccagag gggcaaaaac cggggttgtg tcttaactgc aatacattta | 420 |
| aatgtcactg acttgggtct gggctatgaa accaaggagg aactgatttt taggtactgc | 480 |
| agcggctctt gcgatgcagc tgagacaacg tacgacaaaa tattgaaaaa cttatccaga | 540 |
| aatagaaggc tggtgagtga caaagtaggg caggcatgtt gcagacccat cgcctttgat | 600 |
| gatgacctgt cgtttttaga tgataacctg gttaccata ttctaagaaa gcattccgct | 660 |
| aaaaggtgtg gatgtatctg actccggctc cagagactgc tgtgtattgc attcctgcta | 720 |
| cagtgcaaag aaagggacca aggttcccag gaaatgtttg cccagaatgg aagatgagga | 780 |
| ccaaggaggc ggaggaggag gaagaagaag aggaggagga ggaggaggag gaggaggagg | 840 |
| aggaaggcag ccatcatggg agcctggtag agggagatcc agctacagac aactggacag | 900 |
| gagagagaga aaacagccct ctggattctc caggatggca gccgatgtca ctagaagctc | 960 |
| agggctgatg ttcctggttg gctattgcca ccatttcagc tgatacagtc caccatcact | 1020 |

```
gattaccggc gcggttgcgg tggatgcact tgaaccaaac cagtgtatct cctgtgattt    1080
gttttcatgt gtccgaagac accagggaaa cagagatcct ggtgttgttc cttgttatta    1140
cgttttactg ctgaaagtaa gaggtttatt tttctgtcac tcagtggaga catacccctgg   1200 aaaggagagg ggaaaaaaaa agcaaagata caagagataa tcacctttgc atttgaaagt    1260
tgaggcccga ggtttactac aaccagcatt tttgccaacg gttggtgatt gatttccatc    1320
acggtgtgtg gggtgggaag aagttggcta ggaaccaaaa aggctgtgct catgattaaa    1380
cacaaacctg aaggtatttc ctttatgtcc ttggaaacag gaaacgagtt gtggttttcg    1440
ccagcattct tgtaggagag aatcggggaa ggccccgaac tgcccccggg cagggagagc    1500
ccctcaggcc tgttggttta cagagagaca gatgttacat aaccagctcc gttgatgcgt    1560
ggtcaccagt gaccagagaa gctactcgat gcaatgcatc tgtttcagat acagaaatat    1620
agagaagata tttattgaaa tttaagttat tgttatttat taccgttcac taatgaattt    1680 ctctttttc ccttatttat taaagtttct tttcaaaggt gccaaagtat atgtgctcgc     1740
aaaatgcaaa gaaaggtgac aaaaggaaat ttgaattggg aacaagggtc catgcttttc    1800
aaagtattaa aaagtttttt gccaggcaaa aatcacttac tttacctttt taagaaaatt    1860
tgtcattaat tttccccaga tttcagcatt tttcccaatt tttatttgtg gagcatctca    1920
ggcaagcccc ctttcctgga gcagcgtgca gagaccactg gcacttgact ttatttcttc    1980
cttgctccat tgctgaacag aaatgtcgtg ggctccactt cctgttgtct ttaagctctt    2040
agtcccctcc acgtatacct atctgtacta tgcataacca tatgtagaaa aggttcagtt    2100
ccttttagta ggtagtcctg gatttaatgc tgacctaaaa gtaatgtcga caatgctgtc    2160
aggtagctgc cgttctaccg actccctcca tccctgccca ccactgccc tcccgagaat     2220 atgctggctg cccagtgcag cccggggagac acaggggcct tccagaggta gggtctacca   2280
ggtcctgtac aaccccctggg ctgtcaccgg gggtcaacag ctgctgctcc tatatacccca  2340 aacacctgac agctccctgg ggagcagatg gctgagaagg gtgctgagga agccatattg    2400
ggaccagcca cagccacaca catggagcct catacttagg agcgtgctgc ctttaaatga    2460
aggtggtcgg ggccagtgca gcggctcaca cccataatcc caacactttg gaaagccaag    2520
gtgggaggat ctcttgaacc caggagtttg agaccagctt gggcaacata gggagaccct    2580
gtctctacag aaactttaaa aattaggcag gcatgatggt gcacacctgt ggtcccagct    2640
actcaagagg ctgaaggagg atcacttgag tccagaaggt cgaggctgca gtgagctgtg    2700
atcatgccac tgcactccag cctaagtgac agtgcggtac cctgtctcaa aaaaaaaaa    2760 aaaaaaaaa agaggttgga gcaggaggaa gcataggggc gggaacagcc acctcctcca    2820
tgccctagat tgtgaattta tcgggcagcc aacacatgta tgacacacta ggccctgtat    2880
tacagcttgt tacgcatttc ataaaaggga ttttcattaa ggagataatc tattactacc    2940
taccttagtg gctactagta taaaactatg acagatttag caattaaatg aaatactggc    3000
ctccatcaaa taatcatagt aacaagaagc agcagttacc agacatctga tcccttccc     3060 ccaaaatacc caaattcttc atggttctgc ccttctctgt cctttctgct ccccttgctc    3120
gcctgggaaa tggaggaaag gccttccctc tcacactgtc ttgggatctt gctgagaatt    3180
cagactgctc gaaacagtga caaaccccag ccatccagtc attcgtggag cacaatttgg    3240
atgtggcccc aggggcatct gtcccattca gagaaccttg gcagtgcgat ggccactgtt    3300
cccaggcttc aacctcagtg accccccca acaactcccc atgagagagtc cctgcccaaa    3360 aaagctgtag gatccaaggg gtgtcaatag ctcgttcccg gcatcaccta cacaccacaa    3420
```

```
gcaggtttta atggaagcaa gttgctccac caaatccaca aaagggtaaa gtttgtgatt    3480
tttctttatc attgcgatca ccatctgata ccgtaaggag tgcacttgtt tggaagttct    3540
gacttctctg atctgtcttg gtcgtttgtg ttataaaacc aaagttctct acagacttta    3600
tttttgtaca atatcatttt gtaacttttt acaaataaaa actcatttct attgc         3655
```

<210> SEQ ID NO 3
<211> LENGTH: 3830
<212> TYPE: DNA
<213> ORGANISM: Homo sapiens
<220> FEATURE:
<221> NAME/KEY: misc_feature
<223> OTHER INFORMATION: Homo sapiens glial cell derived neurotrophic
      factor (GDNF)

<400> SEQUENCE: 3

```
ccaaagcgtc cgagactggg tacagtcgtc caggcgtgac ggggggcgcgg ggagccagtg      60 actcctctgg gaggggaagg gattaggggcc agaatctctc aaaggtgcaa aaatccagtc     120
aagagagggt tttcgggtat accacggagg attaaaactt tcaagacaaa tgcagtcttt     180
gcctaacagc aatggtgccg ccgccggacg ggacttttaag atgaagttat gggatgtcgt     240
ggctgtctgc ctggtgctgc tccacaccgc gtccgccttc ccgctgcccg ccggtaagag     300
gcctcccgag gcgcccgccg aagaccgctc cctcggccgc cgccgcgcgc ccttcgcgct     360
gagcagtgac tcaaatatgc cagaggatta tcctgatcag ttcgatgatg tcatggattt     420
tattcaagcc accattaaaa gactgaaaag gtcaccagat aaacaaatgg cagtgcttcc     480
tagaagagag cggaatcggc aggctgcagc tgccaaccca gagaattcca gaggaaaagg     540
tcggagaggc cagaggggca aaaaccgggg ttgtgtctta actgcaatac atttaaatgt     600
cactgacttg ggtctgggct atgaaaccaa ggaggaactg atttttaggt actgcagcgg     660
ctcttgcgat gcagctgaga caacgtacga caaaatattg aaaaacttat ccagaaatag     720
aaggctggtg agtgacaaag tagggcaggc atgttgcaga cccatcgcct ttgatgatga     780
cctgtcgttt ttagatgata acctggttta ccatattcta agaaagcatt ccgctaaaag     840
gtgtggatgt atctgactcc ggctccagag actgctgtgt attgcattcc tgctacagtg     900
caaagaaagg gaccaaggtt cccaggaaat gtttgcccag aatggaagat gaggaccaag     960
gaggcggagg aggaggaaga agaagaggag gaggaggagg aggaggagga ggaggaggaa    1020
ggcagccatc atgggagcct ggtagaggga gatccagcta cagacaactg gacaggagag    1080
agagaaaaca gccctctgga ttctccagga tggcagccga tgtcactaga agctcagggc    1140
tgatgttcct ggttggctat tgccaccatt tcagctgata cagtccacca tcactgatta    1200
ccggcgcggt tgcggtggat gcacttgaac caaaccagtg tatctcctgt gatttgtttt    1260
catgtgtccg aagacaccag ggaaacagag atcctggtgt tgttccttgt tattacgttt    1320
tactgctgaa agtaagaggt ttatttttct gtcactcagt ggagacatac cctgaaaagg    1380
agagggaaaa aaaaaagcaa agatacaaga gataatcacc tttgcatttg aaagttgagg    1440
cccgaggttt actacaacca gcattttttgc caacggttgg tgattgattt ccatcacggt    1500
gtgtggggtg gaagaagtt ggctaggaac caaaaaggct gtgctcatga ttaaacacaa    1560
acctgaaggt atttcctttta tgtccttgga aacaggaaac gagttgtggt tttcgccagc    1620
attcttgtag gagagaatcg gggaaggccc cgaactgccc ccgggcaggg agagcccctc    1680
aggcctgttg gtttacagag agacagatgt tacataacca gctccgttga tgcgtggtca    1740
```

-continued

```
ccagtgacca gagaagctac tcgatgcaat gcatctgttt cagatacaga aatatagaga      1800
agatatttat tgaaatttaa gttattgtta tttattaccg ttcactaatg aatttctctt      1860
ttttcccta  tttattaaag tttcttttca aggtgccaa  agtatatgtg ctcgcaaaat      1920
gcaaagaaag gtgacaaaag gaaatttgaa ttgggaacaa gggtccatgc ttttcaaagt      1980
attaaaagt  ttttgccag  gcaaaaatca cttactttac cttttaaga  aaatttgtca      2040
ttaatttcc  ccagatttca gcattttcc  caatttttat ttgtggagca tctcaggcaa      2100
gccccctttc ctggagcagc gtgcagagac cactggcact tgactttatt tcttccttgc      2160
tccattgctg aacagaaatg tcgtgggctc cacttcctgt tgtctttaag ctcttagtcc      2220
cctccacgta tacctatctg tactatgcat aaccatatgt agaaaggtt  cagttccttt      2280
tagtaggtag tcctggattt aatgctgacc taaaagtaat gtcgacaatg ctgtcaggta      2340
gctgccgttc taccgactcc ctccatccct gcccacccac tgccctcccg agaatatgct      2400
ggctgcccag tgcagcccgg gagacacagg ggccttccag aggtagggtc taccaggtcc      2460
tgtacaaccc ctgggctgtc accggggtc  aacagctgct gctcctatat acccaaacac      2520
ctgacagctc cctggggagc agatggctga aagggtgct  gaggaagcca tattgggacc      2580
agccacagcc acacacatgg agcctcatac ttaggagcgt gctgccttta aatgaaggtg      2640
gtcgggcca  gtgcagcggc tcacacccat aatcccaaca ctttggaaag ccaaggtggg      2700
aggatctctt gaacccagga gtttgagacc agcttgggca acatagggag accctgtctc      2760
tacagaaact ttaaaaatta ggcaggcatg atggtgcaca cctgtggtcc cagctactca      2820
agaggctgaa ggaggatcac ttgagtccag aaggtcgagg ctgcagtgag ctgtgatcat      2880
gccactgcac tccagcctaa gtgacagtgc ggtaccctgt ctcaaaaaaa aaaaaaaaa      2940
aaaaagagg  ttggagcagg aggaagcata ggggcgggaa cagccacctc ctccatgccc      3000
tagattgtga atttatcggg cagccaacac atgtatgaca cactaggccc tgtattacag      3060
cttgttacgc atttcataaa agggattttc attaaggaga taatctatta ctacctacct      3120
tagtggctac tagtataaaa ctatgacaga tttagcaatt aaatgaaata ctggcctcca      3180
tcaaataatc atagtaacaa gaagcagcag ttaccagaca tctgatcccc ttcccccaaa      3240
atacccaaat tcttcatggt tctgccttc  tctgtccttt ctgctcccct tgctcgcctg      3300
ggaaatggag gaaaggcctt ccctctcaca ctgtcttggg atcttgctga gaattcagac      3360
tgctcgaaac agtgacaaac cccagccatc cagtcattcg tggagcacaa tttggatgtg      3420
gccccagggg catctgtccc attcagagaa ccttggcagt gcgatggcca ctgttcccag      3480
gcttcaacct cagtgacccc ccccaacaac tccccatgga gagtccctgc caaaaaagc      3540
tgtaggatcc aagggtgtc  aatagctcgt tcccggcatc acctacacac cacaagcagg      3600
ttttaatgga agcaagttgc tccaccaaat ccacaaaagg gtaaagtttg tgattttct      3660
ttatcattgc gatcaccatc tgataccgta aggagtgcac ttgtttggaa gttctgactt      3720
ctctgatctg tcttggtcgt ttgtgttata aaaccaaagt tctctacaga ctttatttt      3780
gtacaatatc attttgtaac tttttacaaa taaaaactca tttctattgc                 3830
```

<210> SEQ ID NO 4
<211> LENGTH: 3752
<212> TYPE: DNA
<213> ORGANISM: Homo sapiens
<220> FEATURE:
<221> NAME/KEY: misc_feature
<223> OTHER INFORMATION: Homo sapiens glial cell derived neurotrophic
      factor (GDNF)

<400> SEQUENCE: 4

```
ccaaagcgtc cgagactggg tacagtcgtc caggcgtgac gggggcgcgg ggagccagtg      60
actcctctgg gaggggaagg gattagggcc agaatctctc aaaggtgcaa aaatccagtc     120
aagagagggt tttcgggtat accacggagg attaaaactt tcaagacaaa tgcagtcttt     180
gcctaacagc aatggtgccg ccgccggacg ggactttaag atgaagttat gggatgtcgt     240
ggctgtctgc ctggtgctgc tccacaccgc gtccgccttc ccgctgcccg ccgcaaatat     300
gccagaggat tatcctgatc agttcgatga tgtcatggat tttattcaag ccaccattaa     360
aagactgaaa aggtcaccag ataaacaaat ggcagtgctt cctagaagag agcggaatcg     420
gcaggctgca gctgccaacc cagagaattc cagaggaaaa ggtcggagag ccagaggggg     480
caaaaaccgg ggttgtgtct taactgcaat acatttaaat gtcactgact tgggtctggg     540
ctatgaaacc aaggaggaac tgatttttag gtactgcagc ggctcttgcg atgcagctga     600
gacaacgtac gacaaaatat tgaaaaactt atccagaaat agaaggctgg tgagtgacaa     660
agtagggcag gcatgttgca gacccatcgc ctttgatgat gacctgtcgt ttttagatga     720
taacctggtt taccatattc taagaaagca ttccgctaaa aggtgtggat gtatctgact     780
ccggctccag agactgctgt gtattgcatt cctgctacag tgcaaagaaa gggaccaagg     840
ttcccaggaa atgtttgccc agaatggaag atgaggacca aggaggcgga ggaggaggaa     900
gaagaagagg aggaggagga ggaggaggag gaggaggagg aaggcagcca tcatgggagc     960
ctggtagagg gagatccagc tacagacaac tggacaggag agagagaaaa cagccctctg    1020
gattctccag gatggcagcc gatgtcacta gaagctcagg gctgatgttc ctggttggct    1080
attgccacca tttcagctga tacagtccac catcactgat taccggcgcg gttgcggtgg    1140
atgcacttga accaaaccag tgtatctcct gtgatttgtt ttcatgtgtc cgaagacacc    1200
agggaaacag agatcctggt gttgttcctt gttattacgt tttactgctg aaagtaagag    1260
gtttattttt ctgtcactca gtggagacat accctggaaa ggagagggga aaaaaaaagc    1320
aaagatacaa gagataatca cctttgcatt tgaaagttga ggcccgaggt ttactacaac    1380
cagcattttt gccaacggtt ggtgattgat ttccatcacg gtgtgtgggg tgggaagaag    1440
ttggctagga accaaaaagg ctgtgctcat gattaaacac aaacctgaag gtatttcctt    1500
tatgtccttg gaaacaggaa acgagttgtg gttttcgcca gcattcttgt aggagagaat    1560
cggggaaggc cccgaactgc ccccgggcag ggagagcccc tcaggcctgt tggtttacag    1620
agagacagat gttacataac cagctccgtt gatgcgtggt caccagtgac cagagaagct    1680
actcgatgca atgcatctgt ttcagataca gaaatataga gaagatattt attgaaattt    1740
aagttattgt tatttattac cgttcactaa tgaatttctc ttttttccct tatttattaa    1800
agtttctttt caaaggtgcc aaagtatatg tgctcgcaaa atgcaaagaa aggtgacaaa    1860
aggaaatttg aattgggaac aagggtccat gcttttcaaa gtattaaaaa gttttttgcc    1920
aggcaaaaat cacttacttt accttttttaa gaaaatttgt cattaatttt ccccagattt    1980
cagcattttt cccaattttt atttgtggag catctcaggc aagccccctt tcctggagca    2040
gcgtgcagag accactggca cttgacttta tttcttcctt gctccattgc tgaacagaaa    2100
tgtcgtgggc tccacttcct gttgtcttta agctcttagt cccctccacg tataccctatc    2160
tgtactatgc ataaccatat gtagaaaagg ttcagttcct tttagtaggt agtcctggat    2220
ttaatgctga cctaaaagta atgtcgacaa tgctgtcagg tagctgccgt tctaccgact    2280
```

| | |
|---|---:|
| ccctccatcc ctgcccaccc actgccctcc cgagaatatg ctggctgccc agtgcagccc | 2340 |
| gggagacaca ggggccttcc agaggtaggg tctaccaggt cctgtacaac ccctgggctg | 2400 |
| tcaccggggg tcaacagctg ctgctcctat atacccaaac acctgacagc tccctgggga | 2460 |
| gcagatggct gagaagggtg ctgaggaagc catattggga ccagccacag ccacacacat | 2520 |
| ggagcctcat acttaggagc gtgctgcctt taaatgaagg tggtcggggc cagtgcagcg | 2580 |
| gctcacaccc ataatcccaa cactttggaa agccaaggtg ggaggatctc ttgaacccag | 2640 |
| gagtttgaga ccagcttggg caacataggg agaccctgtc tctacagaaa ctttaaaaat | 2700 |
| taggcaggca tgatggtgca cacctgtggt cccagctact caagaggctg aaggaggatc | 2760 |
| acttgagtcc agaaggtcga ggctgcagtg agctgtgatc atgccactgc actccagcct | 2820 |
| aagtgacagt gcggtaccct gtctcaaaaa aaaaaaaaa aaaaaaaga ggttggagca | 2880 |
| ggaggaagca taggggcggg aacagccacc tcctccatgc cctagattgt gaatttatcg | 2940 |
| ggcagccaac acatgtatga cactaggcc ctgtattac agcttgttac gcatttcata | 3000 |
| aaagggattt tcattaagga gataatctat tactacctac cttagtggct actagtataa | 3060 |
| aactatgaca gatttagcaa ttaaatgaaa tactggcctc catcaaataa tcatagtaac | 3120 |
| aagaagcagc agttaccaga catctgatcc ccttccccca aaatacccaa attcttcatg | 3180 |
| gttctgccct tctctgtcct ttctgctccc cttgctcgcc tgggaaatgg aggaaaggcc | 3240 |
| ttccctctca cactgtcttg ggatcttgct gagaattcag actgctcgaa acagtgacaa | 3300 |
| accccagcca tccagtcatt cgtggagcac aatttggatg tggccccagg gcatctgtc | 3360 |
| ccattcagag aaccttggca gtgcgatggc cactgttccc aggcttcaac ctcagtgacc | 3420 |
| cccccaaca actccccatg gagagtccct gcccaaaaaa gctgtaggat caaggggtg | 3480 |
| tcaatagctc gttcccggca tcacctacac accacaagca ggttttaatg gaagcaagtt | 3540 |
| gctccaccaa atccacaaaa gggtaaagtt tgtgattttt ctttatcatt gcgatcacca | 3600 |
| tctgataccg taaggagtgc acttgtttgg aagttctgac ttctctgatc tgtcttggtc | 3660 |
| gtttgtgtta taaaaccaaa gttctctaca gactttattt ttgtacaata tcatttttgta | 3720 |
| acttttaca aataaaaact catttctatt gc | 3752 |

```
<210> SEQ ID NO 5
<211> LENGTH: 485
<212> TYPE: DNA
<213> ORGANISM: Homo sapiens
<220> FEATURE:
<221> NAME/KEY: misc_feature
<223> OTHER INFORMATION: cDNA encoding isoform 1

<400> SEQUENCE: 5
```

| | |
|---|---:|
| caaatatgcc agaggattat cctgatcagt tcgatgatgt catggatttt attcaagcca | 60 |
| ccattaaaag actgaaaagg tcaccagata acaaatggc agtgcttcct agaagagagc | 120 |
| ggaatcggca ggctgcagct gccaacccag agaattccag aggaaaaggt cggagaggcc | 180 |
| agaggggcaa aaaccggggt tgtgtcttaa ctgcaataca tttaaatgtc actgacttgg | 240 |
| gtctgggcta tgaaaccaag gaggaactga ttttttaggta ctgcagcggc tcttgcgatg | 300 |
| cagctgagac aacgtacgac aaaatattga aaacttatc cagaaataga aggctggtga | 360 |
| gtgacaaagt agggcaggca tgttgcagac ccatcgcctt tgatgatgac ctgtcgtttt | 420 |
| tagatgataa cctggtttac catattctaa gaaagcattc cgctaaaagg tgtggatgta | 480 |
| tctga | 485 |

<210> SEQ ID NO 6
<211> LENGTH: 185
<212> TYPE: PRT
<213> ORGANISM: Homo sapiens
<220> FEATURE:
<221> NAME/KEY: misc_feature
<223> OTHER INFORMATION: glial cell line-derived neurotrophic factor
      isoform 2 preproprotein

<400> SEQUENCE: 6

```
Met Lys Leu Trp Asp Val Val Ala Val Cys Leu Val Leu Leu His Thr
1               5                   10                  15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
        35                  40                  45

Leu Lys Arg Ser Pro Asp Lys Gln Met Ala Val Leu Pro Arg Arg Glu
    50                  55                  60

Arg Asn Arg Gln Ala Ala Ala Ala Asn Pro Glu Asn Ser Arg Gly Lys
65                  70                  75                  80

Gly Arg Arg Gly Gln Arg Gly Lys Asn Arg Gly Cys Val Leu Thr Ala
                85                  90                  95

Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
        115                 120                 125

Thr Tyr Asp Lys Ile Leu Lys Asn Leu Ser Arg Asn Arg Arg Leu Val
    130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
            180                 185
```

<210> SEQ ID NO 7
<211> LENGTH: 211
<212> TYPE: PRT
<213> ORGANISM: Homo sapiens
<220> FEATURE:
<221> NAME/KEY: misc_feature
<223> OTHER INFORMATION: glial cell line-derived neurotrophic factor
      isoform 1 preproprotein

<400> SEQUENCE: 7

```
Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
```

-continued

```
                100             105             110
Gly Lys Asn Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210

<210> SEQ ID NO 8
<211> LENGTH: 228
<212> TYPE: PRT
<213> ORGANISM: Homo sapiens
<220> FEATURE:
<221> NAME/KEY: misc_feature
<223> OTHER INFORMATION: glial cell line-derived neurotrophic factor
      isoform 3 preproprotein

<400> SEQUENCE: 8

Met Gln Ser Leu Pro Asn Ser Asn Gly Ala Ala Gly Arg Asp Phe
1               5                   10                  15

Lys Met Lys Leu Trp Asp Val Val Ala Val Cys Leu Val Leu Leu His
                20                  25                  30

Thr Ala Ser Ala Phe Pro Leu Pro Ala Gly Lys Arg Pro Pro Glu Ala
            35                  40                  45

Pro Ala Glu Asp Arg Ser Leu Gly Arg Arg Arg Ala Pro Phe Ala Leu
    50                  55                  60

Ser Ser Asp Ser Asn Met Pro Glu Asp Tyr Pro Asp Gln Phe Asp Asp
65                  70                  75                  80

Val Met Asp Phe Ile Gln Ala Thr Ile Lys Arg Leu Lys Arg Ser Pro
                85                  90                  95

Asp Lys Gln Met Ala Val Leu Pro Arg Arg Glu Arg Asn Arg Gln Ala
            100                 105                 110

Ala Ala Ala Asn Pro Glu Asn Ser Arg Gly Lys Gly Arg Arg Gly Gln
            115                 120                 125

Arg Gly Lys Asn Arg Gly Cys Val Leu Thr Ala Ile His Leu Asn Val
    130                 135                 140

Thr Asp Leu Gly Leu Gly Tyr Glu Thr Lys Glu Glu Leu Ile Phe Arg
145                 150                 155                 160

Tyr Cys Ser Gly Ser Cys Asp Ala Ala Glu Thr Thr Tyr Asp Lys Ile
                165                 170                 175

Leu Lys Asn Leu Ser Arg Asn Arg Arg Leu Val Ser Asp Lys Val Gly
            180                 185                 190

Gln Ala Cys Cys Arg Pro Ile Ala Phe Asp Asp Asp Leu Ser Phe Leu
        195                 200                 205

Asp Asp Asn Leu Val Tyr His Ile Leu Arg Lys His Ser Ala Lys Arg
    210                 215                 220

Cys Gly Cys Ile
225
```

<210> SEQ ID NO 9
<211> LENGTH: 202
<212> TYPE: PRT
<213> ORGANISM: Homo sapiens
<220> FEATURE:
<221> NAME/KEY: misc_feature
<223> OTHER INFORMATION: glial cell line-derived neurotrophic factor
      isoform 4 preproprotein

<400> SEQUENCE: 9

Met Gln Ser Leu Pro Asn Ser Asn Gly Ala Ala Ala Gly Arg Asp Phe
1               5                   10                  15

Lys Met Lys Leu Trp Asp Val Val Ala Val Cys Leu Val Leu Leu His
            20                  25                  30

Thr Ala Ser Ala Phe Pro Leu Pro Ala Ala Asn Met Pro Glu Asp Tyr
        35                  40                  45

Pro Asp Gln Phe Asp Asp Val Met Asp Phe Ile Gln Ala Thr Ile Lys
    50                  55                  60

Arg Leu Lys Arg Ser Pro Asp Lys Gln Met Ala Val Leu Pro Arg Arg
65                  70                  75                  80

Glu Arg Asn Arg Gln Ala Ala Ala Asn Pro Glu Asn Ser Arg Gly
                85                  90                  95

Lys Gly Arg Arg Gly Gln Arg Gly Lys Asn Arg Gly Cys Val Leu Thr
            100                 105                 110

Ala Ile His Leu Asn Val Thr Asp Leu Gly Leu Gly Tyr Glu Thr Lys
        115                 120                 125

Glu Glu Leu Ile Phe Arg Tyr Cys Ser Gly Ser Cys Asp Ala Ala Glu
    130                 135                 140

Thr Thr Tyr Asp Lys Ile Leu Lys Asn Leu Ser Arg Asn Arg Arg Leu
145                 150                 155                 160

Val Ser Asp Lys Val Gly Gln Ala Cys Cys Arg Pro Ile Ala Phe Asp
                165                 170                 175

Asp Asp Leu Ser Phe Leu Asp Asp Asn Leu Val Tyr His Ile Leu Arg
            180                 185                 190

Lys His Ser Ala Lys Arg Cys Gly Cys Ile
        195                 200

<210> SEQ ID NO 10
<211> LENGTH: 211
<212> TYPE: PRT
<213> ORGANISM: Mouse sp.
<220> FEATURE:
<221> NAME/KEY: misc_feature
<223> OTHER INFORMATION: mouse GDN sequence

<400> SEQUENCE: 10

Met Lys Leu Trp Asp Val Val Ala Val Cys Leu Val Leu Leu His Thr
1               5                   10                  15

Ala Ser Ala Phe Pro Leu Pro Ala Gly Lys Arg Leu Leu Glu Ala Pro
            20                  25                  30

Ala Glu Asp His Ser Leu Gly His Arg Arg Val Pro Phe Ala Leu Thr
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Ala Ala Ala Leu Pro Arg Arg Glu Arg Asn Arg Gln Ala Ala

```
                85                  90                  95
Ala Ala Ser Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
            130                 135                 140

Cys Ser Gly Ser Cys Glu Ser Ala Glu Thr Met Tyr Asp Lys Ile Leu
145                 150                 155                 160

Lys Asn Leu Ser Arg Ser Arg Arg Leu Thr Ser Asp Lys Val Gly Gln
                165                 170                 175

Ala Cys Cys Arg Pro Val Ala Phe Asp Asp Asp Leu Ser Phe Leu Asp
            180                 185                 190

Asp Asn Leu Val Tyr His Ile Leu Arg Lys His Ser Ala Lys Arg Cys
            195                 200                 205

Gly Cys Ile
        210

<210> SEQ ID NO 11
<211> LENGTH: 211
<212> TYPE: PRT
<213> ORGANISM: Rat sp.
<220> FEATURE:
<221> NAME/KEY: misc_feature
<223> OTHER INFORMATION: Rat GDN sequence

<400> SEQUENCE: 11

Met Lys Leu Trp Asp Val Val Ala Val Cys Leu Val Leu Leu His Thr
1               5                   10                  15

Ala Ser Ala Phe Pro Leu Pro Ala Gly Lys Arg Leu Leu Glu Ala Pro
            20                  25                  30

Ala Glu Asp His Ser Leu Gly His Arg Arg Val Pro Phe Ala Leu Thr
            35                  40                  45

Ser Asp Ser Asn Met Pro Glu Asp Tyr Pro Asp Gln Phe Asp Asp Val
50                  55                  60

Met Asp Phe Ile Gln Ala Thr Ile Lys Arg Leu Lys Arg Ser Pro Asp
65                  70                  75                  80

Lys Gln Ala Ala Ala Leu Pro Arg Arg Glu Arg Asn Arg Gln Ala Ala
            85                  90                  95

Ala Ala Ser Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
            130                 135                 140

Cys Ser Gly Ser Cys Glu Ala Ala Glu Thr Met Tyr Asp Lys Ile Leu
145                 150                 155                 160

Lys Asn Leu Ser Arg Ser Arg Arg Leu Thr Ser Asp Lys Val Gly Gln
                165                 170                 175

Ala Cys Cys Arg Pro Val Ala Phe Asp Asp Asp Leu Trp Phe Leu Asp
            180                 185                 190

Asp Ser Leu Val Tyr His Ile Leu Arg Lys His Ser Ala Lys Arg Cys
            195                 200                 205

Gly Cys Ile
        210
```

<210> SEQ ID NO 12
<211> LENGTH: 196
<212> TYPE: PRT
<213> ORGANISM: Artificial Sequence
<220> FEATURE:
<223> OTHER INFORMATION: Consensus sequence derived from human and mouse
     GDN sequences

<400> SEQUENCE: 12

Met Lys Leu Trp Asp Val Val Ala Val Cys Leu Val Leu Leu His Thr
1               5                   10                  15

Ala Ser Ala Phe Pro Leu Pro Ala Gly Lys Arg Glu Ala Pro Ala Glu
            20                  25                  30

Asp Ser Leu Gly Arg Arg Pro Phe Ala Leu Ser Asp Ser Asn Met Pro
        35                  40                  45

Glu Asp Tyr Pro Asp Gln Phe Asp Asp Val Met Asp Phe Ile Gln Ala
    50                  55                  60

Thr Ile Lys Arg Leu Lys Arg Ser Pro Asp Lys Gln Ala Leu Pro Arg
65                  70                  75                  80

Arg Glu Arg Asn Arg Gln Ala Ala Ala Pro Glu Asn Ser Arg Gly
                85                  90                  95

Lys Gly Arg Arg Gly Gln Arg Gly Lys Asn Arg Gly Cys Val Leu Thr
            100                 105                 110

Ala Ile His Leu Asn Val Thr Asp Leu Gly Leu Gly Tyr Glu Thr Lys
        115                 120                 125

Glu Glu Leu Ile Phe Arg Tyr Cys Ser Gly Ser Cys Ala Glu Thr Tyr
    130                 135                 140

Asp Lys Ile Leu Lys Asn Leu Ser Arg Arg Leu Ser Asp Lys Val
145                 150                 155                 160

Gly Gln Ala Cys Cys Arg Pro Ala Phe Asp Asp Leu Ser Phe Leu
                165                 170                 175

Asp Asp Asn Leu Val Tyr His Ile Leu Arg Lys His Ser Ala Lys Arg
            180                 185                 190

Cys Gly Cys Ile
        195

<210> SEQ ID NO 13
<211> LENGTH: 195
<212> TYPE: PRT
<213> ORGANISM: Artificial Sequence
<220> FEATURE:
<223> OTHER INFORMATION: Consensus sequence derived from human and rat
     GDN sequences

<400> SEQUENCE: 13

Met Lys Leu Trp Asp Val Val Ala Val Cys Leu Val Leu Leu His Thr
1               5                   10                  15

Ala Ser Ala Phe Pro Leu Pro Ala Gly Lys Arg Glu Ala Pro Ala Glu
            20                  25                  30

Asp Ser Leu Gly Arg Arg Pro Phe Ala Leu Ser Asp Ser Asn Met Pro
        35                  40                  45

Glu Asp Tyr Pro Asp Gln Phe Asp Asp Val Met Asp Phe Ile Gln Ala
    50                  55                  60

Thr Ile Lys Arg Leu Lys Arg Ser Pro Asp Lys Gln Ala Leu Pro Arg
65                  70                  75                  80

Arg Glu Arg Asn Arg Gln Ala Ala Ala Pro Glu Asn Ser Arg Gly
                85                  90                  95

```
Lys Gly Arg Arg Gly Gln Arg Gly Lys Asn Arg Gly Cys Val Leu Thr
            100                 105                 110

Ala Ile His Leu Asn Val Thr Asp Leu Gly Leu Gly Tyr Glu Thr Lys
        115                 120                 125

Glu Glu Leu Ile Phe Arg Tyr Cys Ser Gly Ser Cys Ala Ala Glu Thr
    130                 135                 140

Tyr Asp Lys Ile Leu Lys Asn Leu Ser Arg Arg Arg Leu Ser Asp Lys
145                 150                 155                 160

Val Gly Gln Ala Cys Cys Arg Pro Ala Phe Asp Asp Leu Phe Leu
                165                 170                 175

Asp Asp Leu Val Tyr His Ile Leu Arg Lys His Ser Ala Lys Arg Cys
            180                 185                 190

Gly Cys Ile
        195

<210> SEQ ID NO 14
<211> LENGTH: 24
<212> TYPE: DNA
<213> ORGANISM: Artificial Sequence
<220> FEATURE:
<223> OTHER INFORMATION: Synthetic primer: Fgfr2-Forward

<400> SEQUENCE: 14
ctctctacgt catagttgaa tatg                                          24

<210> SEQ ID NO 15
<211> LENGTH: 24
<212> TYPE: DNA
<213> ORGANISM: Artificial Sequence
<220> FEATURE:
<223> OTHER INFORMATION: Synthetic primer: Fgfr2-Reverse

<400> SEQUENCE: 15
atatccctgg ccaggccaaa gtct                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic primer: Ret-Forward

<400> SEQUENCE: 16
agatgtttat gaggaagatt ccta                                          24

<210> SEQ ID NO 17
<211> LENGTH: 24
<212> TYPE: DNA
<213> ORGANISM: Artificial Sequence
<220> FEATURE:
<223> OTHER INFORMATION: Synthetic primer: Ret-Reverse

<400> SEQUENCE: 17
tcctcgctgc agttgtctgg cctc                                          24

<210> SEQ ID NO 18
<211> LENGTH: 20
<212> TYPE: DNA
<213> ORGANISM: Artificial Sequence
<220> FEATURE:
<223> OTHER INFORMATION: Synthetic primer: Col4a1-Forward

<400> SEQUENCE: 18
```

-continued atgccctttc tcttctgcaa                                         20

<210> SEQ ID NO 19
<211> LENGTH: 24
<212> TYPE: DNA
<213> ORGANISM: Artificial Sequence
<220> FEATURE:
<223> OTHER INFORMATION: Synthetic primer: Csf1-Forward

<400> SEQUENCE: 19
gatccctgag tctgtcttcc acct                                    24

<210> SEQ ID NO 20
<211> LENGTH: 25
<212> TYPE: DNA
<213> ORGANISM: Artificial Sequence
<220> FEATURE:
<223> OTHER INFORMATION: Synthetic primer: Csf1-Reverse

<400> SEQUENCE: 20
cagttccacc tgtctgtcct catcc                                   25

<210> SEQ ID NO 21
<211> LENGTH: 24
<212> TYPE: DNA
<213> ORGANISM: Artificial Sequence
<220> FEATURE:
<223> OTHER INFORMATION: Synthetic primer: Csf1r-Forward

<400> SEQUENCE: 21
gtaaagtgga tggccccaga gagc                                    24

<210> SEQ ID NO 22
<211> LENGTH: 25
<212> TYPE: DNA
<213> ORGANISM: Artificial Sequence
<220> FEATURE:
<223> OTHER INFORMATION: Synthetic primer: Csf1r-Reverse

<400> SEQUENCE: 22
taggctccag gtcccagcag gactg                                   25

<210> SEQ ID NO 23
<211> LENGTH: 26
<212> TYPE: DNA
<213> ORGANISM: Artificial Sequence
<220> FEATURE:
<223> OTHER INFORMATION: Synthetic primer: c-Myc-Forward

<400> SEQUENCE: 23
cagctcgccc aaatcctgta cctcgt                                  26

<210> SEQ ID NO 24
<211> LENGTH: 25
<212> TYPE: DNA
<213> ORGANISM: Artificial Sequence
<220> FEATURE:
<223> OTHER INFORMATION: Synthetic primer: c-Myc- Reverse

<400> SEQUENCE: 24
cagacaccac atcaatttct tcctc                                   25

<210> SEQ ID NO 25
<211> LENGTH: 27
<212> TYPE: DNA
<213> ORGANISM: Artificial Sequence

```
<220> FEATURE:
<223> OTHER INFORMATION: Synthetic primer: Notch1 -Forward

<400> SEQUENCE: 25
tgaagaacgg agccaacaag gacatgc                                          27

<210> SEQ ID NO 26
<211> LENGTH: 27
<212> TYPE: DNA
<213> ORGANISM: Artificial Sequence
<220> FEATURE:
<223> OTHER INFORMATION: Synthetic primer: Notch1- Reverse

<400> SEQUENCE: 26
gcaatcggtc catgtgatcc gtgatgt                                          27

<210> SEQ ID NO 27
<211> LENGTH: 20
<212> TYPE: DNA
<213> ORGANISM: Artificial Sequence
<220> FEATURE:
<223> OTHER INFORMATION: Synthetic primer: Col4a1-Reverse

<400> SEQUENCE: 27
ctgcggaatc tgaatggtct                                                  20
```

METHODS FOR PROMOTING WOUND HEALING AND HAIR GROWTH COMPRISING GDNF ADMINISTRATION

RELATED APPLICATIONS

This application is a continuation of U.S. application Ser. No. 16/452,459, filed Jun. 25, 2019, which is a divisional of U.S. application Ser. No. 14/775,386, filed Sep. 11, 2015, which is a national stage filing under 35 U.S.C. § 371 of international application number PCT/US2014/027419, filed Mar. 14, 2014, which was published under PCT Article 21(2) in English and claims the benefit of U.S. Provisional Patent Application Ser. No. 61/787,870, filed Mar. 15, 2013, each of which is incorporated by reference herein in its entirety.

BACKGROUND OF THE INVENTION

Adult organisms contain several types of cells with remarkable regenerative potential when provided with appropriate chemical or physical stimuli. Wound healing or wound repair is an example of a system where multiple biological pathways are activated during the regeneration of the entire tissue. Skin, the largest organ of the body self-renews throughout adult life. Hair follicles, described as the "bone marrow of the skin", are a source of numerous growth factors, cytokines and hormones that helps in remodeling the cutaneous environment (Schmidt-Ullrich and Paus (2005), BioEssays 27, 247-261). The role of several growth factors have been reported in the initiation of hair follicle development at embryonic stage but not much is known about their development in adult animals. The role of growth factors in skin biology, in particular, in wound repair or wound healing, has also been reported. However, the exact role of certain growth factors and cytokines in complex processes such as wound repair or wound healing and hair growth remains to be elucidated. Such understanding would greatly facilitate the development of such growth factors and cytokines as pharmaceutical and/or therapeutic agents useful in these complex processes.

SUMMARY OF THE INVENTION

The present invention is based, at least in part, on the discovery that the cytokine, glial cell line-derived growth factor (GDNF) plays unique roles in the complex processes of wound repair and hair growth. Accordingly, the present invention relates to various pharmaceutical and/or therapeutic methods that feature, in common, administration or delivery of glial cell line-derived growth factor (GDNF) as a biologic active agent. The invention is based, at least in part, on the discovery of several important biological activities of GDNF. In particular, the present inventors have discovered significant regulatory roles for GDNF in biological processes including wound healing and hair growth. Accordingly, in one aspect, the invention relates to methods of promoting wound healing, in particular cutaneous wound healing, wherein said methods feature administration of GDNF, or a biologically active fragment thereof, to a wound site of a subject, e.g., a human subject, in a dose and/or for a time period sufficient to promote wound healing. In particular, the GDNF, or biologically active fragment thereof, is administered in a dose and/or for a time sufficient to promote filling and re-epithelialization of a wound site. In a related aspect, the GDNF, or biologically active fragment thereof, is administered in a dose and/or for a time sufficient to promote reestablishment of a skin barrier at the wound site. In another aspect, the invention relates to methods of promoting hair growth on a subject, wherein said methods feature administration of GDNF, or a biologically active fragment thereof, at site of desired hair growth, in a dose and/or for a time sufficient to promote hair growth on the subject. In another aspect, the invention features pharmaceutical formulations that include a therapeutically effective dose of isolated GDNF, or a biologically active fragment thereof. In yet another aspect, the invention features kits that include said pharmaceutical formulations. In yet another aspect, the invention features the use of a therapeutically effective dose of GDNF, or a biologically active fragment thereof, for promoting wound healing at a wound site in a subject. In yet another aspect, the invention features the use of a pharmaceutically effective dose of GDNF, or a biologically active fragment thereof, for promoting hair growth at a desired site in a subject.

DETAILED DESCRIPTION OF THE INVENTION

Figure 1:
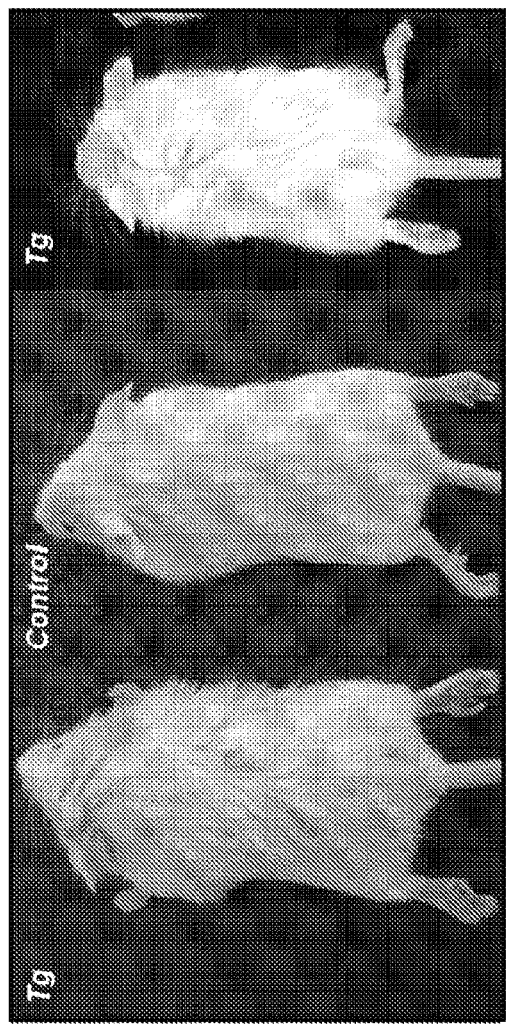
FIG. 1. Mice overexpressing Gdnf under the Cathespin L gene promoter have altered hair follicle development. FVB transgenic mice Tg(Ctsl-Gdnf) have ruffled fur by 3 wk of age (A). Skin sections stained with H&E from adult transgenic FVB mouse with more number of hair follicles adjacent to normal hair development (asterisk) compared to skin section from control littermate (B). The transgene overexpressing GDNF in B6C3H background mice also show multiple layers of hair follicles (C). Scale=100 μtn.
Figure 1:
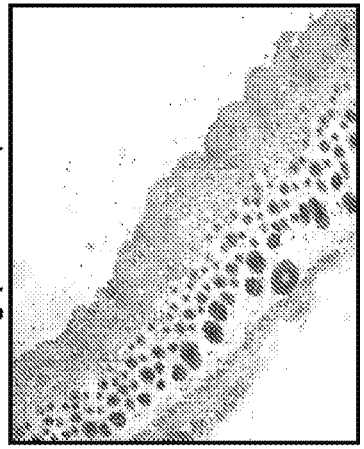
Figure 1:
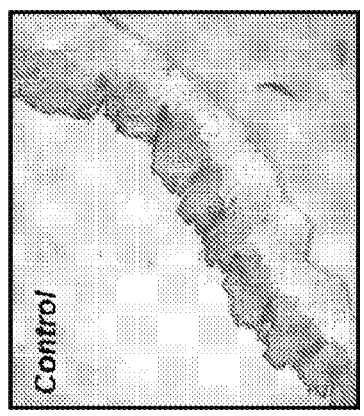
Figure 1:
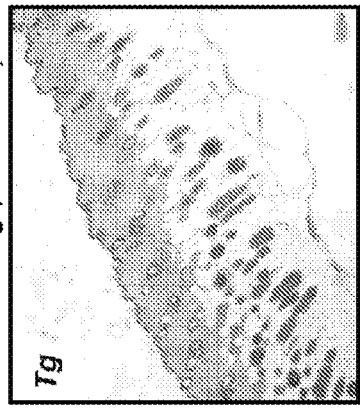
Figure 2:
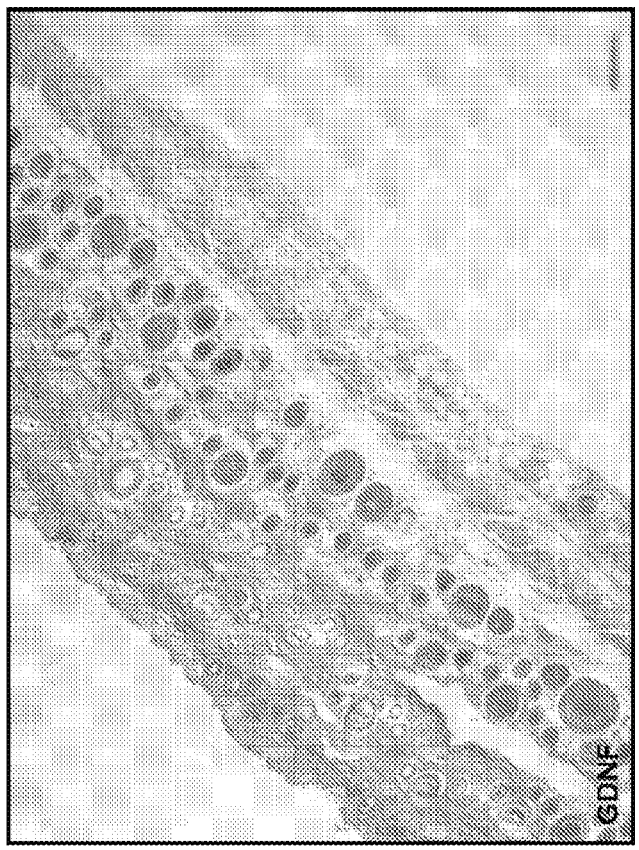
FIG. 2. Subcutaneous injection of recombinant GDNF in adult mice results in an increase in hair follicles. Images of skin sections from B6 wild type mice injected with 100 μï PBS or 10 jag GDNF on alternate days for two weeks. Scale=100 μtn.
Figure 2:
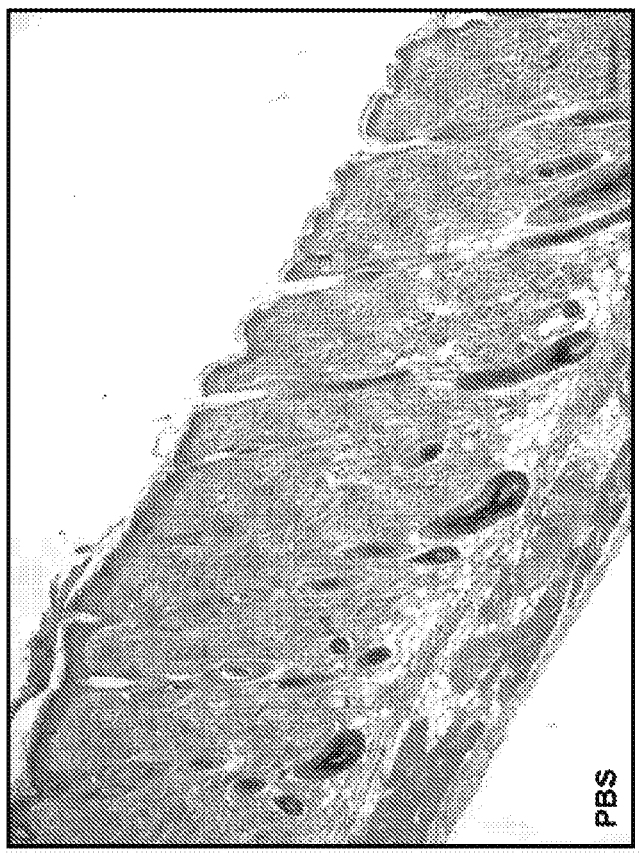

Glial Cell-Derived Neurotrophic Factor (GDNF) is a growth factor with 40% sequence homology to the TGFβ superfamily. First identified as survival factor for dopaminergic neurons of mid-brain and shown to be important for the development and maintenance of neural and other tissues (Lin et al 1993, Science 260, 1130-2). GDNF is part of complex that include the high affinity receptor tyrosine kinase, c-RET and glycosyphatidylinositol (GPI-) linked co-receptor, GFRcc1 that activates specific signaling pathway leading to cell proliferation, survival, and other differentiation effects.

The present invention is based, at least in part, on the discovery of certain key regulatory roles for GDNF in complex processes including wound healing and hair growth. In initial experiments, the effect of GDNF on hair follicle growth was studied. For these studies, purified active recombinant protein expressed in baculovirus (as mammalian proteins expressed in baculovirus are glycosylated) was injected subcutaneously in mice and assayed for hair follicle growth. Preliminary results showed increase in number of hair follicles in mice injected with active form of GDNF compared to mice injected with PBS alone. This finding was very surprising, especially as the effect could be seen after a single injection.

The cutaneous wound healing process involves four steps, first the inflammatory phase followed by proliferative phase, the remodeling step and finally the epithelialization, when new skin is formed. During the proliferative phase extracellular matrix (ECM) components are synthesized and new blood vessels are formed on the matrix. Genes involved in the inflammatory response, angiogenesis and response to wounding were differentially expressed in tissues overexpressing Gdnf. Moreover, when GDNF was injected subcutaneously into mice, smoother skin was discovered. It was therefore predicted that GDNF influences the skin remodeling during wound healing. These findings, in addition to the detailed studies presented in the Examples Section, infra., lead the inventors to propose GDNF as novel factor for hair growth, wound healing, and treatment of scars, wrinkles (anti-aging), in particular, when the GDNF is applied topically to skin.

Prior to describing the invention, it may be helpful to an understanding thereof to set forth definitions of certain terms to be used hereinafter.

I. Definitions

The terms "homolog," "paralog," and "ortholog," have their art recognized meanings. Typically, a homolog of a given gene product is one of functional similarity as well as sequence similarity. If the homolog is derived from a different organism, the homolog may be referred to as the ortholog. If several homologs exist in a given organism, the homolog may be referred to as a paralog. Typically, the sequence similarity/identity between homologs is at least about 40%, 50%, 60%, 70%, 80%, 90%, or more (or a percentage falling within any interval or range of the foregoing). Methods for determining such similarity/identity are described, infra. Domains {e.g., TGFP-like domains) conserved between homologs can have a sequence similarity/identity of at least about 70%, 80%, 90%, or more. It is understood that when comparing gene product sequence between diverse organisms, for example, flies and humans, sequence similarity between given homologs {e.g., orthologs) across the entire protein sequence may be low. However, if functional complementarity exists, and in addition, if conserved domains exist, e.g., TGFP-like domains, then the gene products being compared can be considered homologs and thus selected as compositions for use in the methods of the invention, as described herein.

The term "bioactive fragment" includes any portion {e.g., a segment of contiguous amino acids) of a polypeptide, e.g., a GDNF polypeptide or ortholog thereof, sufficient to exhibit or exert at least activity of the polypeptide, e.g., at least one GDNF-associated activity including, for example, a growth promoting activity.

The phrase "encodes a gene product" includes the generation of a RNA molecule from a DNA molecule {i.e., a complementary RNA molecule generated from the DNA molecule by the process of transcription) and/or the generation of a polypeptide or protein molecule from an RNA {i.e., by the processes of transcription and translation).

The term "expression" of a gene or nucleic acid encompasses not only cellular gene expression, but also the transcription and translation of nucleic acid(s) in cloning systems and in any other context.

The term "subject", as used herein, includes living organisms. Examples of subjects include humans, monkeys, cows, sheep, goats, horses, camels, dogs, cats, mice, rats, and transgenic species thereof. Administration of the compositions of the present invention to a subject to be treated can be carried out using known procedures, at dosages and for periods of time effective to modulate hair growth and/or wound healing in the subject as further described herein.

As used herein, the term "isolated" molecule (e.g., isolated protein molecule or isolated peptide) refers to molecules which are substantially free of other cellular material, or culture medium when produced by recombinant techniques, or substantially free of chemical precursors or other chemicals when chemically synthesized.

The term "treatment", as used herein, is defined as the application or administration of a therapeutic agent to a subject, or application or administration of a therapeutic agent to an isolated tissue or cell line from a subject, who has a disease or disorder, a symptom of a disease or disorder, or a predisposition toward a disease or disorder, with the purpose to cure, heal, alleviate, relieve, alter, remedy, ameliorate, improve or affect the disease or disorder, the symptoms of the disease or disorder, or the predisposition toward a disease or disorder. A therapeutic agent includes, but is not limited to, GDNF peptides, proteins, protein fragments, peptidomimetics, and the like.

The term "effective amount", as used herein, is defined as that amount necessary or sufficient to treat or prevent a disorder. The "effective amount" can vary depending on such factors as the size and weight of the subject, the type of illness, or the particular agent being administered. One of ordinary skill in the art would be able to study the aforementioned factors and make the determination regarding the effective amount of the agent without undue experimentation.

The term "pharmaceutical composition" as used herein, refers to an agent formulated with one or more compatible solid or liquid filler diluents or encapsulating substances, which are suitable for administration to a human or lower animal.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques. Typically, the treatment compositions of the present invention are administered topically or by subcutaneous injection.

A "suitable control" or "appropriate control" refers to any control or standard familiar to one of ordinary skill in the art useful for comparison purposes.

The term "cell" refers to any cell of a biological organism. Preferred cells are eukaryotic cells, including but not limited to, animal cells (e.g., mammalian cells, e.g., human or murine cells), nematode cells, plant cells, and yeast. The term includes cell lines, e.g., transformed mammalian cell lines as well as embryonic cells, e.g., embryonic stem cells. Eukaryotic cells responsive to GDNF, or eukaryotic cells involved in hair growth and/or wound repair are preferred cells of the invention. Also contemplated for use in the invention are prokaryotic cells, for use, for example, in methods of manufacturing proteins, e.g., GDNF.

The term "tissue" refers to a collection of cells, usually of different cell types, organized in a manner that imparts complex biological activity.

The term "cell extract" refers to a lysate or acellular preparation of a cell as defined above and can be a crude extract or partially purified as well as comprise additional agents such as recombinant polypeptides, nucleic acids, and/or buffers or stabilizers.

The term "organism" refers to multicellular organisms such as, e.g., *C. elegans, Drosophila*, mouse, and human.

The terms used herein are not intended to be limiting of the invention.

II. Glial Cell Line-Derived Neurotrophic Factor (GDNF)

Glial cell line-derived neurotrophic factor (or glial cell-derived neurotrophic factor) (GDNF), also known as ATF1, ATF2, HSCR3, and HFB1-GDNF is a distant member of the TGF-β superfamily. Glial-cell-line-derived neurotrophic factor (GDNF) was originally identified as a survival factor for midbrain dopaminergic neurons, and was able to prevent apoptosis of motor neurons induced by axotomy. GDNF and related ligands, neurturin (NRTN), artemin (ARTN) and persephin (PSPN), maintain several neuronal populations in the central nervous systems, including midbrain dopamine neurons and motorneurons. In addition, GDNF, NRTN and ARTN support the survival and regulate the differentiation of many peripheral neurons, including sympathetic, parasympathetic, sensory and enteric neurons. GDNF has further critical roles outside the nervous system in the regulation of kidney morphogenesis and spermatogenesis.

GDNF family ligands bind to specific GDNF family receptor alpha (GFRalpha) proteins, all of which form receptor complexes and signal through the RET receptor tyrosine kinase (the product of the c-ret (rearranged during transfection) protooncogene). The biological activity of GDNF is mediated by its corresponding high affinity receptor, GDNF family receptor a-1 (GFRa-1) which functions as part of a receptor complex with the intracellular-signaling component, RET. The mature form of the protein is considered a ligand for RET. GDNF also shows lower-affinity interactions with GFRa-2. The biology of GDNF signaling is much more complex than originally assumed. The neurotrophic effect of GDNF, except in motorneurons, requires the presence of TGF-β, which activates the transport of GFRa1 to the cell membrane. GDNF can also signal RET independently through GFR1a. Upon ligand binding, GDNF in complex with GFRa1 may interact with heparan sulphate glycosaminoglycans to activate the Met receptor tyrosine kinase through cytoplasmic Src-family kinases. GDNF family ligands also signal through the neural cell adhesion molecule NCAM. In cells lacking RET, GDNF binds with high affinity to the NCAM and GFRa1 complex, which activates Fyn and FAK.

This GDNF gene encodes a highly conserved neurotrophic factor. The encoded protein is processed to a mature secreted form that exists as a homodimer. Multiple transcript variants encoding different isoforms have been found for the human GDNF gene. Transcript variant (1) differs in the 5' UTR, representing use of an alternate promoter, and a downstream start codon, compared to variant 3. The resulting isoform (1) has a shorter N-terminus, compared to isoform 3. Transcript variant (2) also differs in the UTR, and represents use of an alternate promoter, uses a downstream start codon, and uses an alternate in-frame splice site in the coding region, compared to variant 3. The resulting isoform (2) has a shorter N-terminus and lacks an internal segment, compared to isoform 3. Transcript variant (3) represents the longest transcript and encodes the longest isoform (3). Transcript Variant: This variant (4) uses an alternate in-frame splice site in the coding region, compared to variant 3. The resulting isoform (4) lacks an internal segment, compared to isoform 3.

The nucleic acids encoding the human GDNF isoforms are as follows:

```
>gi |299473777 |ref |NM_000514.3| Homo sapiens glial cell derived
neurotrophic factor (GDNF) , transcript variant 1, mRNA
                                                         (SEQ ID NO: 1)
CCGCCTCCAGCGCGCCCTTGCTGCCCCGCGCGACCCCAGGATTGCGAACTCTTGCCCCTGACCTGTTGGG

CGGGGCTCCGCGCTCCAGCCATCAGCCCGGATGGGTCTCCTGGCTGGGACTTGGGGCACCTGGAGTTAAT
```

-continued

```
GTCCAACCTAGGGTCTGCGGAGACCCGATCCGAGGTGCCGCCGCCGGACGGGACTTTAAGATGAAGTTAT
GGGATGTCGTGGCTGTCTGCCTGGTGCTGCTCCACACCGCGTCCGCCTTCCCGCTGCCCGCCGGTAAGAG
GCCTCCCGAGGCGCCCGCCGAAGACCGCTCCCTCGGCCGCCGCCGCGCGCCCTTCGCGCTGAGCAGTGAC
TCAAATATGCCAGAGGATTATCCTGATCAGTTCGATGATGTCATGGATTTTATTCAAGCCACCATTAAAA
GACTGAAAAGGTCACCAGATAAACAAATGGCAGTGCTTCCTAGAAGAGAGCGGAATCGGCAGGCTGCAGC
TGCCAACCCAGAGAATTCCAGAGGAAAAGGTCGGAGAGGCCAGAGGGGCAAAAACCGGGGTTGTGTCTTA
ACTGCAATACATTTAAATGTCACTGACTTGGGTCTGGGCTATGAAACCAAGGAGGAACTGATTTTTAGGT
ACTGCAGCGGCTCTTGCGATGCAGCTGAGACAACGTACGACAAAATATTGAAAAACTTATCCAGAAATAG
AAGGCTGGTGAGTGACAAAGTAGGGCAGGCATGTTGCAGACCCATCGCCTTTGATGATGACCTGTCGTTT
TTAGATGATAACCTGGTTTACCATATTCTAAGAAAGCATTCCGCTAAAAGGTGTGGATGTATCTGACTCC
GGCTCCAGAGACTGCTGTGTATTGCATTCCTGCTACAGTGCAAAGAAAGGGACCAAGGTTCCCAGGAAAT
GTTTGCCCAGAA TGGAAG A TGAGGA CCAAG GAGGCGGAGGAGGAG GAAGAAGAAG AGGAGGAGGAGGAGG
AGGAGGAGGAGGAGGAGGAAGGCAGCCATCATGGGAGCCTGGTAGAGGGAGATCCAGCTACAGACAACTG
GACAGGAGAGAGAGAAAACAGCCCTCTGGATTCTCCAGGATGGCAGCCGATGTCACTAGAAGCTCAGGGC
TGATGTTCCTGGTTGGCTATTGCCACCATTTCAGCTGATACAGTCCACCATCACTGATTACCGGCGCGGT
TGCGGTGGATGCACTTGAACCAAACCAGTGTATCTCCTGTGATTTGTTTTCATGTGTCCGAAGACACCAG
GGAAACAGAGATCCTGGTGTTGTTCCTTGTTATTACGTTTTACTGCTGAAAGTAAGAGGTTTATTTTTCT
GTCACTCAGTGGAGACATACCCTGGAAAGGAGAGGGGAAAAAAAAAGCAAAGATACAAGAGATAATCACC
TTTGCATTTGAAAGTTGAGGCCCGAGGTTTACTACAACCAGCATTTTTGCCAACGGTTGGTGATTGATTT
CCATCACGGTGTGTGGGGTGGGAAGAAGTTGGCTAGGAACCAAAAAGGCTGTGCTCATGATTAAACACAA
ACCTGAAGGTATTTCCTTTATGTCCTTGGAAACAGGAAACGAGTTGTGGTTTTCGCCAGCATTCTTGTAG
GAGAGAATCGGGGAAGGCCCCGAACTGCCCCCGGGCAGGGAGAGCCCCTCAGGCCTGTTGGTTTACAGAG
AGACAGATGTTACATAACCAGCTCCGTTGATGCGTGGTCACCAGTGACCAGAGAAGCTACTCGATGCAAT
GCATCTGTTTCAGA TACAGAAAT A TAGAGAAGA TA TTTA TTGAAAT TTAAG TTATTGTTATTTA TTACCG
TTCACTAATGAATTTCTCTTTTTTCCCTTATTTATTAAAGTTTCTTTTCAAAGGTGCCAAAGTATATGTG
CTCGCAAAATGCAAAGAAAGGTGACAAAAGGAAATTTGAATTGGGAACAAGGGTCCATGCTTTTCAAAGT
ATTAAAAAGTTTTTTGCCAGGCAAAAATCACTTACTTTACCTTTTTAAGAAAATTTGTCATTAATTTTCC
CCAGATTTCAGCATTTTTCCCAATTTTTATTTGTGGAGCATCTCAGGCAAGCCCCCTTTCCTGGAGCAGC
GTGCAGAGACCACTGGCACTTGACTTTATTTCTTCCTTGCTCCATTGCTGAACAGAAATGTCGTGGGCTC
CACTTCCTGTTGTCTTTAAGCTCTTAGTCCCCTCCACGTATACCTATCTGTACTATGCATAACCATATGT
AGAAAAGGTTCAGTTCCTTTTAGTAGGTAGTCCTGGATTTAATGCTGACCTAAAAGTAATGTCGACAATG
CTGTCAGGTAGCTGCCGTTCTACCGACTCCCTCCATCCCTGCCCACCCACTGCCCTCCCGAGAATATGCT
GGCTGCCCAGTGCAGCCCGGGAGACACAGGGGCCTTCCAGAGGTAGGGTCTACCAGGTCCTGTACAACCC
CTGGGCTGTCACCGGGGGTCAACAGCTGCTGCTCCTATATACCCAAACACCTGACAGCTCCCTGGGGAGC
AGATGGCTGAGAAGGGTGCTGAGGAAGCCATATTGGGACCAGCCACAGCCACACACATGGAGCCTCATAC
TTAGGAGCGTGCTGCCTTTAAATGAAGGTGGTCGGGGCCAGTGCAGCGGCTCACACCCATAATCCCAACA
CTTTGGAAAGCCAAGGTGGGAGGATCTCTTGAACCCAGGAGTTTGAGACCAGCTTGGGCAACATAGGGAG
ACCCTGTCTCTACAGAAACTTTAAAAATTAGGCAGGCATGATGGTGCACACCTGTGGTCCCAGCTACTCA
AGAGGCTGAAGGAGGATCACTTGAGTCCAGAAGGTCGAGGCTGCAGTGAGCTGTGATCATGCCACTGCAC
TCCAGCCTAAGTGACAGTGCGGTACCCTGTCTCAAAAAAAAAAAAAAAAAAAAAAGAGGTTGGAGCAGG
AGGAAGCATAGGGGCGGGAACAGCCACCTCCTCCATGCCCTAGATTGTGAATTTATCGGGCAGCCAACAC
```

-continued

```
ATGTATGACACACTAGGCCCTGTATTACAGCTTGTTACGCATTTCATAAAAGGGATTTTCATTAAGGAGA

TAATCTATTACTACCTACCTTAGTGGCTACTAGTATAAAACTATGACAGATTTAGCAATTAAATGAAATA

CTGGCCTCCATCAAATAATCATAGTAACAAGAAGCAGCAGTTACCAGACATCTGATCCCCTTCCCCCAAA

ATACCCAAATTCTTCATGGTTCTGCCCTTCTCTGTCCTTTCTGCTCCCCTTGCTCGCCTGGGAAATGGAG

GAAAGGCCTTCCCTCTCACACTGTCTTGGGATCTTGCTGAGAATTCAGACTGCTCGAAACAGTGACAAAC

CCCAGCCATCCAGTCATTCGTGGAGCACAATTTGGATGTGGCCCCAGGGGCATCTGTCCCATTCAGAGAA

CCTTGGCAGTGCGATGGCCACTGTTCCCAGGCTTCAACCTCAGTGACCCCCCCCAACAACTCCCCATGGA

GAGTCCCTGCCCAAAAAAGCTGTAGGATCCAAGGGGTGTCAATAGCTCGTTCCCGGCATCACCTACACAC

CACAAGCAGGTTTTAATGGAAGCAAGTTGCTCCACCAAATCCACAAAAGGGTAAAGTTTGTGATTTTTCT

TTATCATTGCGATCACCATCTGATACCGTAAGGAGTGCACTTGTTTGGAAGTTCTGACTTCTCTGATCTG

TCTTGGTCGTTTGTGTTATAAAACCAAAGTTCTCTACAGACTTTATTTTTGTACAATATCATTTTGTAAC

TTTTTA CAAAT AAAAAC TCATTTCTATTGC
```

>gi |299473776 |ref |NM_199231.2| *Homo sapiens* glial cell derived
neurotrophic factor (GDNF) , transcript variant 2, mRNA (SEQ ID NO: 2)
```
CATACAGGCCAAAAGTCTCCAAGTCCCTGCTAACTTCTTGCTCTCGCAACAGAATACCTATTTAGGTGGG

AAGAATGAGGTGTGGGCGGCAGGCTGGGTGCCGCCGCCGGACGGGACTTTAAGATGAAGTTATGGGATGT

CGTGGCTGTCTGCCTGGTGCTGCTCCACACCGCGTCCGCCTTCCCGCTGCCCGCCGCAAATATGCCAGAG

GATTA TCCTGATCAGTTCGA TGA TGTCA TGGA TTTTA TTCAAGC CACCA TTAAAAG ACTGAAAAGG TCAC

CAGATAAACAAATGGCAGTGCTTCCTAGAAGAGAGCGGAATCGGCAGGCTGCAGCTGCCAACCCAGAGAA

TTCCAGAGGAAAAGGTCGGAGAGGCCAGAGGGGCAAAAACCGGGGTTGTGTCTTAACTGCAATACATTTA

AATGTCACTGACTTGGGTCTGGGCTATGAAACCAAGGAGGAACTGATTTTTAGGTACTGCAGCGGCTCTT

GCGATGCAGCTGAGACAACGTACGACAAAATATTGAAAAACTTATCCAGAAATAGAAGGCTGGTGAGTGA

CAAAGTAGGGCAGGCATGTTGCAGACCCATCGCCTTTGATGATGACCTGTCGTTTTTAGATGATAACCTG

GTTTACCATATTCTAAGAAAGCATTCCGCTAAAAGGTGTGGATGTATCTGACTCCGGCTCCAGAGACTGC

TGTGTATTGCATTCCTGCTACAGTGCAAAGAAAGGGACCAAGGTTCCCAGGAAATGTTTGCCCAGAATGG

AAGA TGAGGA CCAAG GAGGCGGAGGAGGAG GAAGAAGAAGAGGAGGAGGAGGAGGAGGAGGAGGAGGAGG

AGGAAGGCAGCCATCATGGGAGCCTGGTAGAGGGAGATCCAGCTACAGACAACTGGACAGGAGAGAGAGA

AAACAGCCCTCTGGATTCTCCAGGATGGCAGCCGATGTCACTAGAAGCTCAGGGCTGATGTTCCTGGTTG

GCTATTGCCACCATTTCAGCTGATACAGTCCACCATCACTGATTACCGGCGCGGTTGCGGTGGATGCACT

TGAACCAAACCAGTGTATCTCCTGTGATTTGTTTTCATGTGTCCGAAGACACCAGGGAAACAGAGATCCT

GGTGTTGTTCCTTGTTATTACGTTTTACTGCTGAAAGTAAGAGGTTTATTTTTCTGTCACTCAGTGGAGA

CATACCCTGGAAAGGAGAGGGAAAAAAAAAGCAAAGATACAAGAGATAATCACCTTTGCATTTGAAAGT

TGAGGCCCGAGGTTTACTACAACCAGCATTTTTGCCAACGGTTGGTGATTGATTTCCATCACGGTGTGTG

GGGTGGGAAGAAGTTGGCTAGGAACCAAAAAGGCTGTGCTCATGATTAAACACAAACCTGAAGGTATTTC

CTTTATGTCCTTGGAAACAGGAAACGAGTTGTGGTTTTCGCCAGCATTCTTGTAGGAGAGAATCGGGGAA

GGCCCCGAACTGCCCCCGGGCAGGGAGAGCCCCTCAGGCCTGTTGGTTTACAGAGAGACAGATGTTACAT

AACCAGCTCCGTTGATGCGTGGTCACCAGTGACCAGAGAAGCTACTCGATGCAATGCATCTGTTTCAGAT

ACAGAAAT A TAGAGAAGA TA TTTA TTGAAAT TTAAG TTA TTGTTA TTTA TTACCGTTCACTAAT GAAT TT

CTCTTTTTTCCCTTATTTATTAAAGTTTCTTTTCAAAGGTGCCAAAGTATATGTGCTCGCAAAATGCAAA

GAAAGGTGACAAAAGGAAATTTGAATTGGGAACAAGGGTCCATGCTTTTCAAAGTATTAAAAAGTTTTTT

GCCAGGCAAAAATCACTTACTTTACCTTTTTAAGAAAATTTGTCATTAATTTTCCCCAGATTTCAGCATT
```

-continued

```
TTTCCCAATTTTTATTTGTGGAGCATCTCAGGCAAGCCCCCTTTCCTGGAGCAGCGTGCAGAGACCACTG

GCACTTGACTTTATTTCTTCCTTGCTCCATTGCTGAACAGAAATGTCGTGGGCTCCACTTCCTGTTGTCT

TTAAGC TCTTAGTCCCCTCCACGTA TA CCTA TCTGTA CTA TGCA TAAC CA TA TGTA GAAAAGG TTCAGTT

CCTTTTAGTAGGTAGTCCTGGATTTAATGCTGACCTAAAAGTAATGTCGACAATGCTGTCAGGTAGCTGC

CGTTCTACCGACTCCCTCCATCCCTGCCCACCCACTGCCCTCCCGAGAATATGCTGGCTGCCCAGTGCAG

CCCGGGAGACACAGGGGCCTTCCAGAGGTAGGGTCTACCAGGTCCTGTACAACCCCTGGGCTGTCACCGG

GGGTCAACAGCTGCTGCTCCTATATACCCAAACACCTGACAGCTCCCTGGGGAGCAGATGGCTGAGAAGG

GTGCTGAGGAAGCCATATTGGGACCAGCCACAGCCACACACATGGAGCCTCATACTTAGGAGCGTGCTGC

CTTTAAATGAAGGTGGTCGGGGCCAGTGCAGCGGCTCACACCCATAATCCCAACACTTTGGAAAGCCAAG

GTGGGAGGATCTCTTGAACCCAGGAGTTTGAGACCAGCTGGGCAACATAGGGAGACCCTGTCTCTACAG

AAACTTTAAAAATTAGGCAGGCATGATGGTGCACACCTGTGGTCCCAGCTACTCAAGAGGCTGAAGGAGG

ATCACTTGAGTCCAGAAGGTCGAGGCTGCAGTGAGCTGTGATCATGCCACTGCACTCCAGCCTAAGTGAC

AGTGCGGTACCCTGTCTCAAAAAAAAAAAAAAAAAAAAAAGAGGTTGGAGCAGGAGGAAGCATAGGGGC

GGGAACAGCCACCTCCTCCATGCCCTAGATTGTGAATTTATCGGGCAGCCAACACATGTATGACACACTA

GGCCCTGTATTACAGCTTGTTACGCATTTCATAAAAGGGATTTTCATTAAGGAGATAATCTATTACTACC

TACCTTAGTGGCTACTAGTATAAAACTATGACAGATTTAGCAATTAAATGAAATACTGGCCTCCATCAAA

TAATCATAGTAACAAGAAGCAGCAGTTACCAGACATCTGATCCCCTTCCCCAAAATACCCAAATTCTTC

ATGGTTCTGCCCTTCTCTGTCCTTTCTGCTCCCCTTGCTCGCCTGGGAAATGGAGGAAAGGCCTTCCCTC

TCACACTGTCTTGGGATCTTGCTGAGAATTCAGACTGCTCGAAACAGTGACAAACCCCAGCCATCCAGTC

ATTCGTGGAGCACAATTTGGATGTGGCCCCAGGGGCATCTGTCCCATTCAGAGAACCTTGGCAGTGCGAT

GGCCACTGTTCCCAGGCTTCAACCTCAGTGACCCCCCCCAACAACTCCCCATGGAGAGTCCCTGCCCAAA

AAAGCTGTAGGATCCAAGGGGTGTCAATAGCTCGTTCCCGGCATCACCTACACACCACAAGCAGGTTTTA

ATGGAAGCAAGTTGCTCCACCAAATCCACAAAAGGGTAAAGTTTGTGATTTTTCTTTATCATTGCGATCA

CCATCTGATACCGTAAGGAGTGCACTTGTTTGGAAGTTCTGACTTCTCTGATCTGTCTTGGTCGTTTGTG

TTATAAAACCAAAGTTCTCTACAGACTTTATTTTTGTACAATATCATTTTGTAACTTTTTACAAATAAAA

ACTCATTTCTATTGC
```

>gi |299473778 |ref |NM_001190468.1| *Homo sapiens* glial cell derived
neurotrophic factor (GDNF), transcript variant 3, mRNA (SEQ ID NO: 3)

```
CCAAAGCGTCCGAGACTGGGTACAGTCGTCCAGGCGTGACGGGGGCGCGGGGAGCCAGTGACTCCTCTGG

GAGGGGAAGGGATTAGGGCCAGAATCTCTCAAAGGTGCAAAAATCCAGTCAAGAGAGGGTTTTCGGGTAT

ACCACGGAGGATTAAAACTTTCAAGACAAATGCAGTCTTTGCCTAACAGCAATGGTGCCGCCGCCGGACG

GGACTTTAAGATGAAGTTATGGGATGTCGTGGCTGTCTGCCTGGTGCTGCTCCACACCGCGTCCGCCTTC

CCGCTGCCCGCCGGTAAGAGGCCTCCCGAGGCGCCCGCCGAAGACCGCTCCCTCGGCCGCCGCCGCGCGC

CCTTCGCGCTGAGCAGTGACTCAAATATGCCAGAGGATTATCCTGATCAGTTCGATGATGTCATGGATTT

TATTCAAGCCACCATTAAAAGACTGAAAAGGTCACCAGATAAACAAATGGCAGTGCTTCCTAGAAGAGAG

CGGAATCGGCAGGCTGCAGCTGCCAACCCAGAGAATTCCAGAGGAAAAGGTCGGAGAGGCCAGAGGGGCA

AAAACCGGGGTTGTGTCTTAACTGCAATACATTTAAATGTCACTGACTTGGGTCTGGGCTATGAAACCAA

GGAGGAACTGATTTTTAGGTACTGCAGCGGCTCTTGCGATGCAGCTGAGACAACGTACGACAAAATATTG

AAAAACTTATCCAGAAATAGAAGGCTGGTGAGTGACAAAGTAGGGCAGGCATGTTGCAGACCCATCGCCT

TTGA TGA TGA CCTG TCGTTTTTAGA TGA TAAC CTGGTTTACCA TA TTCTAAGAAAGC A TTCCGCTAAAAG

GTGTGGATGTATCTGACTCCGGCTCCAGAGACTGCTGTGTATTGCATTCCTGCTACAGTGCAAAGAAAGG
```

-continued

```
GACCAAGGTTCCCAGGAAATGTTTGCCCAGAATGGAAGATGAGGACCAAGGAGGCGGAGGAGGAGGAAGA

AGAAGAGGAGGAGGAGGAGGAGGAGGAGGAGGAGGAGGAAGGCAGCCATCATGGGAGCCTGGTAGAGGGA

GATCCAGCTACAGACAACTGGACAGGAGAGAGAGAAAACAGCCCTCTGGATTCTCCAGGATGGCAGCCGA

TGTCACTAGAAGCTCAGGGCTGATGTTCCTGGTTGGCTATTGCCACCATTTCAGCTGATACAGTCCACCA

TCACTGATTACCGGCGCGGTTGCGGTGGATGCACTTGAACCAAACCAGTGTATCTCCTGTGATTTGTTTT

CATGTGTCCGAAGACACCAGGGAAACAGAGATCCTGGTGTTGTTCCTTGTTATTACGTTTTACTGCTGAA

AGTAAGAGGTTTATTTTTCTGTCACTCAGTGGAGACATACCCTGGAAAGGAGAGGGGAAAAAAAAGCAA

AGATACAAGAGATAATCACCTTTGCATTTGAAAGTTGAGGCCCGAGGTTTACTACAACCAGCATTTTTGC

CAACGGTTGGTGATTGATTTCCATCACGGTGTGTGGGGTGGGAAGAAGTTGGCTAGGAACCAAAAAGGCT

GTGCTCATGATTAAACACAAACCTGAAGGTATTTCCTTTATGTCCTTGGAAACAGGAAACGAGTTGTGGT

TTTCGCCAGCATTCTTGTAGGAGAGAATCGGGGAAGGCCCCGAACTGCCCCGGGCAGGGAGAGCCCCTC

AGGCCTGTTGGTTTACAGAGAGACAGATGTTACATAACCAGCTCCGTTGATGCGTGGTCACCAGTGACCA

GAGAAGC TACTCGA TGCAAT GCA TCTGTTTCAGA TACAGAAAT A TAGAGAAGA TA TTTA TTGAAAT TTAA

GTTATTGTTATTTATTACCGTTCACTAATGAATTTCTCTTTTTTCCCTTATTTATTAAAGTTTCTTTTCA

AAGGTGCCAAAGTATATGTGCTCGCAAAATGCAAAGAAAGGTGACAAAAGGAAATTTGAATTGGGAACAA

GGGTCCATGCTTTTCAAAGTATTAAAAAGTTTTTTGCCAGGCAAAAATCACTTACTTTACCTTTTTAAGA

AAATTTGTCATTAATTTTCCCCAGATTTCAGCATTTTTCCCAATTTTTATTTGTGGAGCATCTCAGGCAA

GCCCCCTTTCCTGGAGCAGCGTGCAGAGACCACTGGCACTTGACTTTATTTCTTCCTTGCTCCATTGCTG

AACAGAAATGTCGTGGGCTCCACTTCCTGTTGTCTTTAAGCTCTTAGTCCCCTCCACGTATACCTATCTG

TACTATGCATAACCATATGTAGAAAAGGTTCAGTTCCTTTTAGTAGGTAGTCCTGGATTTAATGCTGACC

TAAAAGTAATGTCGACAATGCTGTCAGGTAGCTGCCGTTCTACCGACTCCCTCCATCCCTGCCCACCCAC

TGCCCTCCCGAGAATATGCTGGCTGCCCAGTGCAGCCCGGGAGACACAGGGGCCTTCCAGAGGTAGGGTC

TACCAGGTCCTGTACAACCCCTGGGCTGTCACCGGGGGTCAACAGCTGCTGCTCCTATATACCCAAACAC

CTGACAGCTCCCTGGGGAGCAGATGGCTGAGAAGGGTGCTGAGGAAGCCATATTGGGACCAGCCACAGCC

ACACACATGGAGCCTCATACTTAGGAGCGTGCTGCCTTTAAATGAAGGTGGTCGGGGCCAGTGCAGCGGC

TCACACCCATAATCCCAACACTTTGGAAAGCCAAGGTGGGAGGATCTCTTGAACCCAGGAGTTTGAGACC

AGCTTGGGCAACATAGGGAGACCCTGTCTCTACAGAAACTTTAAAAATTAGGCAGGCATGATGGTGCACA

CCTGTGGTCCCAGCTACTCAAGAGGCTGAAGGAGGATCACTTGAGTCCAGAAGGTCGAGGCTGCAGTGAG

CTGTGATCATGCCACTGCACTCCAGCCTAAGTGACAGTGCGGTACCCTGTCTCAAAAAAAAAAAAAAAAA

AAAAAAGAGGTTGGAGCAGGAGGAAGCATAGGGGCGGGAACAGCCACCTCCTCCATGCCCTAGATTGTGA

ATTTATCGGCAGCCAACACATGTATGACACACTAGGCCCTGTATTACAGCTTGTTACGCATTTCATAAA

AGGGATTTTCATTAAGGAGATAATCTATTACTACCTACCTTAGTGGCTACTAGTATAAAACTATGACAGA

TTTAGCAATTAAATGAAATACTGGCCTCCATCAAATAATCATAGTAACAAGAAGCAGCAGTTACCAGACA

TCTGATCCCCTTCCCCCAAAATACCCAAATTCTTCATGGTTCTGCCCTTCTCTGTCCTTTCTGCTCCCCT

TGCTCGCCTGGGAAATGGAGGAAAGGCCTTCCCTCTCACACTGTCTTGGGATCTTGCTGAGAATTCAGAC

TGCTCGAAACAGTGACAAACCCCAGCCATCCAGTCATTCGTGGAGCACAATTTGGATGTGGCCCCAGGGG

CATCTGTCCCATTCAGAGAACCTTGGCAGTGCGATGGCCACTGTTCCCAGGCTTCAACCTCAGTGACCCC

CCCCAACAACTCCCCATGGAGAGTCCCTGCCCAAAAAAGCTGTAGGATCCAAGGGGTGTCAATAGCTCGT

TCCCGGCATCACCTACACACCACAAGCAGGTTTTAATGGAAGCAAGTTGCTCCACCAAATCCACAAAAGG

GTAAAGTTTGTGATTTTTCTTTATCATTGCGATCACCATCTGATACCGTAAGGAGTGCACTTGTTTGGAA
```

```
GTTCTGACTTCTCTGATCTGTCTTGGTCGTTTGTGTTATAAAACCAAAGTTCTCTACAGACTTTATTTTT

GTACAATATCATTTTGTAACTTTTTACAAATAAAAACTCATTTCTATTGC
```

>gi |299473780 |ref |NM_001190469.1| *Homo sapiens* glial cell derived neurotrophic factor (GDNF), transcript variant 4, mRNA (SEQ ID NO: 4)

```
CCAAAGCGTCCGAGACTGGGTACAGTCGTCCAGGCGTGACGGGGGCGCGGGGAGCCAGTGACTCCTCTGG

GAGGGGAAGGGATTAGGGCCAGAATCTCTCAAAGGTGCAAAAATCCAGTCAAGAGAGGGTTTTCGGGTAT

ACCACGGAGGATTAAAACTTTCAAGACAAATGCAGTCTTTGCCTAACAGCAATGGTGCCGCCGCCGGACG

GGACTTTAAGATGAAGTTATGGGATGTCGTGGCTGTCTGCCTGGTGCTGCTCCACACCGCGTCCGCCTTC

CCGCTGCCCGCCGCAAATATGCCAGAGGATTATCCTGATCAGTTCGATGATGTCATGGATTTTATTCAAG

CCACCATTAAAAGACTGAAAAGGTCACCAGATAAACAAATGGCAGTGCTTCCTAGAAGAGAGCGGAATCG

GCAGGCTGCAGCTGCCAACCCAGAGAATTCCAGAGGAAAAGGTCGGAGAGGCCAGAGGGGCAAAAACCGG

GGTTGTGTCTTAACTGCAATACATTTAAATGTCACTGACTTGGGTCTGGGCTATGAAACCAAGGAGGAAC

TGATTTTTAGGTACTGCAGCGGCTCTTGCGATGCAGCTGAGACAACGTACGACAAAATATTGAAAAACTT

ATCCAGAAATAGAAGGCTGGTGAGTGACAAAGTAGGGCAGGCATGTTGCAGACCCATCGCCTTTGATGAT

GACCTGTCGTTTTTAGATGATAACCTGGTTTACCATATTCTAAGAAAGCATTCCGCTAAAAGGTGTGGAT

GTATCTGACTCCGGCTCCAGAGACTGCTGTGTATTGCATTCCTGCTACAGTGCAAAGAAAGGGACCAAGG

TTCCCAGGAAATGTTTGCCCAGAATGGAAGATGAGGACCAAGGAGGCGGAGGAGGAGGAAGAAGAAGAGG

AGGAGGAGGAGGAGGAGGAGGAGGAGGAAGGCAGCCATCATGGGAGCCTGGTAGAGGGAGATCCAGC

TACAGACAACTGGACAGGAGAGAGAAAACAGCCCTCTGGATTCTCCAGGATGGCAGCCGATGTCACTA

GAAGCTCAGGGCTGATGTTCCTGGTTGGCTATTGCCACCATTTCAGCTGATACAGTCCACCATCACTGAT

TACCGGCGCGGTTGCGGTGGATGCACTTGAACCAAACCAGTGTATCTCCTGTGATTTGTTTTCATGTGTC

CGAAGACACCAGGGAAACAGAGATCCTGGTGTTGTTCCTTGTTATTACGTTTTACTGCTGAAAGTAAGAG

GTTTATTTTTCTGTCACTCAGTGGAGACATACCCTGGAAAGGAGAGGGAAAAAAAAAGCAAAGATACAA

GAGATAATCACCTTTGCATTTGAAAGTTGAGGCCCGAGGTTTACTACAACCAGCATTTTTGCCAACGGTT

GGTGATTGATTTCCATCACGGTGTGTGGGGTGGGAAGAAGTTGGCTAGGAACCAAAAAGGCTGTGCTCAT

GATTAAACACAAACCTGAAGGTATTTCCTTTATGTCCTTGGAAACAGGAAACGAGTTGTGGTTTTCGCCA

GCATTCTTGTAGGAGAGAATCGGGGAAGGCCCCGAACTGCCCCCGGGCAGGGAGAGCCCCTCAGGCCTGT

TGGTTTACAGAGAGACAGATGTTACATAACCAGCTCCGTTGATGCGTGGTCACCAGTGACCAGAGAAGCT

ACTCGA TGCAAT GCA TCTGTTTCAGA TACAGAAAT A TAGAGAAGA TA TTTA TTGAAAT TTAAG TTA TTGT

TATTTATTACCGTTCACTAATGAATTTCTCTTTTTTCCCTTATTTATTAAAGTTTCTTTTCAAAGGTGCC

AAAGTATATGTGCTCGCAAAATGCAAAGAAAGGTGACAAAAGGAAATTTGAATTGGGAACAAGGGTCCAT

GCTTTTCAAAGTATTAAAAAGTTTTTTGCCAGGCAAAAATCACTTACTTTACCTTTTTAAGAAAATTTGT

CATTAATTTTCCCCAGATTTCAGCATTTTTCCCAATTTTTATTTGTGGAGCATCTCAGGCAAGCCCCCTT

TCCTGGAGCAGCGTGCAGAGACCACTGGCACTTGACTTTATTTCTTCCTTGCTCCATTGCTGAACAGAAA

TGTCGTGGGCTCCACTTCCTGTTGTCTTTAAGCTCTTAGTCCCCTCCACGTATACCTATCTGTACTATGC

ATAACCATATGTAGAAAAGGTTCAGTTCCTTTTAGTAGGTAGTCCTGGATTTAATGCTGACCTAAAAGTA

ATGTCGACAATGCTGTCAGGTAGCTGCCGTTCTACCGACTCCCTCCATCCCTGCCCACCCACTGCCCTCC

CGAGAATATGCTGGCTGCCCAGTGCAGCCCGGGAGACACAGGGGCCTTCCAGAGGTAGGGTCTACCAGGT

CCTGTACAACCCCTGGGCTGTCACCGGGGGTCAACAGCTGCTGCTCCTATATACCCAAACACCTGACAGC

TCCCTGGGGAGCAGATGGCTGAGAAGGGTGCTGAGGAAGCCATATTGGGACCAGCCACAGCCACACACAT

GGAGCCTCATACTTAGGAGCGTGCTGCCTTTAAATGAAGGTGGTCGGGGCCAGTGCAGCGGCTCACACCC
```

-continued

```
ATAATCCCAACACTTTGGAAAGCCAAGGTGGGAGGATCTCTTGAACCCAGGAGTTTGAGACCAGCTTGGG

CAACATAGGGAGACCCTGTCTCTACAGAAACTTTAAAAATTAGGCAGGCATGATGGTGCACACCTGTGGT

CCCAGCTACTCAAGAGGCTGAAGGAGGATCACTTGAGTCCAGAAGGTCGAGGCTGCAGTGAGCTGTGATC

ATGCCACTGCACTCCAGCCTAAGTGACAGTGCGGTACCCTGTCTCAAAAAAAAAAAAAAAAAAAAAAAGA

GGTTGGAGCAGGAGGAAGCATAGGGGCGGGAACAGCCACCTCCTCCATGCCCTAGATTGTGAATTTATCG

GGCAGCCAACACATGTATGACACACTAGGCCCTGTATTACAGCCTTGTTACGCATTTCATAAAAGGGATTT

TCATTAAGG AGA TAAT CTATTACTACCTACCTTAGTGGC TA CTAGTA TAAAAC TA TGA CAGA TTTAGCAA

TTAAATGAAATACTGGCCTCCATCAAATAATCATAGTAACAAGAAGCAGCAGTTACCAGACATCTGATCC

CCTTCCCCCAAAATACCCAAATTCTTCATGGTTCTGCCCTTCTCTGTCCTTTCTGCTCCCCTTGCTCGCC

TGGGAAATGGAGGAAAGGCCTTCCCTCTCACACTGTCTTGGGATCTTGCTGAGAATTCAGACTGCTCGAA

ACAGTGACAAACCCCAGCCATCCAGTCATTCGTGGAGCACAATTTGGATGTGGCCCCAGGGGCATCTGTC

CCATTCAGAGAACCTTGGCAGTGCGATGCCACTGTTCCCAGGCTTCAACCTCAGTGACCCCCCCAACA

ACTCCCCATGGAGAGTCCCTGCCCAAAAAAGCTGTAGGATCCAAGGGGTGTCAATAGCTCGTTCCCGGCA

TCACCTACACCACAAGCAGGTTTTAATGGAAGCAAGTTGCTCCACCAAATCCACAAAAGGGTAAAGTT

TGTGATTTTTCTTTATCATTGCGATCACCATCTGATACCGTAAGGAGTGCACTTGTTTGGAAGTTCTGAC

TTCTCTGATCTGTCTTGGTCGTTTGTGTTATAAAACCAAAGTTCTCTACAGACTTTATTTTTGTACAATA

TCATTTTGTAACTTTTTACAAATAAAAACTCATTTCTATTGC
```

A representative cDNA encoding isoform 1 is as follows:

(SEQ ID NO: 5)
```
caaatatgccagaggattatcctgatcagttcgatgatgtcatggatttta ttcaagccaccattaaaagactgaaaaggtcaccagataaacaaatggcag tgcttcctagaagagagcggaatcggcaggctgcagctgccaacccagaga attccagaggaaaaggtcggagaggccagaggggcaaaaaccggggttgtg tcttaactgcaatacatttaaatgtcactgacttgggtctgggctatgaaa ccaaggaggaactgattttttaggtactgcagcggctcttgcgatgcagctg agacaacgtacgacaaaatattgaaaaacttatccagaaatagaaggctgg tgagtgacaaagtagggcaggcatgttgcagacccatcgcctttgatgatg acctgtcgttttagatgataacctggtttaccatattctaagaaagcatt ccgctaaaaggtgtggatgtatctga
```

GenBank Accession No. L19063.1, gi:306761. See Science 1993, 260 (5111):1130-2.

The amino acid sequences of the various human GDNF isoforms are as follows:

```
>gi |40549411 |ref |NP_954701.1| glial cell line-
derived neurotrophic factor isoform 2 pre-
proprotein [Homo sapiens]
                                   (SEQ ID NO: 6)
MKLWDVVAVCLVLLHTASAFPLPAANMPEDYPDQFDDVMDFIQATIKRL

KRSPDKQMAVLPRRERNRQAAAANPENSRGKGRRGQRGKNRGCVLTAIH

LNVTDLGLGYETKEELIFRYCSGSCDAAETTYDKILKNLSRNRRLVSDK

VGQACCRPIAFDDDLSFLDDNLVYHILRKHSAKRCGCI
```

```
>gi |4503975 |ref |NP_000505.1| glial cell line-
derived neurotrophic factor isoform 1 pre-
proprotein [Homo sapiens]
                                   (SEQ ID NO: 7)
MKLWDVVAVCLVLLHTASAFPLPAGKRPPEAPAEDRSLGRRRAPFALSS

DSNMPEDYPDQFDDVMDFIQATIKRLKRSPDKQMAVLPRRERNRQAAAA

NPENSRGKGRRGQRGKNRGCVLTAIHLNVTDLGLGYETKEELIFRYCSG

SCDAAETTYDKILKNLSRNRRLVSDKVGQACCRPIAFDDDLSFLDDNLV

YHILRKHSAKRCGCI
```

```
>gi |299473779 |ref |NP_001177397.1| glial cell
line-derived neurotrophic factor isoform 3
preproprotein [Homo sapiens]
                                   (SEQ ID NO: 8)
MQSLPNSNGAAAGRDFKMKLWDVVAVCLVLLHTASAFPLPAGKRPPEAP

AEDRSLGRRRAPFALSSDSNMPEDYPDQFDDVMDFIQATIKRLKRSPDK

QMAVLPRRERNRQAAAANPENSRGKGRRGQRGKNRGCVLTAIHLNVTDL

GLGYETKEELIFRYCSGSCDAAETTYDKILKNLSRNRRLVSDKVGQACC

RPIAFDDDLSFLDDNLVYHILRKHSAKRCGCI
```

```
>gi |299473781 |ref |NP_001177398.1| glial cell
line-derived neurotrophic factor isoform 4
preproprotein [Homo sapiens]
                                   (SEQ ID NO: 9)
MQSLPNSNGAAAGRDFKMKLWDVVAVCLVLLHTASAFPLPAANMPEDYP

DQFDDVMDFIQATIKRLKRSPDKQMAVLPRRERNRQAAAANPENSRGKG

RRGQRGKNRGCVLTAIHLNVTDLGLGYETKEELIFRYCSGSCDAAETTY

DKILKNLSRNRRLVSDKVGQACCRPIAFDDDLSFLDDNLVYHILRKHSA

KRCGCI
```

Like other growth factors GDNF has to be cleaved for secretion from the cell, and proteolytically processed for activation and also requires glycosaminoglycans for activation of specific signaling pathways. The GDNF amino acid sequence contains two potential glycosylation sites (discussed in greater detail below).

A multiple sequence alignment of the human GDNF isoforms is presented below. Signal sequences are depicted in bold. Signal peptides are aa 1-19, aa 1-19, and aa 1-36 for isoforms 1, 2 and 3, respectively. Mature peptides are depicted in italics. Mature peptides are aa 78-211, aa 52-185, and aa 95-228 for isoforms 1, 2 and 3, respectively. GDNF proteins have a key functional domain, termed the "transforming growth factor beta (TGF-β) like domain. TGF-β-like domains are aa 118-211, aa 92-185, and aa 135-228, for isoforms 1, 2 and 3, respectively. TGF-β-like domains are underlined.

and human and mouse sharing 94% identity (8 amino acids are different) when comparing mature protein sequences; human and rat sharing 92% identity and human and mouse sharing 93% identity when comparing preproprotein sequences.

Pairwise alignments of human vs. mouse and human vs. rat preproproteins are presented below. The glycosylation sites are Asn (=N) 126 and Asn 162, and are indicated in bold. The skilled artisan will understand that a glycosylation motif is described as NX[ST] where X=any amino acid. The glycosylation motifs in, for example, human GDNF (isoform 1) are as follows aa126-128 (with N-linked glycosy-

```
CLUSTAL 2.1 multiple sequence alignment (SEQ ID NOs: 6-9)
iso1   ----------------MKLWDWAVCLVLLHTAS AFPLPAGKRPPEAPAEDRSLGRRRA
iso3   MQSLPNSNGAAAGRDFKMKLWDWAVCLVLLHTASAFPLPAGKRPPEAPAEDRSLGRRRA
iso2   ----------------MKLWDWAVCLVLLHTAS AFPLPAAN-----------------
iso4   MQSLPNSNGAAAGRDFKMKLWDWAVCLVLLHTASAFPLPAAN-----------------
                       ***********************  .:

iso1   PFALSSDSNMPEDYPDQFDDVMDFIQATIKRLKRSPDKQMAVLPRRERNRQAAAANPENS
iso3   PFALSSDSNMPEOYPOQFOOVMOFIQATIKRLKRSPDKQMAVLPRRERNRQAAAANPENS
iso2   ---------MPEDYPDQFDDVMDF  IQATIKRhKRSPDKQMA VLPRRERNRQAAAANPENS
iso4   ---------MPEDYPDQFDDVMDF  IQAT IKRLKRSPDKQMAVLPRRERNRQAAAANPENS
                 ****************************************** iso1   RGKGRRGQRGKNR GCVLTAIHLNVTDLGLGYETKEEL IFRYCSGSCDAAETTYDKILKNL
iso3   RGKGRRGQRGKNR GCVLTAIHLNVTDLGLGYETKEEL IFRYCSGSCDAAETTYDKILKNL
iso2   RGKGRRGQRGKNR GCVLTAIHLNVTDLGLGYETKEEL IFRYCSGSCDAAETTYDKILKNL
iso4   RGKGRRGQRGKNR GCVLTAIHLNVTDLGLGYETKEEL IFRYCSGSCDAAETTYDKILKNL
       ************************************************************ iso1   SRNRRL VSDKVGQACCRP IAFDDDL SFLDDNL VYHILRKHSAKRCGCI
iso3   SRNRRL VSDKVGQACCRP IAFDDDL SFLDDNL VYHILRKHSAKRCGCI
iso2   SRNRRL VSDKVGQACCRP IAFDDDL SFLDDNL VYHILRKHSAKRCGCI
iso4   SRNRRL VSDKVGQACCRP IAFDDDL SFLDDNL VYHILRKHSAKRCGCI
       *************************************************
```

As mentioned above, the GDNF gene encodes a highly conserved neurotrophic factor. GDNF orthologs share, for example, about 90-95% identity (or more), e.g., human and rat sharing 92% identity (10 amino acids (aa) are different)

lation predicted to occur at N126, and at aa162-164 (with N-linked glycosylation predicted to occur at N162.) (See e.g., Lin et al., 1994, J. Neurochem, 63, 758-68; Trupp et al., 1995, J. Cell Biol, 130, 137-48).

```
Hu    1 MKLWDWAVCLVLLHTASAFPLPAGKRPPEAPAEDRSLGRRRAPFALSSDSNMPEDYPDQ    60
        MKLWDWAVCLVLLHTASAFPLPAGKR  EAPAED SLG RR PFAL+SDSNMPEDYPDQ
Mu    1 MKLWDWAVCLVLLHTASAFPLPAGKRLLEAPAEDHSLGHRRVPFALTSDSNMPEDYPDQ    60

Hu   61 FDDVMDFIQATIKRLKRSPDKQMAVLPRRERNRQAAAANPENSRGKGRRGQRGKNRGCVL   120
        FDDVMDFIQATIKRLKRSPDKQ A LPRRERNRQAAAA+PENSRGKGRRGQRGKNRGCVL
Mu   61 FDDVMDFIQATIKRLKRSPDKQAAALPRRERNRQAAAASPENSRGKGRRGQRGKNRGCVL   120

Hu  121 TAIHLNVTDLGLGYETKEELIFRYCSGSCDAAETTYDKILKNLSRNRRLVSDKVGQACCR   180
        TAIHLNVTDLGLGYETKEELIFRYCSGSC++AET YDKILKNLSR+RRL SDKVGQACCR
Mu  121 TAIHLNVTDLGLGYETKEELIFRYCSGSCESAETMYDKILKNLSRSRRLTSDKVGQACCR   180

Hu  181 PIAFDDDLSFLDDNLVYHILRKHSAKRCGCI                               211
        P+AFDDDLSFLDDNLVYHILRKHSAKRCGCI
Mu  181 PVAFDDDLSFLDDNLVYHILRKHSAKRCGCI                               211

Hu    1 MKLWDVVAVCLVLLHTASAFPLPAGKRPPEAPAEDRSLGRRRAPFALSSDSNMPEDYPDQ    60
        MKLWDVVAVCLVLLHTASAFPLPAGKR  EAPAED SLG RR PFAL+SDSNMPEDYPDQ
Ra    1 MKLWDVVAVCLVLLHTASAFPLPAGKRLLEAPAEDHSLGHRRVPFALTSDSNMPEDYPDQ    60

Hu   61 FDDVMDFIQATIKRLKRSPDKOMAVLPRRERNRQAAAANPENSRGKGRRGQRGKNRGCVL   120
        FDDVMDFIQATIKRLKRSPDKQ A LPRRERNRQAAAA+PENSRGKGRRGQRGKNRGCVL
Ra   61 FDDVMDFIQATIKRLKRSPDKQAAALPRRERNRQAAAASPENSRGKGRRGQRGKNRGCVL   120

Hu  121 TAIHLNVTDLGLGYETKEELIFRYCSGSCDAAETTYDKILKNLSRNRRLVSDKVGQACCR   180
        TAIHLNVTDLGLGYETKEELIFRYCSGSC+AAET YDKILKNLSR+RRL SDKVGQACCR
Ra  121 TAIHLNVTDLGLGYETKEELIFRYCSGSCEAAETMYDKILKNLSRSRRLTSDKVGQACCR   180
```

```
Hu    181 PIAFDDDLSFLDDNLVYHILRKHSAKRCGCI                           211
          P+AFDDDL FLDD+LVYHILRKHSAKRCGCI
Ra    181 PVAFDDDLWFLDDSLVYHILRKHSAKRCGCI                           211
```

Human, mouse and rat GDN sequence are set forth as SEQ ID NOs: 6, 10 and 11, respectively. The sequences appearing between aligned sequences above can be considered consensus sequences and are set forth as SEQ ID NOs: 12-13 (where no match between amino acids in aligned sequences can be depicted as X in a consensus sequence, X being one of the two mismatched residues, as depicted.

A multiple sequence alignment of human (isoform 1), mouse and rat GDNF orthologs (mature proteins) is presented below:

```
Hu     78 SPDKOMAVLPRRERNRQAAAANPENSRGKGRRGQRGKNRGCVL               120
Mu     78 SPDKQAAALPRRERNRQAAAASPENSRGKGRRGQRGKNRGCVL               120
Ra     78 SPDKQAAALPRRERNRQAAAASPENSRGKGRRGQRGKNRGCVL               120

Hu    121 TAIHLNVTDLGLGYETKEELIFRYCSGSCDAAETTYDKILKNLSRNRRLVSDKVGOACCR 180
Mu    121 TAIHLNVTDLGLGYETKEELIFRYCSGSCESAETMYDKILKNLSRSRRLTSDKVGQACCR 180
Ra    121 TAIHLNVTDLGLGYETKEELIFRYCSGSCEAAETMYDKILKNLSRSRRLTSDKVGQACCR 180

Hu    181 PXAFDDDLSFLDDNLVYHILRKHSAKRCGCI                           211
Mu    181 PVAFDDDLSFLDDNLVYHILRKHSAKRCGCI                           211
Ra    181 PVAFDDDLWFLDDSLVYHILRKHSAKRCGCI                           211
```

The above sequences are set forth as amino acids 78-211 of SEQ ID NOs: 6, 10 and 11 respectively.

Mature protein sequences are also envisioned in which a methionine (Met; M) precedes the first amino acid of the mature sequence. The M can be added for recombinant protein expression of mature proteins, and is encoded in engineered cDNA expression systems. However, the skilled artisan will appreciate that there are also expression systems which allow the cleavage of the N-terminal M, as it can induce autoimmune reactions or changes in activity of the expressed, mature protein. For example see Nakagawal et al. 1987, Nature Biotech 5, 824-827; Fernandez-San Millan et al., 2007, J Biotechnol. 20; 127(4):593-604; U.S. Pat. No. 4,870,017.

GDNF sequences are as described above and additional information on said sequences can be found in the GenBank references indicated by the referenced GenBank/gi reference numbers. GDNF sequences are also described in Science. 1993 May 21; 260(5111):1130-2; and in WO 93/06116 and U.S. Pat. No. 7,226,758B1. Truncated forms are further described in US20040127419(A1). Mutations of GDNF are described, for example in Eketjall et al. 1999, EMBO 8, 5901-5910. The GDNF protein is further disclosed in, e.g., U.S. Pat. No. 6,362,319 and European Patent No. 0 610 254, and a truncated form of GDNF in U.S. Pat. No. 6,184,200 and European Patent No. 0 920 448.

Exemplary aspects of the invention can further include modified (e.g., recombinantly-modified) forms of GDNF, or of biologically active fragments thereof. In one embodiment, the method of the invention feature the use of fusion proteins of GDNF, for example, fusion proteins including serum albumin or a biologically active fragment thereof, e.g., human serum albumin or a biologically active fragment thereof) Further exemplary aspects of the invention feature pegylated GDNF proteins, glycan-modified GDNF proteins (e.g., having N-glycan integrated within the protein) and/or polymer-conjugated GDNF (e.g., polymers consisting of a polystyrene backbone with side chains of trehalose.)

Preferred aspects of the invention feature GDNF polypeptides, GDNF homologs (e.g., GDNF orthologs) and/or biologically active portions (i.e., bioactive fragments) of GDNF polypeptides. In one embodiment, GDNF polypeptides can be isolated from cells or tissue sources by an appropriate purification scheme using standard protein purification techniques. GDNF polypeptide can be further derived from said isolated polypeptides using standard enzymatic techniques. In another embodiment, GDNF polypeptides or bioactive fragments thereof are produced by recombinant DNA techniques. Alternative to recombinant expression, GDNF polypeptides or bioactive fragments thereof can be synthesized chemically using standard peptide synthesis techniques.

Polypeptides of the invention are preferably "isolated" or "purified". The terms "isolated" and "purified" are used interchangeably herein. "Isolated" or "purified" means that the protein or polypeptide is substantially free of cellular material or other contaminating proteins from the cell or tissue source from which the polypeptide is derived, substantially free of other protein fragments, for example, non-desired fragments in a digestion mixture, or substantially free from chemical precursors or other chemicals when chemically synthesized. The language "substantially free of cellular material" includes preparations in which the polypeptide is separated from other components of the cells from which it is isolated or recombinantly produced. In one embodiment, the language "substantially free of cellular material" includes preparations of polypeptide having less than about 30% (by dry weight) of non-GDNF polypeptide (also referred to herein as a "contaminating protein"), more preferably less than about 20% of non-GDNF polypeptide, still more preferably less than about 10% of non-GDNF polypeptide, and most preferably less than about 5% non-GDNF polypeptide. When the polypeptide or protein is recombinantly produced, it is also preferably substantially free of culture medium, i.e., culture medium represents less than about 20%, more preferably less than about 10%, and most preferably less than about 5% of the volume of the polypeptide preparation. When the polypeptide or protein is produced by, for example, chemical or enzymatic processing from isolated or purified GDNF protein, the preparation is preferably free of enzyme reaction components or chemical reaction components and is free of non-desired GDNF forms, e.g., aggregates, or GDNF fragments, i.e., the desired polypeptide represents at least 75% (by dry weight) of the preparation, preferably at least 80%, more preferably at least 85%, and even more preferably at least 90%, 95%, 99% or more or the preparation.

The language "substantially free of chemical precursors or other chemicals" includes preparations of polypeptide in which the polypeptide is separated from chemical precursors or other chemicals which are involved in the synthesis of the polypeptide. In one embodiment, the language "substantially free of chemical precursors or other chemicals" includes preparations having less than about 30% (by dry weight) of chemical precursors or reagents, more preferably less than about 20% chemical precursors or reagents, still more preferably less than about 10% chemical precursors or reagents, and most preferably less than about 5% chemical precursors or reagents.

Bioactive fragments of GDNF polypeptides include polypeptides comprising amino acid sequences sufficiently identical to or derived from the amino acid sequence of the GDNF protein, respectively, which include less amino acids than the full length protein, and exhibit at least one biological activity of the full-length protein. Typically, biologically active portions comprise a domain or motif with at least one activity of the full-length protein. A biologically active portion of a GDNF polypeptide can be a polypeptide which is, for example, 10-20, 20-30, 30-40, 40-50, 50-60, 60-70, 70-80, 80-90, 90-100, 100-120, 120-140, 140-160, 160-200, or more amino acids in length. In a preferred embodiment, a bioactive portion of a GDNF protein comprises a TGFP-like domain. Moreover, other biologically active portions, in which other regions of the protein are deleted, can be prepared by recombinant techniques and evaluated for one or more of the functional activities of a native GDNF protein. Mutants of GDNF can also be utilized as assay reagents or therapeutic or pharmaceutical agents, for example, mutants having reduced, enhanced or otherwise altered biological properties identified according to one of the activity assays described herein.

As defined herein, a GDNF polypeptide of the invention includes polypeptides having the amino acid sequences set forth above, as well as homologs and/or orthologs of said polypeptides, i.e. polypeptides having sufficient sequence identity to function in the same manner as the described polypeptides. To determine the percent identity of two amino acid sequences (or of two nucleotide or amino acid sequences), the sequences are aligned for optimal comparison purposes {e.g., gaps can be introduced in the first sequence or second sequence for optimal alignment). The amino acid residues or nucleotides at corresponding amino acid positions or nucleotide positions are then compared. When a position in the first sequence is occupied by the same residue as the corresponding position in the second sequence, then the molecules are identical at that position. The percent identity between the two sequences is a function of the number of identical positions shared by the sequences {i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity {i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10. BLAST alignments can be generated and percent identity calculated using BLAST protein searches {e.g., the XBLAST program) using GDNF protein, or a portion thereof as a query, score=50, wordlength=3.

In another embodiment, the alignment is optimized by introducing appropriate gaps and percent identity is determined over the length of the aligned sequences {i.e., a gapped alignment). To obtain gapped alignments for comparison purposes, Gapped BLAST can be utilized as described in Altschul et al., (1997) *Nucleic Acids Research* 25(17):3389-3402. In another embodiment, the alignment is optimized by introducing appropriate gaps and percent identity is determined over the entire length of the sequences aligned {i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

A GDNF bioactive fragment is any fragment of GDNF having sufficient size and structure to carry out at least one activity {e.g., biological activity) of the corresponding full-length GDNF protein. Exemplary bioactive fragments include, but are not limited to, enzymatic domains, protein binding and/or interaction domains, receptor binding domains, and the like. Preferred bioactive fragments include regions or domains comprising a TGFP-like domain, as defined herein.

The GDNF protein or GDNF bioactive fragment, may be detectably labeled. As defined herein, a protein or protein fragment which is "detectably labeled" is on which has been modified to include a component detectable by standard laboratory means, e.g., the protein has been radioactively labeled, chromogenically labeled, or fluorescently labeled. Labeling can be direct, i.e., protein is modified to directly contain the detectable label, or can be indirect, e.g., the protein is modified to include a component with which the detectable label interacts. Furthermore, in other embodiments, the activity of a GDNF protein or GDNF bioactive fragment may be compared to an appropriate control.

In preferred embodiments, a GDNF polypeptide or homolog or bioactive fragment thereof includes at least a TGFp-like, as defined herein. The TGFp-like domain is a domain conserved among most, if not all TGFP family members. To identify the presence of a TGFp-like domain in an GDNF polypeptide, the amino acid sequence of the polypeptide can be searched against a database of conserved protein domains (e.g., the CD database at the NCBI) using the default parameters (Marchler-Bauer A et al. (2013), "COO: conserved domains and protein three-dimensional structure.", Nucleic Acids Res. 41(D1):D384-52.). NCBI Conserved Domains Database Accession number pfam00019 sets forth a conserved TGFp-like domain amino acid sequence.

In exemplary embodiments, a TGFp-like domain includes about 90-110 amino acid residues, e.g., about 90-100 or 91, 92, 93, 94, 95, 96, 97, 98, 99 or 100 amino acid residues). In exemplary embodiments, a domain identification score of 60 is a suitable threshold score for determining the presence of the domain. For example, searches using the amino acid sequences of human GDNF (isoform 1), mouse GDNF and rat GDNF were performed against the CD database resulting in the identification of a TGFp-like domain at amino acids 118-211 in each protein.

In preferred embodiments, a GDNF composition is a mature human GDNF protein consisting of 134 amino acids, i.e., amino acids 78-211 of SEQ ID NO:6. This sequence contains two putative N-glycosylation sites as well as seven conserved cysteines in the same relative spacing as the other members of the TGF-beta protein family (Lin et al. 1993, Science, 260: 1130-1132; Eigenbrot and Gerber, 1997, Nat Struct Biol, 4:435-438; Chang et al. 2002, Endocri Rev, 23:787-823). Biologically active mature GDNF dimer is formed by a covalent disulfide bond between the unpaired cysteines in the monomers (Eigenbrot and Gerber, 1997, Nat Struct Biol, 4:435-438).

In other exemplary embodiments, a GDNF protein for use in the methods of the invention can be a variant GDNF protein (or polypeptide), e.g., a variant having at least 90% or at least 95% or more identity. Preferred are biologically active variant GDNF polypeptides. As used herein, the phrase "biologically active variant GDNF polypeptide" refers to a GDNF polypeptide that, when dimerized, binds to a ternary complex containing GFRa1 and RET. Any method for detecting binding to this complex can be used to evaluate the biological activity a variant GDNF polypeptide. Exemplary assays for detecting the ternary complex-binding ability of a variant GDNF polypeptide are described in WO00/01815. Variant GDNF polypeptides can also be assayed or tested for their ability to trigger a GDNF signaling cascade. For example, a kinase receptor activation (KIRA) assay can be used to assess the ability of a variant GDNF polypeptide to induce RET autophosphorylation (see e.g., Sadick et al., 1996, Anal. Biochem., 235(2): 207) or assays can be performed to detect expression of downstream targets of a GDNF signaling cascade, e.g., increased expression of ret or fgfr2.

III. Wound Healing

The body's response to skin injury is focused on rapid wound closure, restraining invasion of microorganisms, and preventing excessive fluid loss (Singer A J, et al., *N Engl J Med* 341:738-46, 1999; Aarabi S, et al., *PLoS Med* 4:e234, 2007; Gurtner G C, et al., *Nature* 453:314-21, 2008; Mustoe T., *Am J Surg* 187:65S-70S, 2004).

An increased understanding of the molecular mechanisms that regulate the various events of wound healing has laid the foundation for therapeutic interventions attempting to improve the healing outcome. The cell-cell and cell-matrix interactions are fundamental for successful wound healing, and growth factors and cytokines maintain the balance of signals that regulate cellular migration, proliferation, and adhesion to a large extent. Freedberg I M, et al., *J Invest Dermatol* 116:633-40, 2001; Hantash B M, et al., *Front Biosci* 13:51-61, 2008; Werner S, et al, *Physiol Rev* 83:835-70, 2003; Barrientos S, et al., *Wound Repair Regen* 16:585-601, 2008. Malfunction leads to a prolonged healing time or complete failure to heal and may result in a chronic wound. The wound fluid from chronic wounds has an increased concentration of proinflammatory cytokines in comparison with wound fluid from acute wounds. Bennett N T, et al., *Am J Surg* 166:74-81, 1993; Robson M C, et al., *Arch Surg* 135:773-7, 2000. By contrast, there is a decreased concentration of growth factors in chronic wounds with high protease activity and decreased levels of natural protease inhibitors. Nwomeh B C, et al. s *Clin Plast Surg* 25:341-56, 1998; Mast B A, et al, *Wound Repair Regen* 4:411-20, 1996; Tarnuzzer R W, et al., *Wound Repair Regen* 4:321-5, 1996. This deficiency in growth factors can be attributable to decreased production or secretion, more rapid breakdown, and, as is the case in venous stasis ulcers, binding to in macromolecules, making them nonfunctional. Robson M C, et al., *Arch Surg* 135:773-7, 2000; Falange V, et al., *Lancet* 341:1006-8, 1993.

Glial cell line-derived neurotrophic factor (GDNF), neurturin (NTN), and their receptors, GDNF family receptor a-1 (GFRa-1) and GDNF family receptor a-2 (GFRa-2), are critically important for development in systems such as kidney and nervous system. Moreover, Gdnf has been shown to be expressed in embryonic skin where Gdnf mRNA is detected in both epithelial and mesenchymal components (Hellmich et al. 1996, Mech Dev 54, 95-105). However, the role of these factors (e.g., GDNF) in skin biology, and in particular, wound healing, is as yet not fully understood. Knowledge of the role of this important factor in skin biology would be helpful in understanding not only the various normal wound-healing events but also those occurring under distinct pathological conditions, for example, conditions in which wound healing is impaired, e.g., pathological conditions such as diabetes. In addition, development of effective novel therapies for wound healing can based, at least in part, on this better understand of the effect of GDNF on the total wound-healing process. This approach facilitates the development of new products with potential applications in wound healing and other area of skin biology.

In humans, and more widely in all mammalian species, the wound-healing process can be subdivided into three consecutive and overlapping phases: inflammation, tissue formation, and matrix formation and remodeling. Rodero, M. P., et al., *Int. J. Clin. Exp. Pathol.* 3:643653, 2010. The transition from one phase to another depends on the maturation and differentiation of the main cell populations involved, among which keratinocytes, fibroblasts, neutrophils, and macrophages play the main roles. Rodero, M. P., et al., *Int. J. Clin. Exp. Pathol.* 3:643653, 2010; Leibovich, S. J., et al., *Aηt. J. Pathol.* 78:71-100, 1975; Deonarine, K., et al., *J. Transl. Med.* 5:11, 2011; Becker, D. L., et al., *Biochim. Biophys Acta* 1818:2068-2075, 2011. Recent observations show that stem cells have an unclear but likely major role in response to cutaneous injury, Lanza R., *Handbook of Stem Cells*. Academic Press, 2004, as well as the evidence for the roles of M1 and M2 macrophage, and that of T cells. Gilliver, S. C., et al., *Exp. Dermatol.* 20:1-6, 2011; Sindrilaru, A., et al, *J. Clin. Invest.* 121:985-997, 2011.

Initial stages of wound healing involve the formation of a blood clot and inflammation. The inflammatory response is followed by proliferation and migration of dermal and epidermal cells, and matrix synthesis, in order to fill the wound gap and reestablish the skin barrier (Cotran, et al., 1999; Hackam, D. J., et al. *Surg Infect* 3 (Suppl 1), S23-5 (2002); Harding, K. G., et al. *Int Wound J* 2, 364-8 (2005)). Finally, tissue remodeling and differentiation enable full recovery of the skin tissue and restoration of skin aesthetics (Hackam, D. J., et al. *Surg Infect* 3 (Suppl 1), S23-5 (2002); Diegelmann, R. F., et al. *Front Biosci* 9, 283-9 (2004)). The consensus in the literature is that the stepwise process of wound healing first strives toward immediate filling of the gap, followed by re-epithelialization and reestablishment of the skin barrier (Yamaguchi, Y., et al. *J Dermatol* 28, 521-34, (2001)).

The early response is activated immediately after injury, resulting in the inflammatory phase (first stage) of wound healing. Grose R, et al., *Mol Biotechnol* 28:147-66, 2004. After hemostasis a fibrin clot is formed, which later serves as a scaffold for infiltrating cells. In addition, neutrophils and monocytes are recruited to the wound in response to trauma and bacterial contamination. Martin P, et al., *Trends Cell Biol* 15:599-607, 2005. In detail, the first event occurring after injury is the formation of a blood clot; several cells are involved in the blood plug: platelets, and red and white blood cells. With the action of fibrin fibers, the clot is stabilized and then "invaded" by several infiltrating cells, such as neutrophils, macrophages, mastocytes, platelets, and, possibly, by bacteria and toxins, which are counteracted by host-generated H2O2. Neutrophils massively infiltrating the wound during the first 24 hours post injury are attracted by numerous inflammatory cytokines produced by activated platelets, endothelial cells, as well as by degradation products from pathogens. Macrophages massively infiltrating the wound two days postinjury produce intense phagocytic activity. Mosser, D. M., et al., *Nature Rev. Immunol.* 8:958-969, 2008.

The second stage of wound repair (tissue formation) occurs approximately 2 to 10 days after the injury and is characterized by proliferation and migration of different cell types. Keratinocytes migrate over the wound bed while fibroblasts and macrophages replace the fibrin clot with granulation tissue. Werner S, et al., *J Invest Dermatol* 27:998-1008, 2007. The newly formed immature dermis is neovascularized, and the keratinocytes behind the leading edge proliferate and differentiate to restore the barrier function of the epidermis. In detail, after two to three days, the second phase lasts about two weeks and is characterized by neo-angiogenesis and granulation. During the re-epithelialization process, keratinocytes from the wound edges migrate over the wound bed at the interface between the wound dermis and the fibrin clot. This migration is facilitated by the production of specific proteases, such as collagenase by the epidermal cells to degrade the extracellular matrix. Activated fibroblasts also migrate to the wound bed and form, with the macrophages, granulation tissue. Intense angiogenesis, allowing the supply of oxygen and nutrients necessary for the healing process, also occurs within the tissue. Both growth factors and reactive oxygen species (ROS) produced by the granulation tissue will favor proliferation and differentiation of epithelial cells, restoring epithelial barrier integrity Tissue remodeling, the third stage of wound repair, begins 2 to 3 weeks after injury and lasts for 1 year or more. The type III collagen that is deposited in the initial stages of wound healing is slowly replaced by type I collagen, thereby forming the mature dermis. Loworn H N 3$^{rd}$, et al, *J Pediatr Surg* 34:218-23, 1999. In detail, The last stage of the wound-healing process consists in a gradual involution of the granulation tissue and dermal regeneration. This step is associated with apoptosis of myofibroblasts, endothelial cells, and macrophages. The remaining tissue is therefore composed mostly of extracellular matrix proteins, essentially collagen type III that will be remodeled by metalloproteinase produced by epidermal cells, endothelial cells, fibroblasts, and the macrophages remaining in the scar and then replaced by collagen type I. Singer, A. J., et al, *N. Engl. J. Med.* 341:738-746, 1999.

IV. Hair Growth

As is the case for wound healing, the role of Glial cell line-derived neurotrophic factor (GDNF) and its receptors in hair growth control, is as yet not fully understood. As mentioned above, Gdnf has been shown to be expresses in embryonic skin where Gdnf mRNA is detected in both epithelial and mesenchymal components {Hellmich et al. 1996, *Mech Dev* 54, 95-105). Gdnf has also been shown to be expressed during human hair follicle development (Adly et al. 2008 *J Am Acad Dermatol,* 58:238-250) and has further been shown to be expressed in adult mice in hair follicles during the anagen to catagen transition phase (Botchkareva et al. 2000, *Am J Pathol* 156, 1041-1053). These gene expression patterns suggest a role for GDNF in the hair follicle development cycle. The instant inventors discovered that in a transgenic mouse model, when Gdnf is over-expressed under the Cathespin L promoter, it affects the hair follicle growth in mice. Further analysis suggested that the effect of GDNF on the hair follicles in these mice was possibly due to expression of Gdnf in cells expressing endogenous Cathespin L gene, cells of the outer and inner root sheath and is essential for regular hair follicle morphogenesis and cycling.

Hair grows in cycles of various phases: anagen is the growth phase; catagen is the involuting or regressing phase (also termed "apoptosis-driven regression"); and telogen, the resting or quiescent phase (see e.g., Stenn and Paus (2001) "Controls of Hair Follicle Cycling". *Physiological Reviews* 81 (1): 449-494 and Paus et al., "The biology of hair follicles", *NEJM* 1999, 341:491-497). The time these phases last varies from person to person. Different hair color and follicle shape affects the timings of these phases. anagen phase, 2-3 years (e.g., approximately 3 years, occasionally much longer); catagen phase, 2-3 weeks; and telogen phase, around 3 months.

Each phase has several morphologically and histologically distinguishable sub-phases. Prior to the start of cycling is a phase of follicular morphogenesis (formation of the follicle). There is also a shedding phase, or exogen, that is independent of anagen and telogen in which one of several hair that might arise from a single follicle exits. Normally up to 90% of the hair follicles are in anagen phase while, 5-15% (or 10-14%) are in telogen and 1-2% in catagen. The cycle's length can vary depending on location on different parts of the body.

Anagen is the active growth phase of hair follicles. The root of the hair are dividing rapidly, adding to the hair shaft. During this phase the hair grows about 1 cm every 28 days. Scalp hair stays in this active phase of growth for 2-7 years. The amount of time the hair follicle stays in the anagen phase is genetically determined. At the end of the anagen phase an unknown signal causes the follicle to go into the catagen phase.

The catagen phase is a short transition stage that occurs at the end of the anagen phase. It signals the end of the active growth of a hair. This phase lasts for about 2-3 weeks while the hair converts to a club hair. A club hair is formed during the catagen phase when the part of the hair follicle in contact with the lower portion of the hair becomes attached to the hair shaft. This process cuts the hair off from its blood supply and from the cells that produce new hair. When a club hair is completely formed, about a 2 week process, the hair follicle enters the telogen phase.

The telogen phase is the resting phase of the hair follicle. During telogen, the resting hair remains in the follicle until it is pushed out by growth of a new anagen hair. In most people, 5-15% of the hair on the scalp is in telogen at any given time. Shedding does not occur until the new anagen hairs begin to grow. The emerging hairs help to force the resting hairs out of the follicle. Recent evidence suggests that the mechanism of shedding of a telogen hair is an active process that may occur independent of the emerging anagen hair. When the body is subjected to extreme stress, as much as 70 percent of hair can prematurely enter a phase of rest, called the telogen phase. This hair begins to fall, causing a noticeable loss of hair. This condition is called telogen effluvium (see below). Telogen effluvium is a form of nonscarring alopecia characterized by diffuse hair shedding, often with an acute onset. Telogen effluvium can affect hair on all parts of the body, but, generally, only loss of scalp hair is symptomatic. Understanding the pathophysiology of telogen effluvium requires knowledge of the hair growth cycle (as detailed herein.) The club hair is the final product of a hair follicle in the telogen stage, and is a dead, fully keratinized hair. Fifty to one-hundred club hair are shed daily from a normal scalp.

The symptom of both acute and chronic telogen effluvium is increased hair shedding and diffuse hair loss from the entire scalp. Acute telogen effluvium is defined as hair shedding lasting less than 6 months. Patients usually only complain that their hair is falling out at an increased rate or that the remaining hair feels less dense. Causes for telogen effluvium and acute hair shedding can be physiologic stress, papulosquamous diseases of the scalp such as psoriasis and seborrheic dermatitis, allergic contact dermatitis, immunizations, severe infections (HIV), acute illness such as febrile illness, major surgery and severe trauma as well as chronic illness such as malignancy, particularly lymphoproliferative malignancy, systemic lupus erythematosus, end-stage renal disease, or liver disease, hormonal changes such as pregnancy and delivery (can affect both mother and child), hypothyroidism, discontinuation of estrogen-containing medications; changes in diet like crash dieting, anorexia, low protein intake, and chronic iron deficiency, heavy metals such as selenium, arsenic, and thallium. Acute telogen effluvium can occur in either sex, but because hormonal changes in the postpartum period are a common cause of telogen effluvium, women may have a greater tendency to experience this condition. Patients with acute telogen effluvium usually complain of relatively sudden onset of hair loss. If greater than 25% of extracted hairs are in telogen, the diagnosis of telogen effluvium is confirmed. However, each patient's scalp hair has an individual characteristic growth cycle. There are patients who have a very long anagen phase and a small proportion of hair in telogen at any given time. Telogen effluvium can be caused by medications, such as beta-blockers, anticoagulants, retinoids (including excess vitamin A), propylthiouracil (induces hypothyroidism), carbamazepine, and immunizations.

V. Methods of Treatment

The instant invention features the use of GDNF for treatment in cases where wound healing and/or hair growth is desired. In one embodiment, the invention features a method of promoting cutaneous wound healing in a subject, which includes the step of administering at a wound site on the subject a composition comprising a therapeutically effective dose of GDNF, or a biologically active fragment thereof, and (optionally) repeating the administration for a time period sufficient to promote said cutaneous wound healing.

As defined herein, the phrase "cutaneous wound healing" refers to wound healing of the skin, in particular, the skin of a mammal. "Cutaneous wound healing" is also referred to in the art as "dermal wound healing." Cutaneous wound healing is quite distinct from, for example, corneal wound healing. For example, the phases and sequence of events occurring in these type of wound healings differ. Moreover, the goals of these types of wound healing differ, for example, in the desired endpoint. Notably, one of the most crucial aspects of corneal wound healing is how the healing process aims to minimize end results such as vascularization and scar formation (which would have serious visual consequences). By contrast, such processes are significant desired end results of wound healing in other parts of the body, in particular, vascularization.

Administration is preferably topical administration but can also be achieved by injection of GDNF compositions of the invention at the wound site. In preferred embodiments, the wound site is external, e.g., on or in the skin of the subject. In exemplary embodiments, the wound site is an incision, a laceration, an abrasion, a puncture wound, a penetration wound, a surgical wound, an ulceration, a burn, a contusion, a hematoma, or a crush injury. In the case of topical administration, a GDNF composition of the invention can further include at least one anti-inflammatory agent. Alternatively, a GDNF composition of the invention can further include at least one antibiotic. Alternatively, a GDNF composition of the invention can further include at least one other wound healing-promoting agent.

In exemplary aspects of the invention, administration of GDNF composition is repeated for a time at least sufficient to promote filling and re-epithelialization of a wound site. In preferred aspects of the invention, administration of GDNF composition is repeated for a time at least sufficient to reestablish a skin barrier at the wound site.

In exemplary aspects, formulations of GDNF can contain at least about 1 ng/ml and up to about 10 µg/ml (e.g., for cosmetic applications), at least about 10 µg/ml and up to about 100 µg mg/ml or even 1 mg/ml (e.g., for wound healing and/or hair growth applications). In other exemplary aspects, a therapeutically effective dose consists of an amount of GDNF administered in a set period of time (e.g., daily), and routinely repeated over time (e.g., over weeks or months) to get the desired therapeutic effect. For example, GDNF compositions can be used at the concentration recited above and administered in a therapeutically effective dose (e.g., 1-100 ng daily, 100 ng to 1 µg daily, 1-50, 50-100, or 100-500 jig daily, 100 or 500 jig, up to 1 mg daily, 1-10 mg daily, 10-20 mg daily, 20-30 mg daily, 30-40 mg daily, or more. In some embodiments, a GDNF composition is administered daily. In other embodiments, a GDNF composition is administered multiple times a day e.g., twice or three times daily. The skilled artisan will readily appreciate that doses can be significantly lower if the compositions are to be administered via a controlled release system or formulation. For example, doses in the ng/ml or even pg/ml range are possible in the case of controlled release systems or formulations.

In other aspects, the invention features methods for promoting hair growth on a subject which includes the step of administering at site of desired hair growth on the subject (e.g., at a skin site where hair follicles grow) (e.g., on a scalp) a composition comprising a pharmaceutically effective dose of isolated GDNF, or a biologically active fragment thereof, and repeating the administration for a time period sufficient to promote said hair growth on said subject.

As a measure of efficacy, a pharmaceutically effective dose is a dose sufficient to promote a 5%, 10%, 15%, 20%, 25% increase in hair follicle number (or follicular units) over a period of several weeks to several months. Preferably, a pharmaceutically effective dose is a dose sufficient to promote a 10% increase in hair follicle number (or follicular units) over a period of several weeks to several months. Even more preferably, a pharmaceutically effective dose is a dose sufficient to promote a 50% (or more) increase in hair follicle number (or follicular units) over a period of several weeks to several months. In exemplary embodiments, the method of promoting hair growth involves administration of a GDNF composition via topical contacting at a skin site containing hair follicles (or a skin site that normally contains hair follicles). A skin site for hair growth can be virtually anywhere on the body except, for example, the soles of the feet and the palms of the hands, the lips, and the eyelids, apart from eyelashes.

As an alternative, efficacy of treatment can be monitored according to any art-recognized means for evaluating hair loss in a subject. Without being bound in theory, it is proposed that the methods of the invention can reduce hair shedding, for example, to a normal level. Exemplary non-invasive methods for monitoring hair loss include daily hair counts, standardized wash test, and the like (e.g., questionnaires, 60-s hair count, global photographs, dermoscopy, hair weight, contrasting felt examination, hair feathering test, phototrichogram and TrichoScan), which are good methods for primary evaluation of the patient and to get an approximate assessment of the amount of shedding. While not preferred, semi-invasive methods, e.g., Trichogram and unit area trichogram (UAT), and/or invasive methods, e.g., scalp biopsy, can also be used to measure hair loss (and, indirectly, hair growth.). For a detailed description of these procedures, see e.g., Dhurat, R. and Saraogi, P. 2009 *Int J Trichology* 1 (2): 108-119.

As a measure of efficacy, a pharmaceutically effective dose is a dose sufficient to promote a 5%, 10%, 15%, 20%, 25% decrease in hair loss over a period of several weeks to several months. Preferably, a pharmaceutically effective dose is a dose sufficient to promote a 10% decrease in hair loss over a period of several weeks to several months. Even more preferably, a pharmaceutically effective dose is a dose sufficient to promote a 50% (or more) decrease in hair loss over a period of several weeks to several months.

In exemplary embodiments, the hair growth promoting methods of the invention are used to treat androgenetic alopecia (AGA), also known as male pattern baldness or female pattern baldness. In other embodiments, the hair growth promoting methods of the invention are used to treat autoimmune alopecia. This disease interferes with the hair growth cycle by causing a follicle to prematurely leave the anagen, or active growth, phase and enter the resting, or telogen phase. The hair growth in the affected follicles is lessened or stopped completely.

In other embodiments, the hair growth promoting methods of the invention are used to treat hair shedding. In other embodiments, the hair growth promoting methods of the invention are used to treat hair thinning. In yet other embodiments, the methods of the invention are used to treat acute or chronic telogen effluvium. In still other embodiments, the methods of the invention are used, generally, to treat scalp hair loss, hair thinning or baldness (poor hair thickness, poor hair growth). In yet another embodiment, the methods of the invention are used to extend the life or otherwise improve the condition of hair implants.

In other embodiments, the methods of the invention are used to treat iatrogenically-induced hair loss, for example, scalp hair and/or eye brow hair loss in chemotherapy patients. As used herein, the phrase "iatrogenically-induced" refers to a condition or disease state caused by a physician, surgeon, or other administering professional or by a medical or surgical treatment (e.g., pharmaceutical treatment, chemotherapeutic treatment, radiation treatment) or a diagnostic procedure.

In some embodiments, the GDNF compositions of the invention can be used in combination with one or more additional agents, e.g., art-recognized agents that promote wounds healing or hair growth and/or reduce hair loss. For example, the GDNF compositions of the invention might be used in combination, or in a combination therapy, with any one (or more than one) of the following agents: Combination platelet-derived growth factor (PDGF), interleukin-1 (IL1), nerve growth factor (NGF) or proNGF, keratinocyte growth factor (KGF), thymic peptides of the families of thymulin, thymosin alpha-1 and thymosin beta-4 (see e.g., US20110281802A1). Combination treatment can include, in other embodiments, coincident oral treatment with, for example, vitamins; combination of vitamin B1, vitamin B6, vitamin B12, folic acid, magnesium glycinate, L-cysteine, biotin, ferric glycinate, *Polygonum multiflorum*, and/or *Emblica officinalis* (see e.g., US20130017285); insulin, insulin-like growth factor (IGF) (see e.g. US20100172865; Yoon et al. 2011, PLoS ONE 6(12): e28474), and/or polyamines (see e.g., Ramot et al. 2011, PLoS ONE 6(7): e22564). In some embodiments, the GDNF compositions of the invention can be used in combination with an electrical stimulus or mechanical stimulus (see e.g., Yoon et al. 2011, PLoS ONE.)

Without being bound in theory, it is also believed that GDNF, or a biologically active fragment thereof, can be administered to subjects via a gene therapy approach, for example, in cases where healing of chronic wounds is desired. GDNF-encoding nucleic acids can be engineered into appropriate expression vectors and targeted to areas requiring continued supply of expressed GDNF. Expression vectors can be engineered to encode GDNF, or a biologically active fragment thereof, in the context of a fusion protein, for example, fuse with a receptor targeting means for achieving entry into cells of the skin. Also, vectors can be formulated with agents that promote entry of nucleic acid molecules into skin.

VI. Other Uses

Chronic Wound Healing

The instant invention also features the use of GDNF for treatment in cases where a subject suffers from chronic nonhealing wounds. Experts debate about the time for closure that defines a chronic nonhealing wound as compared to that required for closure of an acute wound. Dealey, C, 3rd ed. Blackwell Publishing Ltd., 2005; Whitney, J. D., *Nurs. Clin. North Am.* 40:191-205, 2005; Bryant, R A., et al, *Acute and Chronic Wounds, Current Management Concepts*. 4th ed. Mosby, 2011. It has been stated that "acute wounds generally follow trauma or inflammation and usually heal within six weeks." Kumar, S., et al., *Surgery* 26:43-47, 2008. Chronic wounds (in addition to failing to heal after six weeks) have characteristic pathological associations that inhibit or delay the healing process. Jones, K. R., et al., *Adv. Skin Wound Care* 20:591-600, 2007.

Chronic wound healing is mainly sustained by chronic inflammation, which without appropriate therapy tends to worsen. The basic reasons are not necessarily old age but rather hypertension and atherosclerosis, which can lead to ischemia, diabetes, and venous insufficiency. Common pathogenetic causes are local tissue hypoxia, edema, abundant bacterial colonization, and, possibly, repeated ischemia-reperfusion injuries. The surface area of a nonhealing wound tends to widen and shows fibrin deposition, necrotic areas, and a few islands of granulation tissue. It is estimated that, in the industrialized world, 1-1.5% of the population experience problems related to recovering proper skin function. The problem is particularly prominent in elderly and diabetic patients, or those with arteriosclerosis.

Common chronic wounds include, but are not limited to pressure ulcers, venous ulcers, and the like. Pressure ulcers, also known as decubitus ulcers or bedsores, are localized injuries to the skin and/or underlying tissue usually over a bony prominence, as a result of pressure, or pressure in combination with shear and/or friction. Most commonly this will be the sacrum, coccyx, heels or the hips, but other sites such as the elbows, knees, ankles or the back of the cranium can be affected. The cause of pressure ulcers is pressure applied to soft tissue so that blood flow to the soft tissue is completely or partially obstructed. Shear is also a cause; shear pulls on blood vessels that feed the skin. Pressure ulcers most commonly develop in persons who are not moving about or are confined to wheelchairs. Pressure ulcers can be very difficult to prevent in critically ill patients, frail elders, wheelchair users (especially where spinal injury is involved) and terminally ill patients. Venous ulcers (stasis ulcers, varicose ulcers, or ulcus cruris) are wounds that are thought to occur due to improper functioning of venous valves, usually of the legs. The exact etiology of venous ulcers is not certain, but they are thought to arise when venous valves that exist to prevent backflow of blood do not function properly, causing the pressure in veins to increase. They are a major cause of chronic wounds, occurring in 70% to 90% of chronic wound cases. Venous ulcers develop mostly along the medial distal leg, and can be very painful.

Burn Wounds

The instant invention also features the use of GDNF for treatment in cases where a subject suffers from burn wounds. Most burn wounds affect only the skin (epidermal tissue). Rarely, deeper tissues, such as muscle, bone, and blood vessels can also be injured. Burns are described according to the depth of injury to the dermis and are loosely classified into first (involving the epidermis), second (extending into superficial (papillary) dermis and/or extending into deep (reticular) dermis), third (extending through entire dermis), and fourth (extending through skin, subcutaneous tissue and into underlying muscle and bone) degrees. Burns are caused by a wide variety of substances and external sources such as exposure to chemicals, friction, electricity, radiation, and heat. Generally, the methods of the invention are suited to the treatment of first through third degree burns.

Freezing Injury

The instant invention also features the use of GDNF for treatment in cases where a subject suffers from freezing injury, in particular, from wounds or tissue damage resulting from freezing injury. An exemplary freezing injury is frostbite. Frostbite is the medical condition in which localized damage is caused to skin and other tissues due to freezing. Frostbite is most common in body parts farthest from the heart and those with large exposed areas. Frostbite involves tissue destruction. Second-degree injury usually involves blisters (appearing 1-2 days after tissue becoming frozen.) The blisters may become hard and blackened, with time. Most of the injuries heal in one month, but the area may become permanently insensitive to both heat and cold. The GDNF treatment methodologies of the invention are suited for treatment of tissue damage, blisters, wounds and the like associated with frostbite and other freezing injuries.

Diabetics

Diabetes mellitus is well known for its skin complications, usually leading to the formation of chronic debilitating ulcers (Levin, M. E. 1995, *Diabetes Care* 18, 1383-94; Cavanagh, P. R., et al. 1998, *Ostomy Wound Manage* 44, 6S-12S; Brem et al., 2003). Wound-healing impairment is characterized by the inability of the healing process to progress, thus leaving the wound susceptible to external infections as well as to deterioration of the underlying tissue, leading to morbidity and sometimes requires amputation (Brem, H. et al. *Surg Technol Int* 11, 161-7 (2003); Freedman, H., et al. *Am J Surg* 188, 31-5 (2004); Mousley, M. *Nurs Times* 99, 70-4 (2003); Wertheimer, E. *Isr Med Assoc J* 6, 287-9 (2004)). Accordingly, the instant invention also features the use of GDNF for treatment in cases where a subject suffers from ulcers associated with diabetes. In exemplary embodiments, the invention features use of GDNF for treatment of "diabetic foot ulcer" and/or "non-healing chronic diabetic ulcers."

Cosmetic Applications

Without being bound in theory, it is proposed that the GDNF compositions of the invention may have utility in the field of cosmetic applications, e.g., in dermatological application. For example, the GDNF compositions of the invention could be useful as. "antiaging" substances and/or may improve the appearance of wrinkles. It was noted in the wound healing experiments, described herein, that mice exhibited smoother skin following GDNF treatment. Other research on wound healing has produced much evidence showing the importance of peptides in improving the signs of aging (Lupo M P, Cole A L. Dermatol Ther. 2007; 20:343-349). Thus, in exemplary embodiments, the GDNF peptides of the invention can be used in methods to improve fine lines, skin texture, and/or hyperpigmentation in addition to their uses to influence wound healing. It is important for such application that the/protein peptide is stable in formula, deliverable to its target dermal site, and biologically active at this target site (Lupo M. *Dermatol Surg.* 2005; 31:832-836).

Screening Assays

In other aspects, the invention features the use of GDNF peptides/proteins in screening assays, e.g., in screening assays for compounds that modulate one or more of the biological activities of GDNF in the processes of wound healing and/or hair growth. In one embodiment, the invention features contacting a composition comprising GDNF with a test compound and determining the ability of the test compound to upregulate, e.g., increase or enhance, the activity of GDNF (or a biologically active fragment thereof) such that a compound having the potential to increase hair growth or improve wound healing is identified. In another embodiment, the invention features contacting a cell expressing GNDF with a test compound and determining the ability of the test compound to upregulate, e.g., increase or enhance, the expression or activity of GDNF (or a biologically active fragment thereof) such that a compound having the potential to increase hair growth or improve wound healing is identified. In exemplary embodiments, the cell is a cell known in the art to play a role in wound healing and/or hair growth. A multitude of screening assay formats art known in the art and it is contemplated that screening assays of the invention can make use of labeled reagents, e.g., labeled GDNF proteins, unlabeled reagents, immobilized reagents, and the like. High throughput formats are also well known in the art and are contemplated as a preferred embodiment for the screening assays of the invention.

VI. Pharmaceutical Compositions and Formulations

In other aspects, the invention features pharmaceutical formulations that include a therapeutically effective dose of isolated GDNF, or a biologically active fragment thereof, formulated in combination with at least one agent which facilitates administration of said GDNF, or a biologically active fragment thereof.

Topical formulations are often prepared in the form of emulsions. The term "emulsion," as used herein refers to mixtures of two or more liquids, which may be in the form of a continuous phase and a disperse phase, for example. Exemplary emulsions may be in the form of creams, lotions, ointments, gels, etc. and may include, for example, oil-in-water emulsions, water-in-oil emulsions, multiple emulsions and microemulsions. These formulations will be prepared which contain from about 0.001 to 10 w/w % of the GDNF compositions of the present invention. These formulations will then be administered or applied to the desired areas, e.g., from 1 to 4 times daily. Alternatively, these formulations will be administered or applied to the desired areas less frequently, i.e., from 1 to 5 times a week. Formulations can be applied or administered, for example, every other day, every third day, and so forth. Administration or application may vary in frequency over the course of treatment.

The GDNF compositions may also be administered topically in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A potential formulation for topical delivery of the hair treatment compositions used in the methods of the present invention utilizes liposomes such as described in U.S. Pat. Nos. 4,911,928 and 5,834,014.

Carriers for systemic administration include, for example, sugars, starches, cellulose and its derivatives, malt, gelatin, talc, calcium sulfate, vegetable oils, synthetic oils, polyols, alginic acid, phosphate buffer solutions, emulsifiers, isotonic saline and pyrogen-free water. Suitable carriers for parenteral administration include, for example, propylene glycol, ethyl oleate, pyrrolidone, ethanol, and sesame oil.

In exemplary embodiments, the GDNF compositions of the invention are formulated in gels or in nanoparticles. Exemplary gels include, for example, carboxymethylcellulose-based gels. Further exemplary gel formulations include, but are not limited to, polymeric gel formulations, in particular, those comprising a polymer selected from the group consisting of vinyl polymers, polyoxyethylene-polyoxy propylene copolymers, polysaccharides, proteins, poly(ethylene oxide), acrylamide polymers and derivatives or salts thereof. Such gel formulations are described in, e.g., U.S. Pat. No. 5,705,485; formulation with nanoparticles.

In other exemplary embodiments, the GDNF compositions of the invention are formulated in heparin, heparan sulphate (see e.g., US Application 2010/0056440), hyaluronic acid, lactic acid or in glycolic acid. In other exemplary embodiments, the GDNF compositions of the invention are formulated in combination with polymeric compounds (such as polylactic acid, polyglycolic acid, poly(lactide-co-glycolide) (PLGA) microparticles, etc.) or in liposomes. In yet other exemplary embodiments, the GDNF compositions of the invention are formulated in collagen-coated delivery systems or in combination with alginate, chitosan, lactide and/or lactide/glycolide copolymers. In yet other embodiments, the GDNF compositions of the invention are formulated as part of a topical dressing (e.g., within an adhesive bandage). In yet other embodiments, the GDNF compositions of the invention are formulated as slow release forms, in films (e.g., biodegradable or non-biodegradable firms. In yet other embodiments, the GDNF compositions of the invention are formulated in combination with PEG 400 or serum albumin (e.g., human serum albumin.)

In other exemplary embodiments, the GDNF compositions of the invention are formulated as hydrogel compositions, i.e., hydrogels or hydrogel formulations. In a preferred aspect of the invention, the hydrogels comprise GDNF. In a preferred aspect of the invention, the hydrogels comprise GDNF included within liposomes. Liposomes have been used in delivering bioactive compounds, for example, growth factors and/or cytokines, for therapeutics purposes due to low toxicity, lack of immune system activation and targeted delivery at the site of action.

In one aspect, the invention features a hydrogel composed of liposomes (e.g., liposomes including GDNF) and chitosan. Ogiso et al., have shown that the negatively charged liposomes diffuse to dermis and lower part of hair follicles, increasing the permeation of drug through the skin (Ogiso T, et al., (2001). J Drug Targeting.: 9, 49-59.) Chitosan, a natural polysaccharide polymer, has been used as a hydrogel mixed with liposomes to deliver growth factors at the injected site with slow release of the bioactive molecules. Earlier studies have shown that production of the vascular endothelial growth factor is up-regulated in wound healing when macrophages are activated by chitin/chitosan (review by Muzzarelli, see e.g., Muzzarelli, R A A. (2009) Carbohydrate Polymers: 76, 167-182). Moreover, Patel et al., have shown that GDNF-Chitosan blended nerve guides enhances both functional and sensory recovery in vivo (Patel M, et al., (2007). J tissue Eng. & Regenerative Med.: 1, 360-367). For further background, see e.g., Elcin Y M et al. (1996) Artif. Cell Blood Substit. Immobil. Biotechnol.: 24, 257-271

Accordingly, in one aspect, the invention features a therapeutic delivery system, e.g., a drug delivery formulation, comprising liposomes containing GDNF, formulated into a hydrogel, e.g., chitosan, for administration in a therapeutic regimen described herein, for example, for administration to a wound site, e.g., in wound healing aspects of the invention. In an exemplary embodiment, the invention features hydrogels made according to the following process. Growth factor or cytokine, e.g., GDNF is loaded into liposomes and then mixed with hydrogel agent, e.g., chitosan. Briefly, liposomes are dissolved in appropriate solvent or buffer and into a thin film (e.g., air and/or gas dried.) Dries films are then resuspended and filteres through appropriately sized filters to generate small unilamellar vesicles. Liposome-encapsulated growth factor/cytokine, e.g., GDNF can be prepared by sonication of the lipids and growth factor/cytokine in appropriate weight/weight ration. To generate hydrogels, liposome-encapsulated growth factor/cytokine, e.g., GDNF can be added to a solution, e.g., a prechilled solution) of hydrogel polymer, for example, chitosan (dissolved in appropriate solvent/buffer) by gentle stirring for an appropriate time before applying at the site of administration, e.g., at the wound site.

It will be recognized by the skilled artisan that the compositions so-formulated can also include inactive ingredients, for example, preservatives, stabilizers, solubilizers, and the like: sodium chloride, sodium acetate trihydrate, glacial acetic acid, water for injection, and methylparaben, propylparaben, and m-cresol as preservatives and 1-lysine hydrochloride as a stabilizer.

Exemplary inactive ingredients include, for example, buffer, for example, pH buffer e.g., sodium phosphate, potassium phosphate, histidine, or Tris-HCl, e.g., at a concentration of 10-50 mM; salt (for the purpose of tonicity modifier and solubilizer), e.g., NaCl and $CaCl_2$ at a concentration of 10-100 mM; sugar (for the purpose of protein-stabilizer, bulking agent, etc), e.g., sucrose or trehalose at a concentration of 10-100 mg/mL; polyol (for the purpose of tonicity modifier and bulking agent), e.g., mannitol or sorbitol at a concentration of 10-100 mg/mL; amino acid (for the purpose of tonicity modifier, bulking agent and stabilizer), e.g., glycine or arginine at a concentration of 10-100 mg/mL; polymer (for the purpose of bulking agent etc.), e.g., hydroxyethyl starch at a concentration of 10-50 mg/mL; surfactant (for the purpose of solubilizer, stabilizer and aggregation inhibitor), e.g., Tween-80, Tween-40, and/or SDS at a concentration of <1 mg/mL; preservative (for the purpose of antimicrobial preservation), e.g., benzyl alcohol or phenol e.g., at a concentration of 1-10 mg/mL; and/or antioxidant (for the purpose of antioxidant), e.g., ascorbic acid e.g., at a concentration of 1-10 mg/mL; and or other agents (with a purpose of protein-specific stabilization). Exemplary formulations are also described, for example, in U.S. Pat. No. 8,383,114.

Administration may be by periodic injections of a bolus of the pharmaceutical composition or may be made more continuous by intravenous or intraperitoneal administration from a reservoir which is external (e.g., an IV bag) or internal (e.g., a bioerodible implant). See, e.g., U.S. Pat. Nos. 4,407,957, 5,798,113, and 5,800,828, each incorporated herein by reference.

Examples of parenteral delivery systems include, but are not limited to, ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, hydrogels and transdermal patches. In some embodiments, compositions of the invention may be provided in lyophilized form as a dried powder or a cake.

In the case of injections of the GDNF compositions, GDNF proteins can be formulated in sterile physiological saline solution (e.g., 10 nM citrate and 150 mM sodium chloride), optionally including heparin, heparan sulphate, and/or glycerol.

In some embodiments, GDNF can be produced in *Escherichia coli* cells that contain an expression plasmid with a DNA insert encoding mature human GDNF. In such embodiments, it is preferred to engineer into the protein an N-terminal methionine.

The following examples illustrate the preparation of certain specific compounds according to the present technology. A skilled artisan appreciates that the invention is not limited to the exemplary work described or to the specific details set forth in the examples.

A skilled artisan further appreciates that the experimental conditions depicted in the following examples can be varied by as much as 2%, 5%, 10% or 20% above or below the listed amount, temperature, concentration, pH, time and rpm in order to optimize the conditions to achieve the desired results from the experiments.

EXAMPLES

Example 1: Transgenic Overexpression of GDNF

In a transgenic mouse model generated in the laboratory for a different hypothesis, when Gdnf is over-expressed under the Cathespin L promoter, it affects the hair follicle growth in mice. Further analysis suggested that the effect of GDNF on the hair follicles in these mice could be due to expression of Gdnf in cells expressing endogenous Cathespin L gene, cells of the outer and inner root sheath and is essential for regular hair follicle morphogenesis and cycling. Though we do not understand the mechanism how GDNF regulates hair follicle growth but Gdnf is expressed in embryonic skin where Gdnf mRNA is detected in both epithelial and mesenchymal components (Hellmich et al. 1996, Mech Dev 54: 95-105).

Transgenic mice were generated by microinjection a DNA construct comprising the Cathespin L promoter operably linked to the Gdnf cDNA Ctsl promoter driven Gdnf transgene contains a 3 kb genomic fragment upstream of the rat Ctsl translational start site. The numbering is relative to the Ctsl transcriptional start site, designated by +1. The coding sequence of Gdnf-Gfp fusion gene was cloned downstream of the promoter, using standard methods as described in Manipulating the Mouse Embryo: A Laboratory Manual, 3rd edition, Cold Spring Harbor Laboratory Press; 2002, ISBN-10: 0879695919. The Cathespin L promoter is described in Charron et al. 2003, Biol Reprod, 8 1(3), 1641-1648. When we analyzed the FVB transgenic mice Tg(Ctsl-Gdnf) we detected ruffled fur by 3 wk of age. We prepared paraffin skin sections stained with H&E. Analysis of such revealed an increased number of hair follicles adjacent to normal hair development compared to skin section from control littermate. This phenotype was reproducible in a different genetic background, using the mouse strain B6C3H. The transgenic mice expressing mouse Gdnf under Cathespin L promoter (Tg-Ctsl-Gdnf) were generated in the FVBN/J and B6C3HF1 strain.

Example 2: Accelerated Wound Healing of a Full-Thickness Wound

Figure 8A:
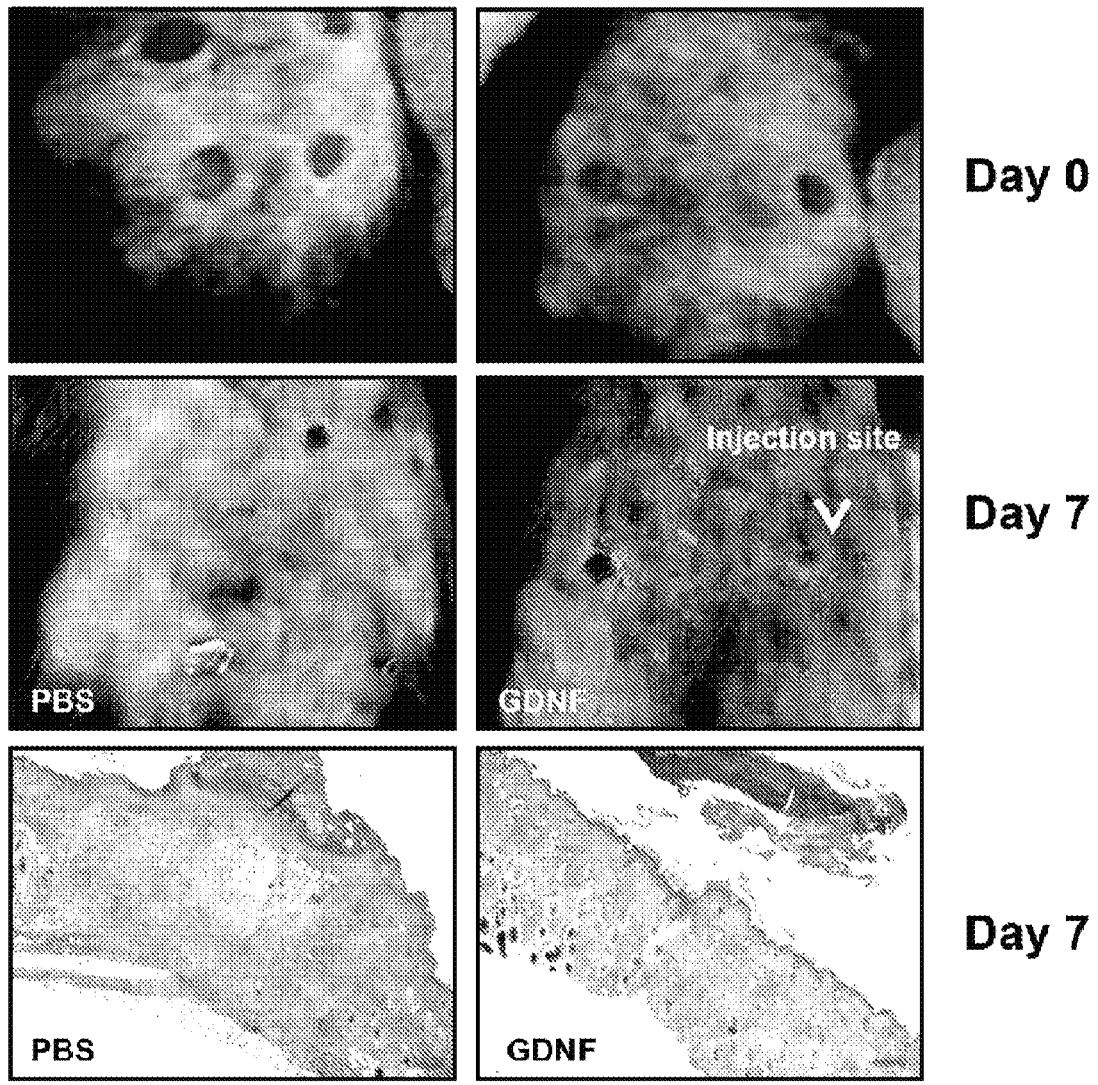
FIG. 8A-8B. GDNF accelerates wound-healing process in B6 wild type mice. Equal size 3 mm of wounds were made by biopsy punch needle on the dorsal side of adult mice. Wounds were photographed on day 0 and after one week. Only one wound site was injected with GDNF (arrow). H&E stained sections of wound sites injected with PBS or one injection of 0.1 ml of 0.5 mg/ml of GDNF. By one week all layers of skin, epidermis, dermis and hair follicles are present at the wound site injected with GDNF compared to PBS injected sites (A). In the GDNF injected site, a complete layer of epithelium is seen throughout the wound site (arrow) and new blood vessels (arrowheads) after 96 hr were as red blood cells are seen at PBS injected site (asterisk) (B).
Figure 8B:
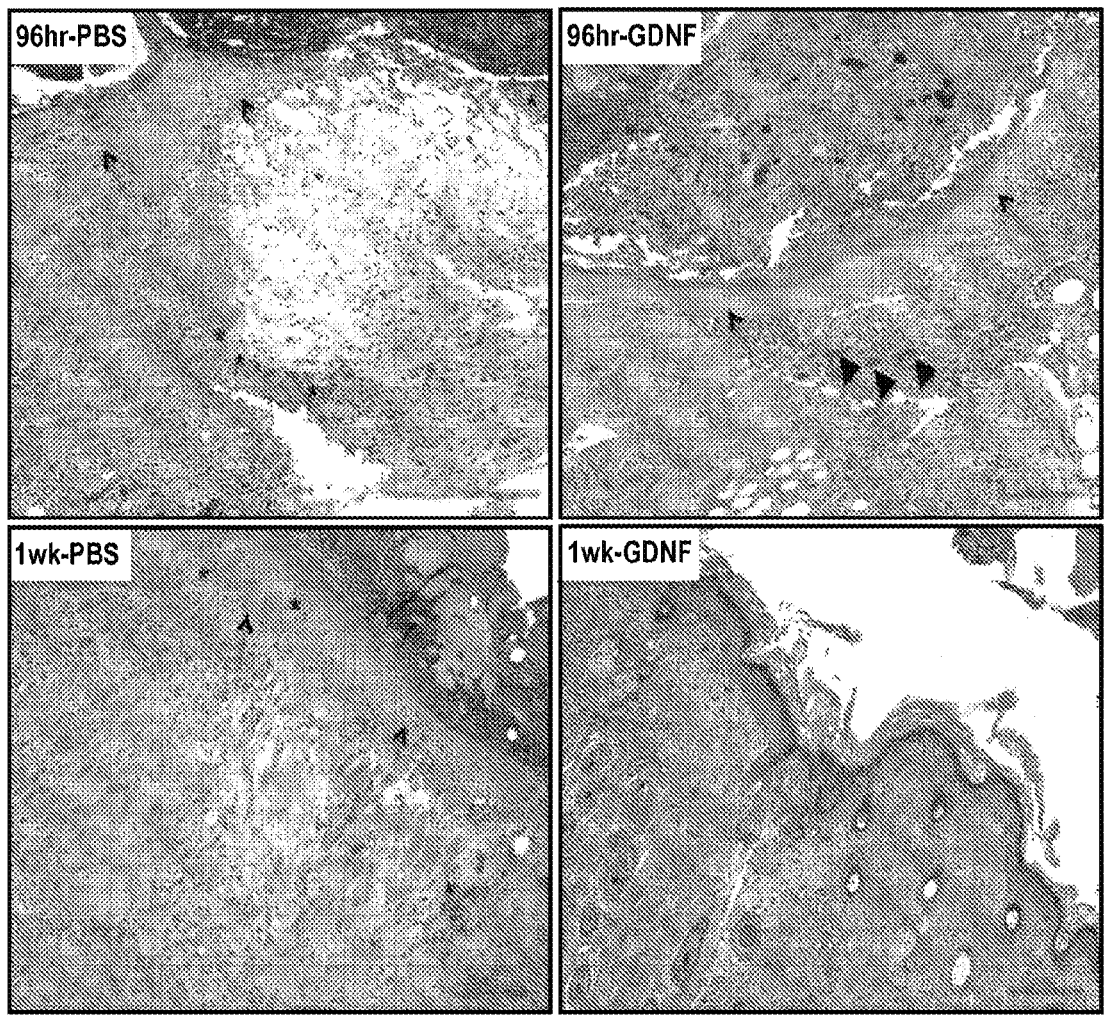
Figure 9:
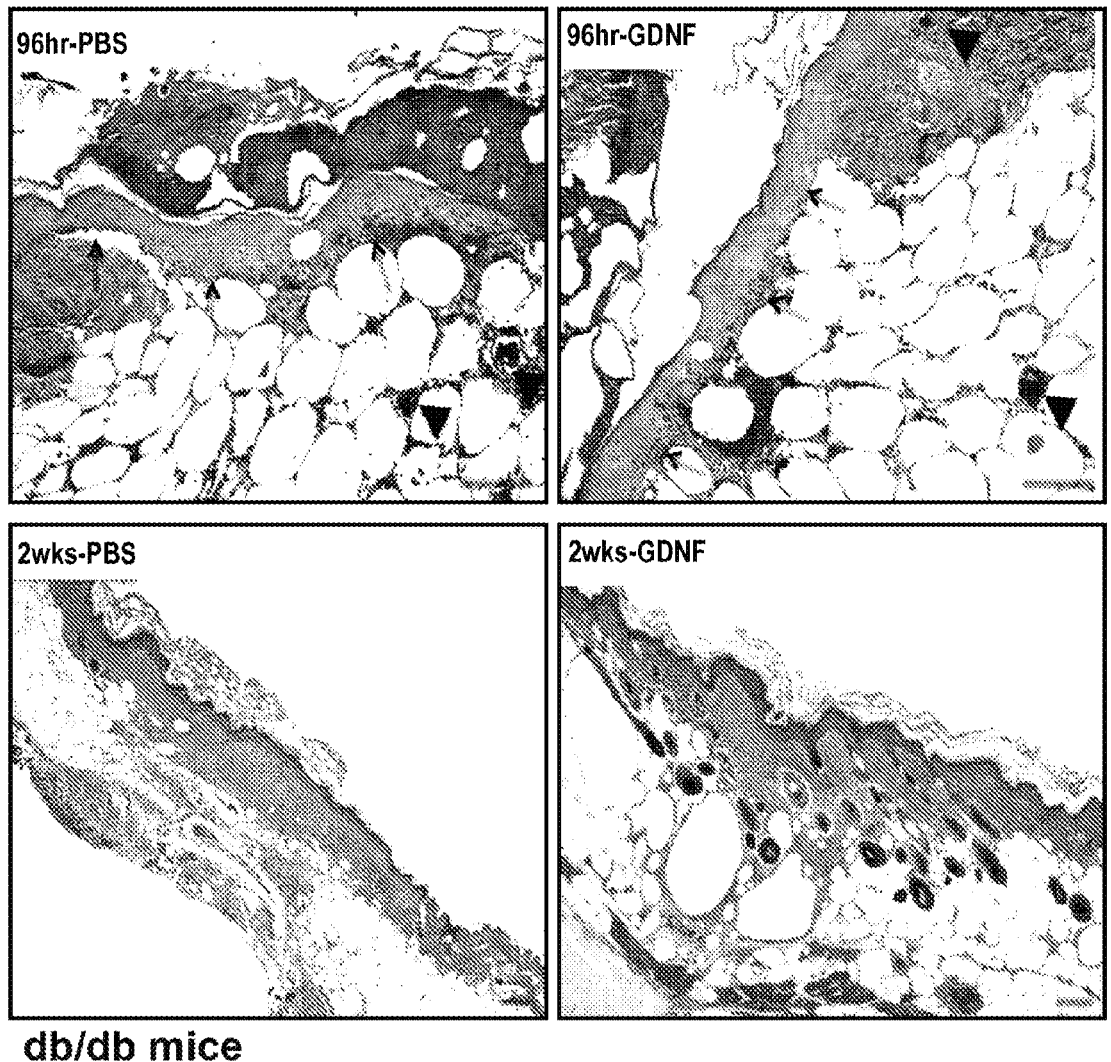
FIG. 9. GDNF accelerate the wound healing process in diabetic BKS.Cg-Dock7$^m$+/+Lepr$^{db}$/J mice. In the diabetic mice, re-epithelialization (arrow) and neovascularization and blood vessels (arrowhead) formation is observed as early as 96 hr. However, complete wound healing occurs after two weeks in the mice injected with 125 µg of GDNF. Scale=100 um FIG. 10. GDNF induces blood vessel growth in FVB mice. The figure shows an increased blood vessel growth and branching after injection of 50 µg GDNF (B) in comparison to the PBS control (A).
Figure 10:
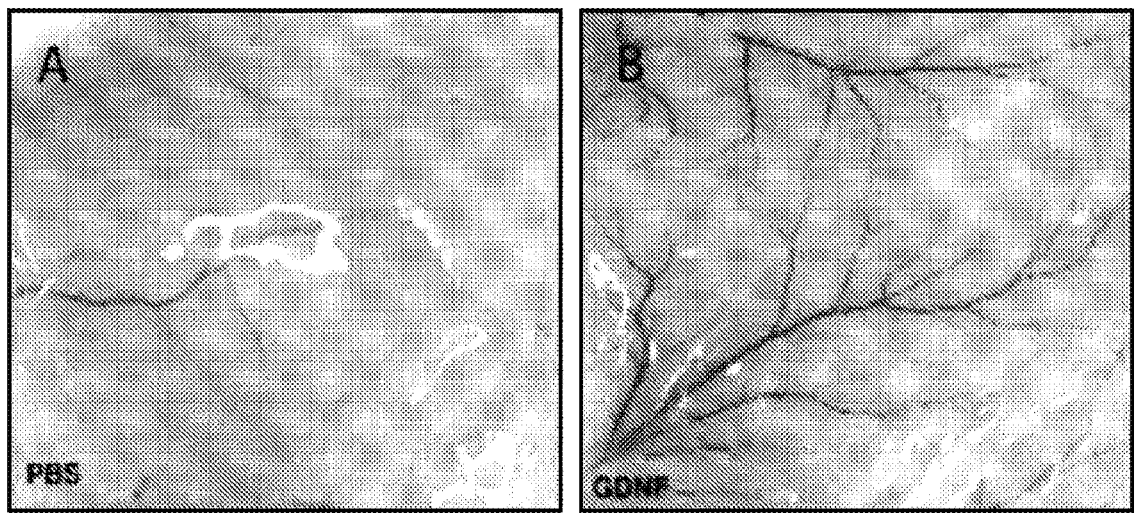

Wild type C57BL/6J (B6) or BKS.Cg-Dock7$^m$+/+Lepr$^{db}$ mice were anesthetized using isoflurane. Before wound setting, the hair was removed on the dorsal side using a clipper. Loose hair was removed with dry gauze dampened with 70% ethanol. Four 3 mm full skin wounds were made using a 3 mm biopsy punch needle. 100 µï of PBS or rat GDNF recombinant protein (Ser78-Ile21 1) from R&D system (cat no. 512-GF) at concentrations of 0.1 mg/ml or 0.5 mg/ml diluted in PBS was injected either at the wound site or subcutaneously in the middle of the 4 wounds using 30G needles, approximately 5-6 mm adjacent to the wounds. The mice were housed individually and monitored daily after surgery. Wound re-epithelialization and hair follicle development was determined by histology at 96 hrs, 6, 8, and 15 days after injection of the recombinant GDNF protein (FIGS. 8A, 8B and 9).

Example 3: Dose Comparisons for Hair Follicles

For the GDNF injections we tested one dose of 100 µï 0.5 mg/ml GDNF protein (R&D system, cat no. 512-GF) versus five 100 µï injections of 0.1 mg/ml GDNF on alternate days.

Figure 3:
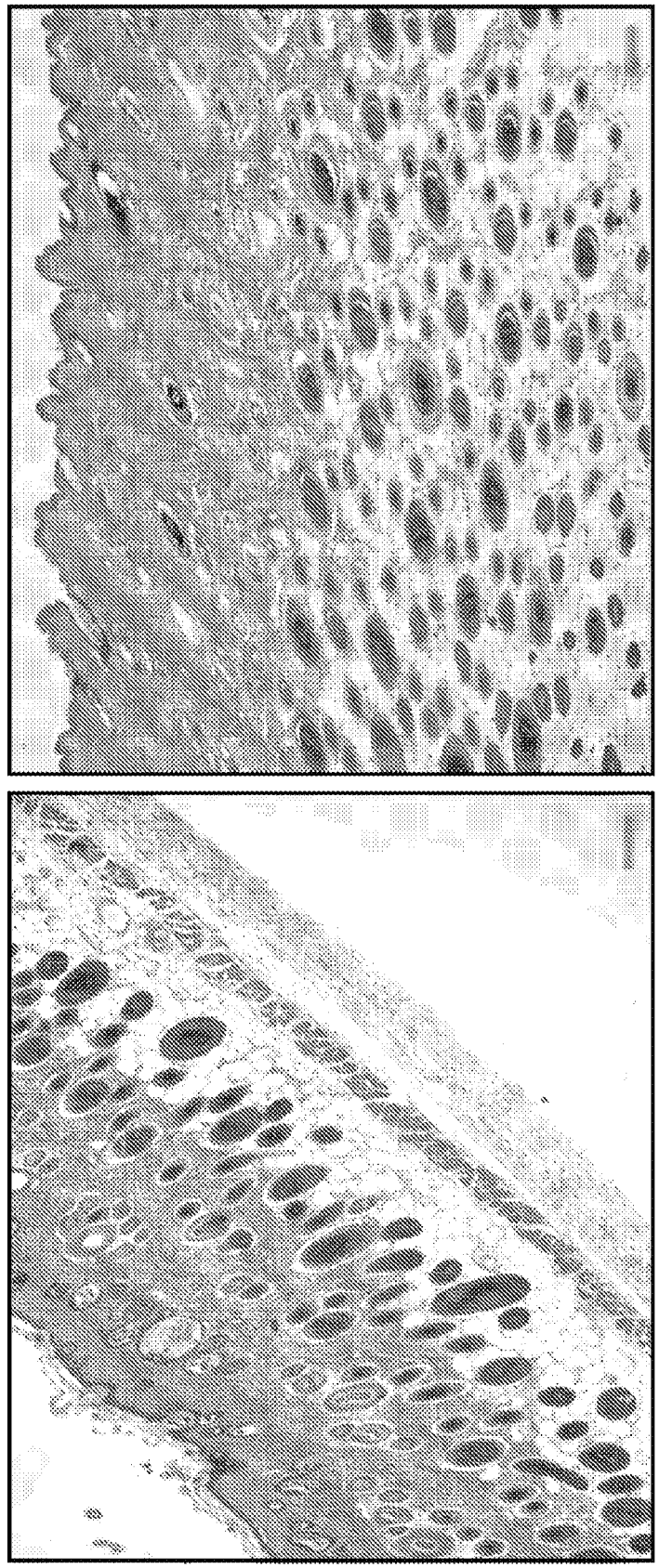
FIG. 3. Multiple injections of low dose are more effective than one injection of high concentration of GDNF. H&E image of skin from mouse injected with 100 ul of (A) or 5 injections of 100 ul of 0.1 mg/ml of GDNF on alternate days. Both images are at same magnification. Scale=100 um.
Figure 4:
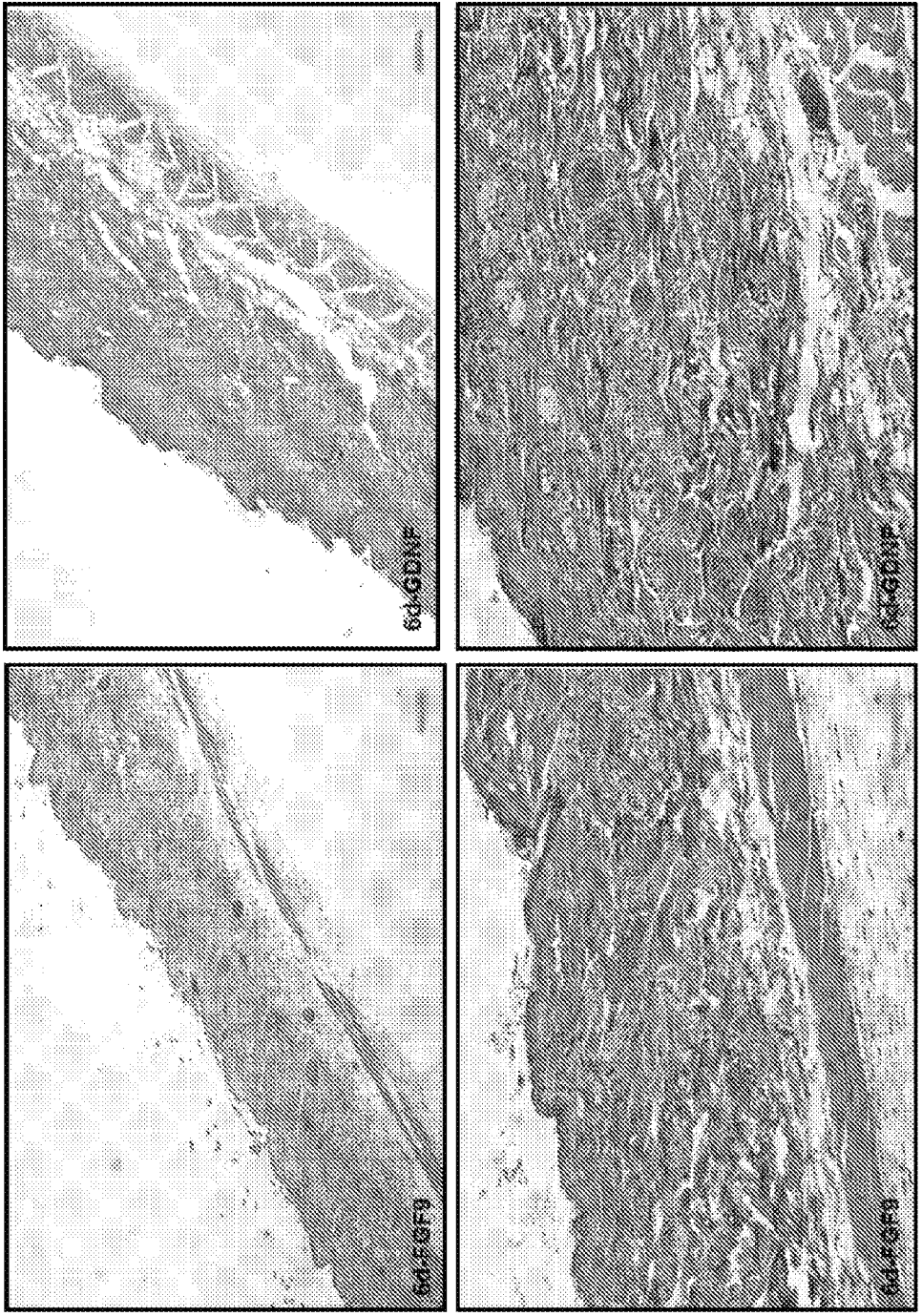
FIG. 4. New hair follicle development is specific to GDNF. Adult wild type B6 mice injected with 50 μg FGF9 or GDNF and analyzed after 6 days. There is an increased number of new hair follicles in sections from mice injected with GDNF. Scale=100 um.

Skin tissue was harvested 15 days after injection (day 15) and paraffin sections were prepared and stained with H&E. In both groups an increase of hair follicles was detected, but a more striking increase when GDNF was administered at the lower dose over five time points, with the hair follicles being in different developmental stages (FIG. 3).

Example 4: Dose Comparison for Hair Follicle Development

Figure 5:
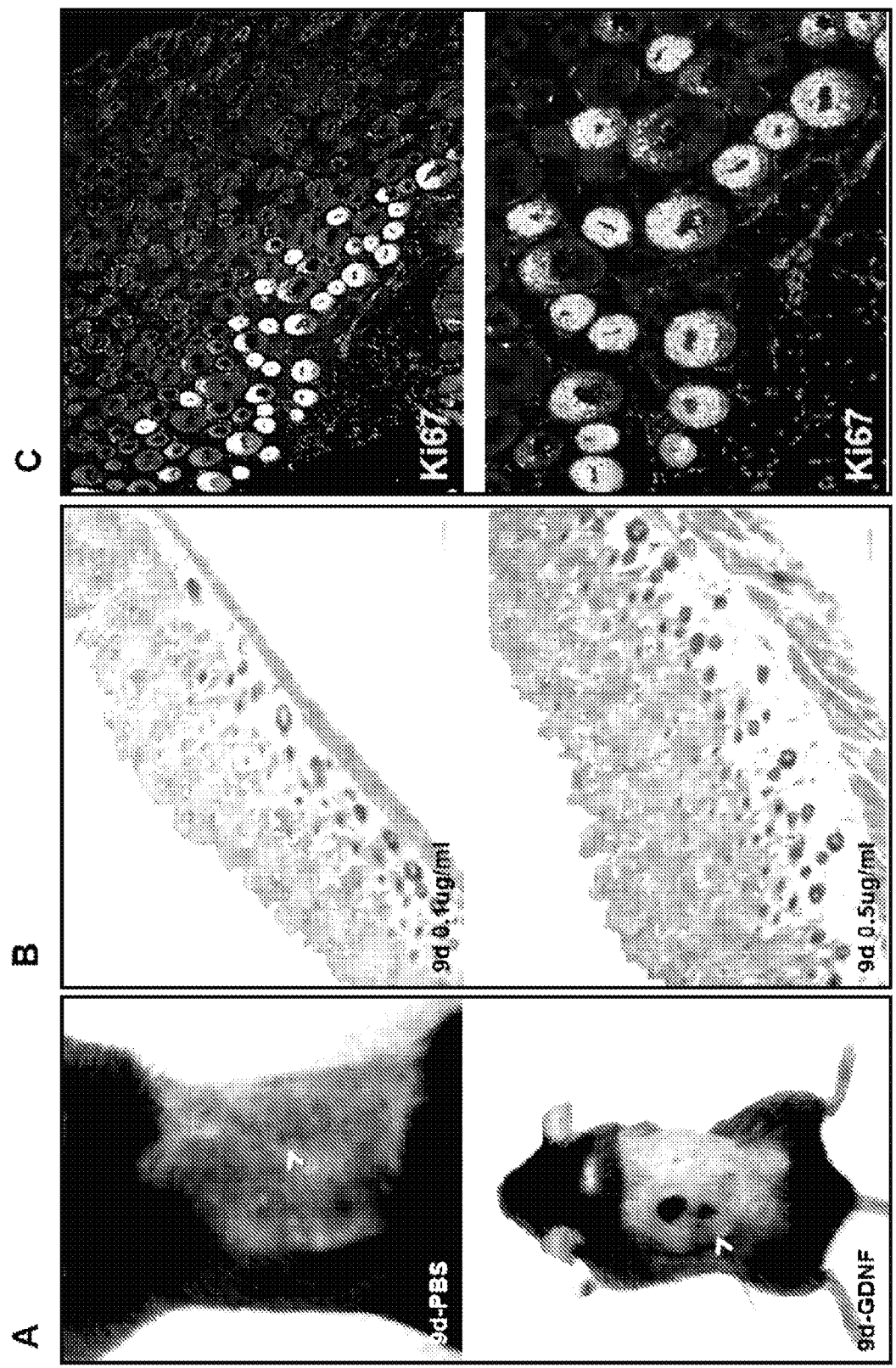
FIG. 5. Increased number of hair follicles at a higher dose GDNF. New hair follicles develop as early as day 9 in mice injected with 10 jag of GDNF compared to mice injected with PBS (A). By day 9 there are multiple layers of hair follicles in mice injected with 50 jag GDNF compared ones injected with 10 jag (B). Ki67 labeled cells in hair follicles of skin sections injected with GDNF (C).

Adult C57BL/6 (B6) wild type mice were injected with 100 µï of 0.1 mg/ml or mg/ml recombinant GDNF protein (R&D system, cat no. 512-GF). The skin was analyzed after 9 days. One injection of 0.1 mg/ml was sufficient to induce hair follicle development at the injection site by day 9 (FIG. 5A). With the higher dose of 0.5 mg/ml more hair follicles were detectable (FIG. 5B). The rate of proliferation was assayed by 5-Bromo-2'-deoxyuridine (BrdU) labeling (Sigma, cat. no. B5002) according the protocols described by Sanjay et al. 2008, Methods in Mol Biol 438, 335-343. For this BrdU was injected intraperitoneally (i.p.) one day before collecting the skin. Most of the new hair follicles in the GDNF group stained positively indicating that these are proliferating while (data not shown). Alternatively skin sectioned were immuno stained with Ki67 antibody, as Ki67 protein is an established marker for cell proliferation. Ki67 is expressed during active phase of the cell cycle G1, S and G2 and absent from resting cells GO. The staining of hair follicle cells with Ki67 antibody shows that they are in proliferative stage on day 9 after GDNF injection (FIG. 5C).

Figure 6:
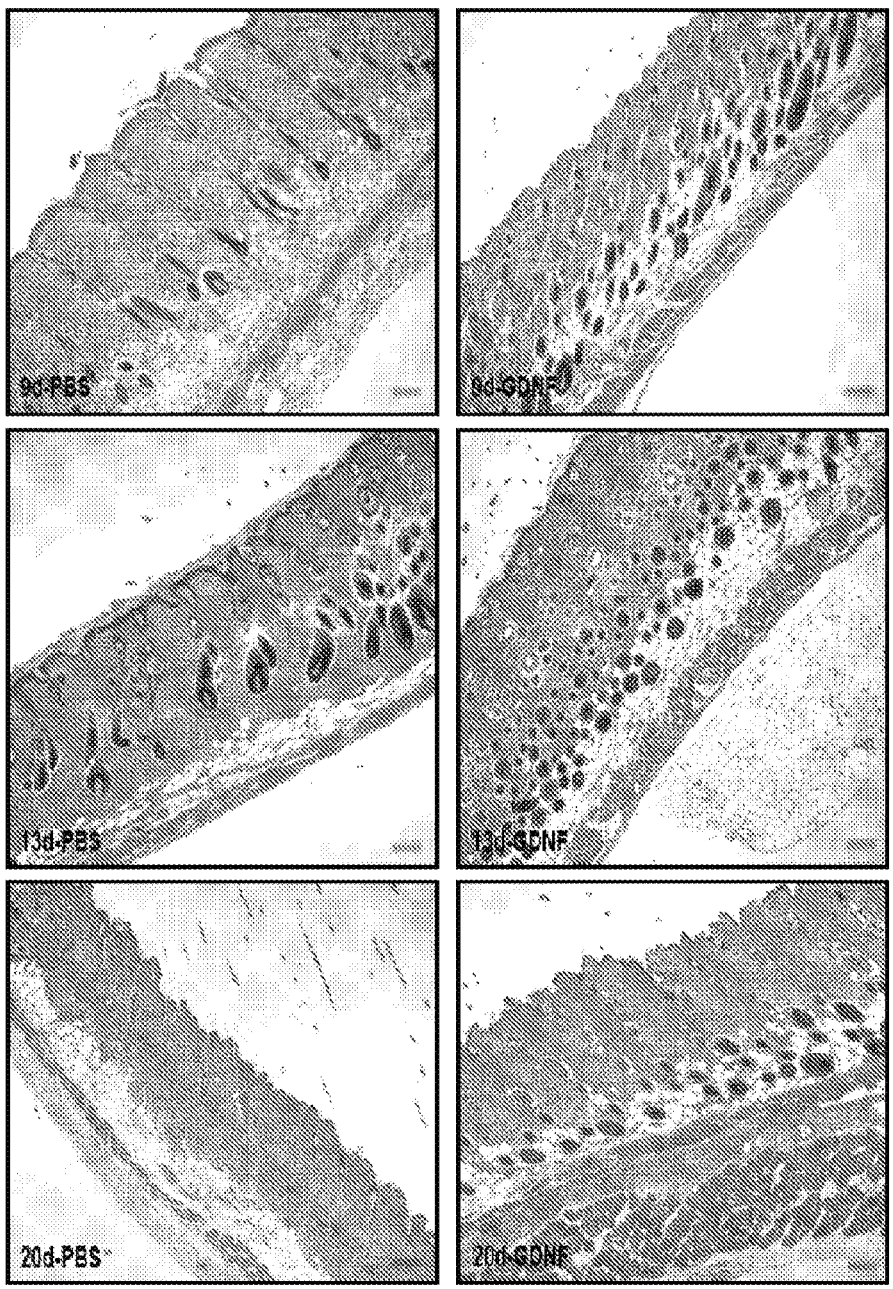
FIG. 6. Time course of hair follicle stimulation following GDNF treatment. Hematoxylin and eosin stained section of skin, injected (s.c.) with PBS or 50 jag of GDNF protein and analyzed after 9, 13, and 20 days. There are more numbers of hair follicles at the GDNF injected site compared to PBS. Scale=100 um FIG. 7. GDNF seems to be activating Notch1 signaling pathway. RT-PCR analysis on RNA extracted after 6 days from skin samples injected with 50 jag of GDNF or PBS in B6 wild type mice. Three fold increase in Notch1 but not c-Myc transcript was detected in GDNF injected sample. Transcript of Ret, the tyrosine kinase receptor, protein known to be in GDNF-GFRcc1 signaling complex, is 4 fold higher in GDNF injected skin.

Adult B6 mice were injected with 100 µï of PBS or 0.5 mg/ml of GDNF (all injections were on the dorsal side and subcutaneous (s.c.)) and skin was isolated at day 6, 9, 13, 15, 20, and 30 after injections, paraffin embedded and sectioned for histological analysis. A dramatic increase in hair follicle numbers was observed on day 9 and 13 compared to mice injected with PBS (FIG. 6). By day 20 hair regeneration is complete in mice injected with PBS. Surprisingly, hair follicles are still proliferating in the GDNF injected group (FIG. 6).

Example 5: GDNF Signaling in the Epidermis

Figure 7:
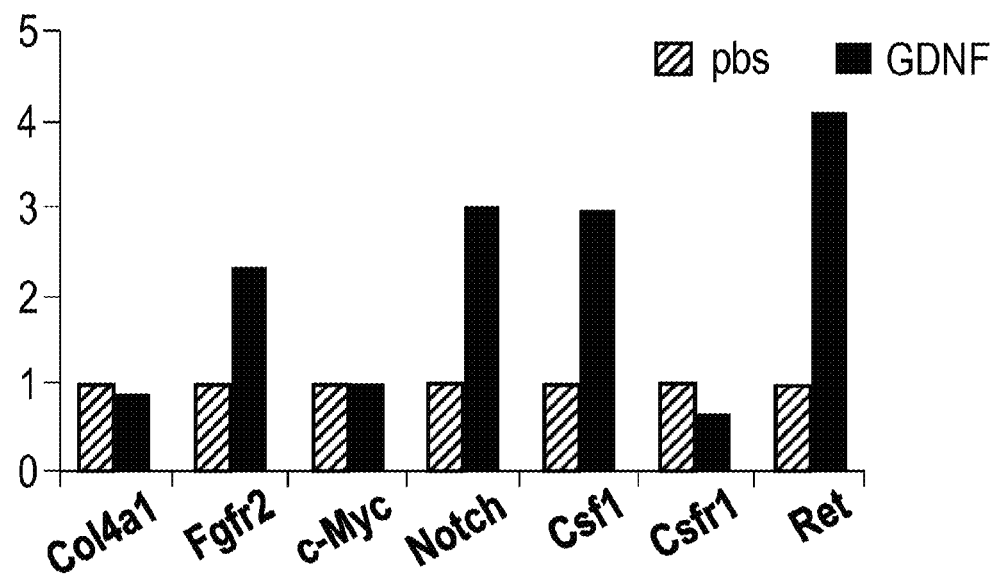

We analyzed the effects of GDNF (R&D system, cat no. 512-GF) on skin by quantitative RT-PCR (q-RT-PCR). For this total RNA was extracted from about 100 mg, about 8 mm diameter, skin tissue isolated from area injected either with PBS or 0.5 mg/ml GDNF protein 6 days after injection. RNA isolation was performed using Trizol Plus kit from Invitrogen. qRT-PCR of specific genes listed below was performed using One step Real-time RT-PCR SYBR green kit from Applied biosystems. Beta actin was used as internal control. Transcripts of selected genes were analyzed and normalized to beta-actin. The PCR protocol used here followed the RT-PCR protocol according to Applied Biosystems One step Real-time RT-PCR protocols. We tested expression of coHal, Ret, Fgfrl, c-myc, Notch1, Csfl and Csfrl. A four-fold increase in Ret transcript was seen, and a three-fold increase for Notch1 and Oil. For Ret and Notch1 one a role in hair growth has been described previously (Kato et al. 2001; Vauclair et al. 2005), and it may be that the action of GDNF is mediated by upregulating these. To date, it has not been shown that Notch1 is part of the GDNF signaling pathway, and this is the first time seeing this novel action of GDNF. We do not observe a change in c-myc, col4a1 and csfrl expression. For example c-myc is not described as part of the GDNF signaling pathway and can be considered as negative control. While, it is known that c-myc over-expression results in proliferation epidermal cells, it does not seem to play a role here (FIG. 7).

The primers used for the q-RT-PCR are:

```
Fgfr2-Forward
                                      (SEQ ID NO: 14)
5'-ctctctacgtcatagttgaatatg-3

Fgfr2-Reverse
                                      (SEQ ID NO: 15)
5'-atatccctggccaggccaaagtct-3'

Ret-Forward
                                      (SEQ ID NO: 16)
5'-agatgtttatgaggaagattccta-3

Ret-Reverse
                                      (SEQ ID NO: 17)
5'-Tcctcgctgcagttgtctggcctc-3'

Col4al-Forward
                                      (SEQ ID NO: 18)
5'-atgccctttctcttctgcaa-3'

Col4al-Reverse
                                      (SEQ ID NO: 27)
5'-ctgcggaatctgaatggtct-3'
```

```
Csfl-Forward
                                      (SEQ ID NO: 19)
5'-gatccctgagtctgtcttccacct-3'

Csfl-Reverse
                                      (SEQ ID NO: 20)
5'-cagttccacctgtctgtcctcatcc-3'

Csflr-Forward
                                      (SEQ ID NO: 21)
5'-gtaaagtggatggccccagagagc-3

Csflr-Reverse
                                      (SEQ ID NO: 22)
5'-taggctccaggtcccagcaggactg-3' c-Myc-Forward
                                      (SEQ ID NO: 23)
5'-cagctcgcccaaatcctgtacctcgt-3' c-Myc-Reverse
                                      (SEQ ID NO: 24)
5'-cagacaccacatcaatttcttcctc-3'

Notch1-Forward
                                      (SEQ ID NO: 25)
5'-tgaagaacggagccaacaaggacatgc-3'

Notch1- Reverse
                                      (SEQ ID NO: 26)
5'-gcaatcggtccatgtgatccgtgatgt-3'
```

Example 6: GDNF Accelerates Wound Healing in B6 Mice

Mice were anesthetized using isoflurane and fur removed using clipper from the dorsal side. Loose fur was removed with dry gauze dampened with 70% ethanol. Equal size 3 mm of full thickness wounds were set using a biopsy punch needle on the dorsal side of adult B6 mice. The mice were housed individually and monitored daily after surgery. Wounds were photographed on day 0 before injection and after one week, day 0 is counted as day of injection. Only one wound site was injected once with 100 µï of 0.5 mg/ml GDNF (R&D system, cat no. 512-GF) (arrow), the other wound was injected with PBS (vehicle control). The wound site that was injected with 100 µï of 0.5 mg/ml GDNF healed faster than the wound sites injected with PBS. After one week mice were sacrificed and tissue around the original wound was isolated to prepare sections. The sections of wound sites injected with PBS or GDNF were stained using H&E. By one week all layers of skin, epidermis, dermis and hair follicles are present at the wound site injected with GDNF compared to PBS injected sites (FIG. 8A). In the PBS control the skin does not show the three layers, but is still in the reconstruction phase after one week. The wound repair starts as early as 48 hrs after the wound is set with immune cells detectable. At the wound site red blood cell (RBC) infiltration is seen in both groups, but to a higher extent in the GDNF group (data not shown). By 96 hrs a complete layer of epithelium was observed throughout the wound site only for the GDNF group (FIG. 8B arrow) and many new blood vessels (arrowheads) are detectable in the GDNF injected site. In the PBS group less immune cells and blood vessels are detectable compared to the GDNF group. At the one week time point no new hair follicles are detectable in the PBS group.

Example 7: GDNF Accelerates Wound-Healing in Diabetic Mice

As diabetic model, we chose the diabetic mouse strain BKS.Cg-Dock7$^m$+/+Lepr$^{db}$/J (db/db; available from The Jackson Laboratory stock number 000642). Mice were anesthetized using isoflurane and fur removed using clipper from the dorsal side. Loose fur was removed with dry gauze dampened with 70% ethanol before 3 mm full thickness wounds were set into the dorsal skin creating 4/wounds per mouse using a biopsy punch needle. The mice were housed individually and monitored daily after surgery. We treated the wounds either with 100 µï PBS or 100 µï of 0.5 mg/ml GDNF recombinant protein (R&D system, cat no. 512-GF). Mice were sacrificed at several time points and tissues was collected, fixed in formalin, sectioned and sections were stained with H&E. 96 hours after wound setting and GDNF treatment, we detected neovascularization and blood vessel formation (FIG. 9A arrowhead) more pronounced in the GDNF group compared to the PBS group. The increase in new blood vessel formation in db/db mice treated with GDNF can be seen at the one week time point. Compared to wild type B6 mice wound healing in diabetes, takes two weeks instead of one week when injected with 0.5 mg/ml of GDNF but at a higher dose (250 µï of 0.5 mg/ml GDNF or 2.5 fold more). The healing process is greatly accelerated after GDNF treatment even in the db/db mice.

Example 8: GDNF Induces Blood Vessel Formation

FVB/NJ mice (n=5) (available from The Jackson Laboratory, cat no. 001800) were s.c. injected with 100 µï of PBS or 100 µï of 0.5 mg/ml GDNF protein (R&D system, cat no. 512-GF). 9 days after the injection the mice were sacrificed and the skin was isolated, photographed and fixed in formalin for histology. When the skin was isolated it was very striking that that the skin was showed more blood vessels with more branching in the GDNF group (Fig. xx). Analyzing the H&E stained sections confirmed an increased number of blood vessels around the GDNF injection site in comparison to the PBS injected tissue.

Example 9: Hydrogel Formulations for Therapeutic Administration

An optimized formulation of liposome-encapsulated GDNF in hydrogel is prepared for the growth factor to be applied at the wound site. The growth factor is loaded into the liposomes and mix with chitosan. Briefly, liposomes (from Sigma #L4395) are dissolved in 10 ml of chloroform:methanol mixture (2:1) in round bottom flask and air dried to thin film by jet stream of argon gas at 40° C. The thin film is then hydrated in water and passed through 0.2 um polycarbonate filters a few times to get small unilamellar vesicles. The liposome-encapsulated GDNF is prepared by sonication of the lipids and growth factor in 0.250:1 ratio (w/w) of growth factor to the lipid. These liposomes are added to a prechilled solution of chitosan (1.8% wt/vol in 2% acetic acid) by gentle stirring for 10 minutes before applying at the wound site.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein can be utilized according to such related embodiments of the present invention. Thus, the following claims are intended to encompass within their scope modifications, substitutions, and variations to processes, manufactures, compositions of matter, compounds, means, methods, and/or steps disclosed herein.

The contents of any patents, patent applications, and references cited throughout the specification are herein incorporated by reference in their entireties.

We claim:

1. A method for promoting hair growth comprising:
administering to skin comprising hair follicles of a subject in need thereof a therapeutically effective dose of a topical formulation comprising recombinant human glial cell-derived neurotrophic factor (GDNF),
wherein the therapeutically effective dose is 1-10 mg, 10-20 mg, 20-30 mg, or 30-40 mg, thereby promoting an increase in hair follicle number of the skin of the subject.

2. The method of claim 1, wherein the subject has androgenetic alopecia.

3. The method of claim 2, wherein the subject is a female.

4. The method of claim 1, wherein the subject has acute or chronic telogen effluvium.

5. The method of claim 1, wherein the topical formulation is administered to the scalp of the subject.

6. The method of claim 1, wherein the topical formulation is an emulsion.

7. The method of claim 6, wherein the emulsion is a continuous phase emulsion.

8. The method of claim 6, wherein the emulsion is a disperse phase emulsion.

9. The method of claim 6, wherein the emulsion is a cream, lotion, ointment, or gel.

10. The method of claim 6, wherein the emulsion is an oil-in-water emulsion or a water-in-oil emulsion.

11. The method of claim 6, wherein the emulsion is a microemulsion.

12. The method of claim 1, wherein the therapeutically effective dose is administered daily for at least 3-5 days.

13. The method of claim 1, wherein the recombinant human GDNF is obtained from plant cells.

14. The method of claim 1, further comprising, prior to the administering:
obtaining the recombinant human GDNF from plant cells; and
formulating the topical formulation comprising the recombinant GDNF.

15. The method of claim 14, wherein the topical formulation is administered to the scalp of the subject.

16. The method of claim 15, wherein the therapeutically effective dose is administered daily for at least 3-5 days.

17. The method of claim 15, wherein the subject is a female.

18. The method of claim 1, wherein the therapeutically effective dose promotes a 25% increase in hair follicle number over a period of 3-4 months.

* * * * *